(12) United States Patent
Fyfe et al.

(10) Patent No.: US 9,790,209 B2
(45) Date of Patent: Oct. 17, 2017

(54) KINASE INHIBITORS

(71) Applicants: Respivert Limited, High Wycombe, Buckinghamshire (GB); Topivert Pharma Limited, London (GB)

(72) Inventors: Matthew Colin Thor Fyfe, London (GB); Premji Meghani, Nottingham (GB); Matthew Alexander Henry Stent, Camelford (GB); Stephen Malcolm Thom, Nottingham (GB); Claire Anne Walshe, London (GB)

(73) Assignees: Respivert Limited, High Wycombe, Buckinghamshire (GB); Topivert Pharma Limited, London (GB)

( * ) Notice: Subject to any disclaimer, the term of this patent is extended or adjusted under 35 U.S.C. 154(b) by 0 days.

(21) Appl. No.: 15/225,377

(22) Filed: Aug. 1, 2016

(65) Prior Publication Data

US 2016/0340343 A1 Nov. 24, 2016

Related U.S. Application Data

(63) Continuation of application No. 14/424,627, filed as application No. PCT/GB2013/052251 on Aug. 28, 2013, now abandoned.

(30) Foreign Application Priority Data

Aug. 29, 2012 (GB) .................................. 1215369.8
Mar. 15, 2013 (GB) .................................. 1304777.4

(51) Int. Cl.

| | |
|---|---|
| *C07D 403/14* | (2006.01) |
| *C07D 403/12* | (2006.01) |
| *C07D 401/14* | (2006.01) |
| *A61K 31/4439* | (2006.01) |
| *A61K 31/506* | (2006.01) |
| *A61K 31/5377* | (2006.01) |
| *C07C 51/347* | (2006.01) |
| *C07C 255/17* | (2006.01) |
| *C07D 231/38* | (2006.01) |
| *C07D 239/47* | (2006.01) |
| *C07D 401/12* | (2006.01) |
| *C07F 7/08* | (2006.01) |

(52) U.S. Cl.

CPC ........ *C07D 403/14* (2013.01); *A61K 31/4439* (2013.01); *A61K 31/506* (2013.01); *A61K 31/5377* (2013.01); *C07C 51/347* (2013.01); *C07C 255/17* (2013.01); *C07D 231/38* (2013.01); *C07D 239/47* (2013.01); *C07D 401/12* (2013.01); *C07D 401/14* (2013.01); *C07D 403/12* (2013.01); *C07F 7/083* (2013.01)

(58) Field of Classification Search

CPC .. C07D 231/38; C07D 239/47; C07D 401/12; C07D 401/14; C07D 403/12; C07D 403/14; C07C 51/347; C07C 255/17; C07F 7/083; A61K 31/4439; A61K 31/506; A61K 31/5377

See application file for complete search history.

(56) References Cited

U.S. PATENT DOCUMENTS

| | | |
|---|---|---|
| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |

(Continued)

FOREIGN PATENT DOCUMENTS

| | | |
|---|---|---|
| EP | 2 578 582 A1 | 4/2013 |
| WO | WO 99/23091 A1 | 5/1999 |

(Continued)

OTHER PUBLICATIONS

Kinase Inhibitors, Methods in Molecular Biology 795 (B. Kuster ed., 2012).*
R. Singh et al., 42 Annual Reports in Medicinal Chemistry, 379-391 (2007).*
M.E. Weinblatt et al., 363 The New England Journal of Medicine 1303-1312 (2010).*
N. Yamamoto et al., 306 The Journal of Pharmacology and Experimental Therapeutics, 1174-1181 (2003).*
E.S. Masuda et al., 21 Pulmonary Pharmacology & Therapeutics, 461-467 (2008).*
D. Singh et al., 50 The Journal of Clinical Pharmacology, 94-100 (2010).*

(Continued)

*Primary Examiner* — Alexander R Pagano
(74) *Attorney, Agent, or Firm* — Knobbe, Martens, Olson & Bear, LLP

(57) ABSTRACT

There are provided compounds of formula I, wherein $R^1$ to $R^5$, $X^1$, $X^2$, Ar, L, E, A, $A^1$, G and $G^1$ have meanings given in the description, which compounds have antiinflammatory activity (e.g. through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

19 Claims, No Drawings

(56) References Cited

U.S. PATENT DOCUMENTS

| | | |
|---|---|---|
| 6,852,717 B2 | 2/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Hoa et al. |
| 7,838,541 B2 | 11/2010 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 8,927,563 B2 | 1/2015 | Fyfe et al. |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,242,960 B2 | 1/2016 | Ito et al. |
| 9,249,125 B2 | 2/2016 | Duffy et al. |
| 9,481,648 B2 | 11/2016 | Baker et al. |
| 9,701,670 B2 | 7/2017 | Cariou |
| 2001/0011135 A1 | 8/2001 | Riedl et al. |
| 2004/0152725 A1 | 8/2004 | Moss et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2013/0150343 A1 | 6/2013 | Van Niel et al. |
| 2013/0156826 A1 | 6/2013 | Murray et al. |
| 2014/0057915 A1 | 2/2014 | Cariou et al. |
| 2014/0114061 A1 | 4/2014 | Kugimoto et al. |
| 2014/0228410 A1 | 8/2014 | Ito et al. |
| 2014/0249169 A1 | 9/2014 | Ito et al. |
| 2014/0296208 A1 | 10/2014 | Baker et al. |
| 2015/0166483 A1 | 6/2015 | Fyfe |
| 2015/0203475 A1 | 7/2015 | Duffy et al. |
| 2015/0210722 A1 | 7/2015 | Fyfe et al. |
| 2015/0218137 A1 | 8/2015 | Cariou et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe et al. |
| 2016/0039797 A1 | 2/2016 | Fyfe |
| 2016/0045482 A1 | 2/2016 | Charron |
| 2016/0045512 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood et al. |
| 2016/0130256 A1 | 5/2016 | King-Underwood et al. |
| 2016/0318909 A1 | 11/2016 | Fyfe |
| 2016/0340375 A1 | 11/2016 | Fyfe et al. |
| 2016/0376232 A1 | 12/2016 | Thom |

FOREIGN PATENT DOCUMENTS

| | | | |
|---|---|---|---|
| WO | WO 99/32111 A1 | 7/1999 | |
| WO | WO 00/41698 A1 | 7/2000 | |
| WO | WO 00/43384 A1 | 7/2000 | |
| WO | WO 00/55139 A1 | 9/2000 | |
| WO | WO 01/04115 A1 | 1/2001 | |
| WO | WO 01/36403 A1 | 5/2001 | |
| WO | WO 02/083628 A1 | 10/2002 | |
| WO | WO 02/092576 A1 | 11/2002 | |
| WO | WO 03/005999 A1 | 1/2003 | |
| WO | WO 03/068223 A1 | 8/2003 | |
| WO | WO 03/068228 A1 | 8/2003 | |
| WO | WO 03/072569 A1 | 9/2003 | |
| WO | WO 03072569 A1 * | 9/2003 | ........... C07D 231/40 |
| WO | WO 2004/113352 A1 | 12/2004 | |
| WO | WO 2005/023761 A1 | 3/2005 | |
| WO | WO 2005/044825 A1 | 5/2005 | |
| WO | WO 2006/043090 A1 | 4/2006 | |
| WO | WO 2006/072589 A2 | 7/2006 | |
| WO | WO 2007/053394 A1 | 5/2007 | |
| WO | WO 2010/038085 A1 | 4/2010 | |
| WO | WO 2010/038086 A1 | 4/2010 | |
| WO | WO 2010/067130 A1 | 6/2010 | |
| WO | WO 2010/067131 A1 | 6/2010 | |
| WO | WO 2010/112936 A1 | 10/2010 | |
| WO | WO 2011/070368 A1 | 6/2011 | |
| WO | WO 2011/070369 A1 | 6/2011 | |
| WO | WO 2011/121366 A1 | 10/2011 | |
| WO | WO 2011/124923 A1 | 10/2011 | |
| WO | WO 2011/124930 A1 | 10/2011 | |
| WO | WO 2011/154738 A1 | 12/2011 | |
| WO | WO 2011/158039 A1 | 12/2011 | |
| WO | WO 2011/158042 A1 | 12/2011 | |
| WO | WO 2011/158044 A1 | 12/2011 | |
| WO | WO 2013/050756 A1 | 4/2013 | |
| WO | WO 2013/050757 A1 | 4/2013 | |
| WO | WO 2013/083604 A1 | 6/2013 | |
| WO | WO 2014/027209 A1 | 2/2014 | |
| WO | WO 2014/033446 A1 | 3/2014 | |
| WO | WO 2014/033448 A1 | 3/2014 | |
| WO | WO 2014/033449 A1 | 3/2014 | |
| WO | WO 2014/140582 A1 | 9/2014 | |
| WO | WO 2014/162121 A1 | 10/2014 | |
| WO | WO 2015/121444 A1 | 8/2015 | |
| WO | WO 2015/121660 A1 | 8/2015 | |

OTHER PUBLICATIONS

A.C. Brando et al., 63 Pharmacological Reports, 1029-1039 (2011).*
R.S. Jope et al., 32 Neurochemical Research, 577-595 (2007).*
M.P. Kim et al., 335 Cell and Tissue Research, 249-259 (2009).*
G. Liu et al., 31 Arteriosclerosis, Thrombosis and Vascular Biology, 1342-1350 (2011).*
U. McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
U.S. Appl. No. 14/561,290, filed Dec. 5, 2014, Murray.
U.S. Appl. No. 15/105,912, filed Jun. 17, 2016, Fyfe, et al.
U.S. Appl. No. 15/207,915, filed Jul. 12, 2016, Fyfe.
Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
Biancheri, et al. 2016 "Effect of Narrow Spectrum Versus Selective Kinase Inhibitors on the Intestinal Proinflammatory Immune Response in Ulcerative Colitis" *Inflamm Bowel Dis* 22: 1306-1315.
Boehm, et al. 2000 "New inhibitors of p38 kinase" *Expert Opinion on Therapeutic Patents* 10(1): 25-37.
Brando, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
CAS Registry No. 1379397-83-7, 2012 American Chemical Society.
CAS Registry No. 1384608-34-7, 2012 American Chemical Society.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Dietrich, et al. 2010 "The design, synthesis, and evaluation of 8 hybrid DFG-out allosteric kinase inhibitors: A structural analysis of the binding interactions of Gleevec®, Nexavar®, and BIRB-796" *Bioorganic & Medicinal Chemistry* 18; 5738-5748.
Dodeller, et al. 2006 "The p38 mitogen-activated protein kinase signaling cascade in CD4 T cells" *Arthritis Research & Therapy* 8(2): 1-11.

(56) References Cited

OTHER PUBLICATIONS

Dumas, et al. 2004 "Recent developments in the discovery of protein kinase inhibitors from the urea class" *Current Opinion in Drug Discovery & Development* 7(5); 600-616.

Jope, et al. 2007 "Glycogen synthase kinase-3 (GSK3): Inflammation, diseases, and therapeutics" *Neurochem Res* 32: 577-595.

Kim, et al. 2009 "Src family kinases as mediators of endothelial permeability: effects on inflammation and metastasis" *Cell Tissue Res* 335: 249-259.

Kuster 2012 "Kinase Inhibitors" *Methods in Molecular Biology* 795: 1-44.

Liu, et al. 2011 "Src phosphorylation of endothelial cell surface intercellular adhesion molecule-1 mediates neutrophil adhesion and contributes to the mechanism of lung inflammation" *Arteriosclerosis, Thrombosis and Vascular Biology* 31: 1342-1350.

Masuda, et al. 2008 "Syk inhibitors as treatment for allergic rhinitis" *Pulmonary Pharmacology & Therapeutics* 21: 461-467.

McDermott, et al. 2009 "Personalized cancer therapy with selective kinase inhibitors: An emerging paradigm in medical oncology" *Journal of Clinical Oncology* 27(33): 5650-5659.

Onions, et al. 2016 "The discovery of narrow spectrum kinase inhibitors: New therapeutic agents for the treatment of COPD and steroid-resistant asthma" *Journal of Medicinal Chemistry*; 1-70.

Patterson, et al. 2013 "Protein kinase inhibitors in the treatment of inflammatory and autoimmune diseases" *Clinical and Experimental Immunology* 176; 1-10.

Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.

Sawyers 2008 "The cancer biomarker problem" *Nature* 452: 548-552.

Singh, et al. 2007 "Spleen tyrosine kinase (Syk) biology, inhibitors and therapeutic applications" *Annual Reports in Medicinal Chemistry* 42: 379-391.

Singh, et al 2010 "A randomized, placebo-controlled study of the effects of the p38 MAPK inhibitor SB-681323 on blood biomarkers of inflammation in COPD patients" *The Journal of Clinical Pharmacology* 50: 94-100.

To, et al. 2015 "Potent anti-inflammatory effects of the narrow spectrum kinase inhibitor RV1088 on rheumatoid arthritis synovial membrane cells" *Britch Journal of Pharmacology* 172: 3805-3816.

Weinblatt, et al. 2010 "An oral spleen tyrosine kinase (Syk) inhibitor for rheumatoid arthritis" *The New England Journal of Medicine* 363(14): 1303-1312.

Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide Dihydrocholoride (BAY 61-3606) Blacks antigen-induced airway inflammation in rodents" *The Journal of Pharmacology and Experimental Therapeutics* 306(3): 1174-1181.

Zambon, et al. 2010 "Novel hinge binder improves activity and pharmacokinetic properties of BRAF inhibitors" *Journal of Medicinal Chemistry* 53; 5639-5655.

Brinkmann, et al. 2010 "Fingolimod (FTY720): discovery and development of an oral drug to treat multiple sclerosis" *Nature Reviews* 9: 883-897.

Judge, et al. 2006 "Potassium channel blockers in multiple sclerosis: Neuronal $K_V$ channels and effects of symptomatic treatment" *Pharmacology & Therapeutics* 111: 224-259.

Sutherland, et al. 2004 "Management of chronic obstructive pulmonary disease" *The New England Journal of Medicine* 350: 2689-2697.

\* cited by examiner

KINASE INHIBITORS

FIELD OF THE INVENTION

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis) and gastrointestinal tract (such as Crohn's disease and ulcerative colitis).

BACKGROUND

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body; are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. *J., Br. J. Pharmacol.*, 2006, 149:393-404);
- biopsies from IBD patients (Docena, G. et al., *J. of Trans. Immunol.*, 2010, 162:108-115); and
- in vivo animal models (Underwood, D. C. et al., *Am. J. Physiol.*, 2000, 279:L895-902; Nath, P. et al., *Eur. J. Pharmacol.*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB 796, VX702, SC10469 and SC10323, has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract A*56) demonstrates that silencing p38 MAPK gamma has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., Gut, 2002, 50:507-512, Docena, G. et al., *J. of Trans. Immunol,* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a P38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNγ/IL-2) or Th2 (IL5/TGFβ) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Behçets patients (Chi W. et al. *Invest Ophthalmol Vis Sci.* 2008 49:3058-64). In support, Direskeneli and colleagues demonstrated that Behcets patients have increased Th17 cells and decreased Treg cells in their peripheral blood (Direskeneli H. et al. *J Allergy Clin Immunol.* 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release-inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharsky kinases") have been found to alter the frequency of micronucleus formation in vitro (Olaharsky, A. J. et al., *PLoS Comput. Biol.,* 2009, 5(7)). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharsky kinases such as GSK3α by optimisation of the dose and/or by changing the route of administration of a molecule, it would be advantageous to identify further therapeutically useful molecules with low or negligible inhibition of Olaharsky kinases, such as GSK 3α and/or have low or negligible disruption of mitotic processes (e.g. as measured in a mitosis assay).

Various urea derivatives are disclosed as having anti-inflammatory properties (see, for example, WO 01/36403, WO 01/4115, WO 02/092576, WO 2003/068228, WO 2003/072569, WO 2004/113352, WO 2007/053394 and *Bioorg. Med. Chem. Lett.* 2007, 17, 354-357). Nevertheless, there remains a need to identify and develop alternative p38 MAP kinase inhibitors, and particularly inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that certain alkyne-containing diaryl ureas inhibit one or more of p38 MAP kinase, Syk and Src family kinases and therefore possess good anti-inflammatory properties.

Thus, according to a first aspect of the invention, there is provided a compound of formula I,

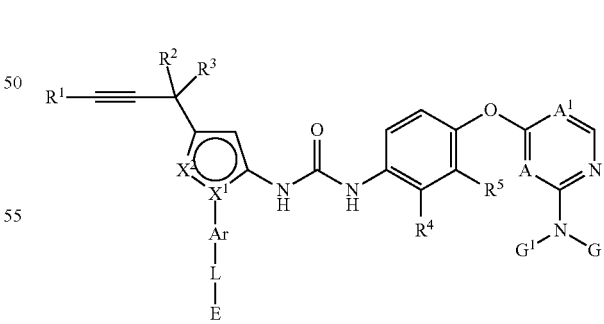

wherein
$R^1$ represents H or $C_{1-3}$ alkyl;
$R^2$ and $R^3$ independently represent H or $C_{1-3}$ alkyl, or $R^2$ and $R^3$ together combine to form $C_{2-3}$ alkylene;
$X^1$ and $X^2$ are both N, or $X^1$ is C and $X^2$ is either O or S;
Ar is phenyl or a 5- or 6-membered heteroaryl group containing one or more heteroatoms selected from N, O and S, which phenyl and heteroaryl groups are optionally substituted by one or more substituents selected from halo, $C_{1-4}$ alkyl, $C_{1-4}$ haloalkyl, $C_{1-4}$ alkoxy, hydroxy, amino and cyano;

L is a direct bond or $C_{1-2}$ alkylene;

E represents:
(a) H, halo, hydroxy, $NR^{6a}R^{6b}$, cyano, $C(O)OR^{6c}$, $C(O)NR^{6d}R^{6e}$, SH, $S(O)_nR^8$, $S(O)_2NR^{6f}R^{6g}$,
(b) $C_{1-8}$ alkyl, $C_{2-8}$ alkenyl, $C_{2-8}$ alkynyl, $C_{1-8}$ alkoxy, which latter four groups are optionally substituted by one or more substituents selected from halo and $NR^{7a}R^{7b}$,
(c) $C_{3-8}$ cycloalkyl, $Het^1$ or $Ar^1$, which latter three groups are optionally substituted by one or more substituents selected from halo, hydroxy and $C_{1-3}$ alkyl;

$R^{6a}$ to $R^{6g}$ independently represent H or $C_{1-4}$ alkyl, or any one or more of the pairs $R^{6a}$ and $R^{6b}$, $R^{6d}$ and $R^{6e}$, and $R^{6f}$ and $R^{6g}$, when taken together with the N-atom to which each pair is attached, form a saturated 4- to 7-membered heterocyclic group, which heterocyclic group contains one N atom (the atom to which the pairs of substituents are attached) and, optionally, one or more further heteroatoms selected from O, S and N, and which heterocyclic group is optionally substituted by one or more $C_{1-2}$ alkyl groups;

$R^{7a}$ and $R^{7b}$, independently on each occurrence, represent H or $C_{1-4}$ alkyl, or, together with the N-atom to which they are attached, form a 5- to 7-membered heterocyclic group that is fully saturated, partially unsaturated or fully aromatic and which heterocyclic group contains one N atom (the atom to which $R^{7a}$ and $R^{7b}$ are attached) and, optionally, one or more further heteroatoms selected from O, S and N, and which heterocyclic group is optionally substituted by one or more substituents selected from halo, hydroxy, oxo, $C_{1-4}$ alkyl and $C_{1-4}$ alkoxy;

$R^8$ represents $C_{1-4}$ haloalkyl, $C_{1-4}$ alkyl, $C_{3-8}$ cycloalkyl or $Ar^2$, which latter three groups are optionally substituted by one or more substituents selected from halo, hydroxy and $C_{1-3}$ alkyl;

$Ar^1$ and $Ar^2$ independently represent $C_{6-14}$ carbocyclic aryl groups, which groups may be monocyclic, bicyclic or tricyclic and which groups contain at least one ring which is fully aromatic, n is 0, 1 or 2;

$R^4$ and $R^5$ are each independently $C_{1-3}$ alkyl, $C_{1-3}$ haloalkyl, cyano or halo,
or $R^4$ and $R^5$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo,
or $R^4$ and $R^5$, together with the C-atoms to which they are attached, form a fused phenyl or $Het^2$ ring, which latter two rings are optionally substituted by one or more substituents selected from $C_{1-3}$ alkyl, $C_{1-3}$ haloalkyl, cyano and halo;

$Het^1$ and $Het^2$ independently represent 5- to 7-membered heterocyclic groups that are fully saturated, partially unsaturated or fully aromatic, which heterocyclic groups contain one or more heteroatoms selected from N, O and S;

one of A and $A^1$ represents N and the other represents CH, or both of A and $A^1$ represent CH;

G represents
phenyl optionally substituted by one or more $Y^1$ or $Het^3$ optionally substituted by one or more $Y^2$;

$G^1$ represents H;
or G and $G^1$ together combine to form $C_{3-6}$ alkylene optionally substituted by one or more substituents selected from halo, hydroxy and $C_{1-3}$ alkyl, which latter group is optionally substituted by one or more halo atoms or by hydroxy;

each $Y^1$ is independently selected from the group consisting of
halo, hydroxy, cyano, $SF_5$, $—OC(O)NH_2$,
$P(O)R^{9a}R^{9b}$,
$J^1-N(R^{9c})R^{9d}$,
$J^2-S(O)_2R^{9e}$,
$J^3-[CH_2(CH_2)_{0-1}CH_2—O]_{2-8}—R^{9f}$,
$—C\equiv C—R^{9g}$,
$—N=S(O)R^{9h}R^{9i}$,
$Het^a$,
$C_{1-6}$ alkyl, $C_{3-6}$ cycloalkyl, $C_{1-6}$ alkoxy, $C_{3-6}$ cycloalkoxy, $—S(O)_{0-1}—C_{1-6}$ alkyl and $—S(O)_{0-1}—C_{3-6}$ cycloalkyl which latter six groups are optionally substituted by one or more substituents selected from halo, hydroxy, $C_{1-3}$ alkyl, $C_{1-3}$ alkoxy and $C_{3-6}$ cycloalkyl;

each $Y^2$ independently represents oxo or $Y^1$;

$J^1$ represents
a direct bond,
$—C(O)—$
$—[C(O)]_p—C_{1-8}$ alkylene,
$—C(O)NR^{10a}—CH_2—[C_{1-7}$ alkylene]-,
$-Q^1-CH_2—[C_{1-5}$ alkylene]-,
the alkylene parts of which latter four groups are optionally substituted by one or more substituents selected from halo, $C_{1-3}$ alkyl and hydroxy;

$J^2$ represents
a direct bond,
$—O—$,
$—NH—$
$C_{1-6}$ alkylene or
$-Q^2-CH_2—[C_{1-5}$ alkylene]-,
the alkylene parts of which latter two groups are optionally substituted by one or more substituents selected from halo, $C_{1-3}$ alkyl and hydroxy;

$J^3$ represents $—O—$ or $S(O)_{0-2}$;

$Q^1$ and $Q^2$ independently represent O or $S(O)_{0-2}$;

p represents 0 or 1;

$R^{9a}$ and $R^{9b}$ independently represent $C_{1-3}$ alkyl or $C_{1-3}$ alkoxy, or $R^{9a}$ and $R^{9b}$ together combine to form $C_{4-6}$ alkylene;

$R^{9c}$ and $R^{9d}$ independently represent H or $C_{1-8}$ alkyl, which latter group is optionally substituted by $R^{10b}$ and/or one or more substituents selected from halo and hydroxy; or $R^{9c}$ and $R^{9d}$, together with the N-atom to which they are attached, form a 4- to 7-membered heterocyclic group that is fully saturated, partially unsaturated or fully aromatic and which heterocyclic group contains one N atom (the atom to which $R^{9c}$ and
$R^{9d}$ are attached) and, optionally, one or more further heteroatoms selected from O, S and N, and which heterocyclic group is optionally substituted by one or more substituents selected from halo, hydroxy, oxo, $C_{1-4}$ alkyl and $C_{1-4}$ alkoxy;

$R^{9e}$ represents $C_{1-6}$ alkyl, $C_{3-6}$ cycloalkyl or phenyl, which latter three groups are optionally substituted by one or more substituents selected from halo, hydroxy, $C_{1-3}$ alkyl, $C_{1-3}$ alkoxy and $C_{3-6}$ cycloalkyl;

$R^{9f}$, $R^{9g}$, $R^{9h}$ and $R^{9i}$ independently represent $C_{1-4}$ alkyl optionally substituted by one or more halo atoms, or $R^{9f}$ and $R^{9g}$ independently represent H;

$R^{10a}$ represents H or $C_{1-3}$ alkyl optionally substituted by one or more halo atoms;

$R^{10b}$ represents $C_{1-4}$ alkoxy, $S—C_{1-4}$ alkyl, phenyl or $Het^4$, which latter two groups are optionally substituted by one or more substituents selected from halo, $C_{1-4}$ alkyl, $C_{1-4}$haloalkyl, $C_{1-4}$ alkoxy, hydroxy, amino and cyano;

$Het^3$ represents a 5- to 10-membered heteroaromatic group, which group is monocyclic or bicyclic and contains at least one carbocyclic or heterocyclic ring that is fully aromatic, and which group contains one or more heteroatoms selected from N, O and S;

$Het^4$ represents a 4- to 10-membered heterocyclic group that is fully saturated, partially unsaturated or fully aromatic, which heterocyclic group contains one or more heteroatoms selected from N, O and S;

$Het^a$ represents a 5- or 6-membered heterocyclic group that is fully saturated, partially unsaturated or fully aromatic, which group contains one or more heteroatoms selected from N, O and S, and which group is optionally substituted by one or more substituents selected from halo, hydroxy, $C_{1-3}$ alkyl, $C_{1-3}$ alkoxy and $C_{3-6}$ cycloalkyl, or a pharmaceutically acceptable salt, solvate or isotopic derivative thereof, which compounds may be referred to hereinafter as "the compounds of the invention".

DETAILED DESCRIPTION

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:

(a) the compound of formula I is not isotopically enriched or labelled with respect to any atoms of the compound; and (b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention. In particular, the invention includes the keto-enol tautomerism existing between indolin-2-one and 2-hydroxyindole.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched.

In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

Values of $Het^a$ that may be mentioned include imidazolyl (e.g. imidazol-2-yl), isothiazolyl (e.g. isothiazol-3-yl), isoxazolyl (e.g. isoxazol-3-yl), 1,2,4-oxadiazolyl (e.g. 1,2,4-oxadiazol-3-yl or 1,2,4-oxadiazol-5-yl), 1,3,4-oxadiazolyl, oxazolyl (e.g. oxazol-2-yl), pyridinyl (e.g. pyridin-2-yl), pyrimidinyl (e.g. pyrimidin-2-yl), 1,2,4-thiadiazolyl (e.g. 1,2,4-thiadiazol-3-yl or 1,2,4-thiadiazol-5-yl), 1,3,4-thiadiazolyl, thiazolyl (e.g. thiazol-2-yl), 1,2,3-triazolyl (e.g. 1,2,3-triazol-1-yl, 1,2,3-triazol-4-yl or 1,2,3-triazol-5-yl) and 1,2,4-triazolyl (e.g. 1,2,4-triazol-1-yl, 1,2,4-triazol-3-yl or 1,2,4-triazol-5-yl).

Unless otherwise specified, the term "halo" includes references to fluoro, chloro, bromo or iodo, in particular to fluoro, chloro or bromo, especially fluoro or chloro.

Embodiments of the invention that may be mentioned include those in which one or more of the following definitions apply to the compound of formula I:

$R^1$ represents $C_{1-2}$ alkyl or, particularly, H;

$R^2$ and $R^3$ independently represent $C_{1-2}$ alkyl, or $R^2$ and $R^3$ together combine to form $C_2$ alkylene;

$X^1$ and $X^2$ are both N;

Ar is pyrimidinyl or, particularly, phenyl or pyridinyl, which three groups are optionally substituted by one or more substituents selected from halo, $C_{1-3}$ alkyl and $C_{1-3}$ alkoxy;

L is a direct bond;

E represents H, halo, $C_{1-6}$ alkyl, $C_{2-6}$ alkenyl, $C_{2-6}$ alkynyl or $C_{1-6}$ alkoxy, which latter four groups are optionally substituted by one or more halo substituents or by $NR^{7a}R^{7b}$, $R^{7a}$ and $R^{7b}$, independently on each occurrence, represent $C_{1-2}$ alkyl, or, together with the N-atom to which they are attached, form a 5- or 6-membered heterocyclic group that is fully saturated and which heterocyclic group contains one N atom (the atom to which $R^{7a}$ and $R^{7b}$ are attached) and, optionally, one further heteroatom selected from O, S and N, and which heterocyclic group is optionally substituted by one or more substituents selected from halo, hydroxy, oxo, $C_{1-4}$ alkyl and $C_{1-4}$ alkoxy;

$R^4$ and $R^5$ are each independently cyano or halo, or $R^4$ and $R^5$, together with the C-atoms to which they are attached, form a fused phenyl or $Het^2$ ring;

$Het^2$ represents a 6-membered heteroaromatic group containing one or two N atoms;

A represents N or CH and $A^1$ represents CH;

G represents phenyl optionally substituted by one or more $Y^1$ or $Het^3$ optionally substituted by one or more $Y^2$;

each $Y^1$ is independently selected from the group consisting of halo, hydroxy, cyano, P(O)$R^{9a}R^{9b}$, —C≡C—H, $J^1$-N($R^{9c}$)$R^{9d}$, —O—[CH$_2$CH$_2$O]$_{2-7}$—$R^{9f}$, —S—C$_{1-4}$ alkyl, —S—C$_{1-4}$ alkyl and C$_{1-4}$ alkoxy, which latter three groups are optionally substituted by hydroxy or by one or more halo atoms (e.g. each $Y^1$ is independently selected from the group consisting of halo, hydroxy, cyano, P(O)$R^{9a}R^{9b}$, $J^1$-N($R^{9c}$)$R^{9d}$, —O—[CH$_2$CH$_2$O]$_{2-7}$—$R^{9f}$, —S—C$_{1-4}$ alkyl, —S—C$_{1-4}$ alkyl and C$_{1-4}$ alkoxy, which latter three groups are optionally substituted by hydroxy or by one or more halo atoms);

$G^1$ represents H;

each $Y^2$ is independently oxo or $Y^1$;

$J^1$ represents
  a direct bond,
  —C(O)—,
  C$_{1-4}$ alkylene,
  —C(O)NH—CH$_2$—[C$_{1-3}$ alkylene]-,
  -Q$^1$-CH$_2$—[C$_{1-3}$ alkylene]-,
  the alkylene parts of which latter three groups are optionally substituted by or by one or more substituents selected from halo and hydroxy;

$R^{9a}$ and $R^{9b}$ independently represent C$_{1-3}$ alkyl (e.g. methyl), or $R^{9a}$ and $R^{9b}$ together combine to form C$_{4-5}$ alkylene;

$R^9$ and $R^{9d}$, independently on each occurrence, represent H or C$_{1-4}$ alkyl, which latter group is optionally substituted by one or more substituents selected from halo and hydroxy, or together with the N-atom to which they are attached, $R^{9c}$ and $R^{9c}$ form a 4- to 7-membered heterocyclic group that is fully saturated, partially unsaturated or fully aromatic and which heterocyclic group contains one N atom (the atom to which $R^{9c}$ and $R^{9d}$ are attached) and, optionally, one or more further heteroatoms selected from O, S and N, and which heterocyclic group is optionally substituted by one or more substituents selected from halo, hydroxy, oxo, C$_{1-4}$ alkyl and C$_{1-4}$ alkoxy;

$R^{9f}$ represents H or C$_{1-2}$ alkyl;

Het$^3$ represents a 5- to 10-membered heteroaromatic group, which group is monocyclic or bicyclic and contains at least one carbocyclic or heterocyclic ring that is fully aromatic, and which group contains one to four heteroatoms selected from N, O and S.

Further embodiments of the invention that may be mentioned include those in which the compound of formula I is a compound of formula Ia, Ia wherein
$R^1$ represents C$_{1-2}$ alkyl or, particularly, H;

$R^2$ and $R^3$ independently represent H or C$_{1-2}$ alkyl, or $R^2$ and $R^3$ together combine to form C$_2$ alkylene;

A represents CH or N;

$A^2$ represents N or, particularly, CH;

$R^4$ and $R^5$ are both halo, or $R^4$ and $R^5$, together with the C-atoms to which they are attached, form a fused phenyl ring;

$R^a$ represents C$_{1-2}$ alkoxy or, particularly, C$_{1-2}$ alkyl, which latter two groups are optionally substituted by one or more halo atoms, or $R^a$ represents C$_{1-2}$ alkyl or C$_2$ alkoxy, which latter two groups are substituted by NR$^{7a}$R$^{7b}$;

$R^{7a}$ and $R^{7b}$ both represent C$_{1-2}$ alkyl or, together with the N-atom to which they are attached, form a 5- or 6-membered heterocyclic group that is fully saturated and which heterocyclic group contains one N atom (the atom to which $R^{7a}$ and $R^{7b}$ are attached) and, optionally, one further heteroatom selected from O, S and N, and which heterocyclic group is optionally substituted by one or more substituents selected from halo, hydroxy, oxo, C$_{1-4}$ alkyl and C$_{1-4}$ alkoxy;

$A^3$ and $A^4$ both represent CH, or one of $A^3$ and $A^4$ represents N and the other represents CH;

$R^b$, $R^c$ and $R^d$ independently represent H, halo, hydroxy, —C≡C—H, C$_{1-4}$ alkylene-N(R$^{9c}$)R$^{9d}$, —C(O)NH—CH$_2$—[C$_{1-3}$ alkylene]-N(R$^{9c}$)R$^{9d}$, -Q$^1$-CH$_2$—[C$_{1-3}$ alkylene]-N(R$^{9c}$)R$^{9d}$, —O—[CH$_2$CH$_2$O]$_{2-7}$—R$^{9f}$, C$_{1-4}$ alkyl, C$_{1-4}$ alkoxy or C(O)NHCl$_{1-4}$ alkyl, which latter three groups are optionally substituted by one or more halo atoms (e.g. one of $R^b$, $R^c$ and $R^d$ represents H, —C(O)NH—CH$_2$—[C$_{1-3}$ alkylene]-N(R$^{9c}$)R$^{9d}$ or -Q$^1$-CH$_2$—[C$_{1-3}$ alkylene]-N(R$^{9c}$)R$^{9d}$, and the other two of $R^b$, $R^c$ and $R^d$ represent H, halo, —C≡C—H, C$_{1-4}$ alkyl or C$_{1-4}$ alkoxy, which latter two groups are optionally substituted by one or more halo atoms), (for example, $R^b$, $R^c$ and $R^d$ independently represent H, halo, hydroxy, C$_{1-4}$ alkylene-N(R$^{9c}$)R$^{9d}$, —C(O)NH—CH$_2$—[C$_{1-3}$ alkylene]-N(R$^{9c}$)R$^{9d}$, -Q$^1$-CH$_2$—[C$_{1-3}$ alkylene]-N(R$^{9c}$)R$^{9d}$, —O—[CH$_2$CH$_2$O]$_{2-7}$—R$^{9f}$, C$_{1-4}$ alkyl, C$_{1-4}$ alkoxy or C(O)NHCl$_{1-4}$ alkyl, which latter three groups are optionally substituted by one or more halo atoms (e.g. one of $R^b$, $R^c$ and $R^d$ represents H, —C(O)NH—CH$_2$—[C$_{1-3}$ alkylene]-N(R$^{9c}$)R$^{9d}$ or -Q$^1$-CH$_2$—[C$_{1-3}$ alkylene]-N(R$^{9c}$)R$^{9d}$, and the other two of $R^b$, $R^c$ and $R^d$ represent H, halo, C$_{1-4}$ alkyl or C$_{1-4}$ alkoxy, which latter two groups are optionally substituted by one or more halo atoms)), or $R^b$ and $R^c$, together with the C-atoms to which they are attached, form a fused, 5- or 6-membered heteroaromatic or heterocyclic ring, which ring:
 (i) contains one to three heteroatoms selected from N, O and S; and
 (ii) is optionally substituted by one or more substituents selected from H, halo, hydroxy, oxo, amino, C$_{1-2}$ alkyl and C$_{1-2}$ alkoxy, which latter two groups are optionally substituted by one or more halo atoms;

$R^9$ and $R^{9d}$ both represent C$_{1-2}$ alkyl or, together with the N-atom to which they are attached, form a 5- or 6-membered heterocyclic group that is fully saturated and which heterocyclic group contains one N atom (the atom to which R$^{9c}$ and R$^{9d}$ are attached) and, optionally, one further heteroatom selected from O, S and N, and which heterocyclic group is optionally substituted by one or more substituents selected from halo, hydroxy, oxo, C$_{1-4}$ alkyl and C$_{1-4}$ alkoxy; and $R^{9f}$ represents H or, particularly, methyl, or a pharmaceutically acceptable salt, solvate or isotopic derivative thereof.

Still further embodiments of the invention that may be mentioned include those in which the compound of formula Ia is a compound of formula Ib,

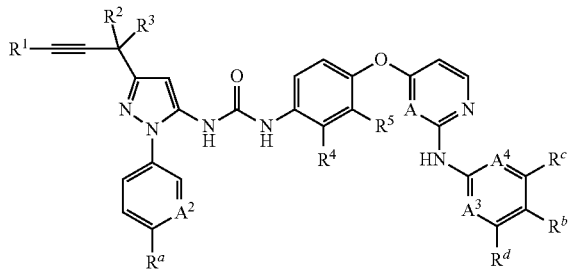

or a pharmaceutically acceptable salt, solvate or isotopic derivative thereof,
wherein $R^1$ to $R^5$, $A$, $A^2$, $A^3$, $A^4$, $R^a$ to $R^d$ are as defined above in respect of compounds of formula Ia.

Embodiments of the invention that may be mentioned include those in which, in the compound of formula Ia or Ib:
(1) $R^b$ to $R^d$ all represent H (e.g. when A represents CH);
(2) $R^b$ is H and $R^c$ and $R^d$ independently represent H, halo, —C≡C—H, $C_{1-4}$ alkylene-N($R^{9c}$)$R^{9d}$, —C(O)NH—CH$_2$—[$C_{1-3}$ alkylene]-N($R^{9c}$)$R^{9d}$, -Q$^1$-CH$_2$—[$C_{1-3}$ alkylene]-N($R^{9c}$)$R^{9d}$, —O—[CH$_2$CH$_2$O]$_{2-7}$—CH$_3$, $C_{1-4}$ alkyl, $C_{1-4}$ alkoxy, C(O)NHC$_{1-4}$ alkyl, which latter three groups are optionally substituted by one or more halo atoms
  (e.g. $R^b$ represents H, $R^c$ represents H, halo, —C≡C—H, $C_{1-4}$ alkyl or $C_{1-4}$ alkoxy, which latter two groups are optionally substituted by one or more halo atoms, and $R^d$ represents —C(O)NH—CH$_2$CH$_2$—N($R^{9c}$)$R^{9d}$, -Q$^1$-CH$_2$CH$_2$—N($R^{9c}$)$R^{9d}$ or —O—[CH$_2$CH$_2$O]$_{2-7}$—CH$_3$)
  (for example, $R^b$ is H and $R^c$ and $R^d$ independently represent H, halo, $C_{1-4}$ alkylene-N($R^{9c}$)$R^{9d}$, —C(O)NH—CH$_2$—[$C_{1-3}$ alkylene]-N($R^{9c}$)$R^{9d}$, -Q$^1$-CH$_2$—[$C_{1-3}$alkylene]-N($R^{9c}$)$R^{9d}$, —O—[CH$_2$CH$_2$O]$_{2-7}$—CH$_3$, $C_{1-4}$ alkyl, $C_{1-4}$ alkoxy, C(O)NHC$_{1-4}$ alkyl, which latter three groups are optionally substituted by one or more halo atoms
  (e.g. $R^b$ represents H, $R^c$ represents H, halo, $C_{1-4}$ alkyl or $C_{1-4}$ alkoxy, which latter two groups are optionally substituted by one or more halo atoms, and $R^d$ represents —C(O)NH—CH$_2$CH$_2$—N($R^{9c}$)$R^{9d}$, -Q$^1$-CH$_2$CH$_2$—N($R^{9c}$)$R^{9d}$ or —O—[CH$_2$CH$_2$O]$_{2-7}$—CH$_3$)); or
(3) $R^d$ is H, halo, or $C_{1-4}$ alkyl, which latter group is optionally substituted by one or more halo atoms, and $R^b$ and $R^c$, together with the C-atoms to which they are attached, form a fused, 5- or 6-membered (e.g. 5-membered) heteroaromatic or heterocyclic ring, which ring:
  (i) contains one to three (e.g. one or two) heteroatoms selected from N, O and S (such as one or two N atoms); and
  (ii) is optionally substituted by one or more substituents selected from H, halo, hydroxy, oxo, amino, $C_{1-2}$ alkyl and $C_{1-2}$ alkoxy (e.g. selected from H, oxo and $C_{1-2}$ alkyl), which latter two groups are optionally substituted by one or more halo atoms.

Further embodiments of the invention that may be mentioned include those in which one or more of the following definitions apply to the compound of formula Ia or Ib:
(1) $R^1$ is H;
(2) $R^2$ and $R^3$ represent H or, particularly, methyl;
(3) $R^4$ and $R^5$ are both chloro or, together with the C-atoms to which they are attached, form a fused phenyl ring;
(4) $A^2$ represents CH;
(5) $R^a$ represents methyl;
(6) $A^3$ represents CH or N and $A^4$ represents CH;
(7) either
  (i) $R^b$, $R^c$ and $R^d$ are all H,
  (ii) $R^b$ and $R^c$ are H and $R^d$ represents —O—CH$_2$CH$_2$—N($R^{9c}$)$R^{9d}$
  (iii) one of $R^b$, $R^c$ and $R^d$ is $C_{1-2}$ alkylene-N($R^{9c}$)$R^{9d}$, —O—CH$_2$CH$_2$—N($R^{9c}$)$R^{9d}$, —C(O)NH—CH$_2$CH$_2$—N($R^{9c}$)$R^{9d}$ or —O—[CH$_2$CH$_2$O]$_{2-7}$—CH$_3$, and the other two of $R^b$, $R^c$ and $R^d$ are selected from H, —C≡C—H, $C_{1-2}$ alkyl and $C_{1-2}$ alkoxy, which latter two groups are optionally substituted by one or more halo atoms
  (e.g. one of $R^b$, $R^c$ and $R^d$ is $C_{1-2}$ alkylene-N($R^{9c}$)$R^{9d}$, —O—CH$_2$CH$_2$—N($R^{9c}$)$R^{9d}$, —C(O)NH—CH$_2$CH$_2$—N($R^{9c}$)$R^{9d}$ or —O—[CH$_2$CH$_2$O]$_{2-7}$—CH$_3$, and the other two of $R^b$, $R^c$ and $R^d$ are selected from H, $C_{1-2}$ alkyl and $C_{1-2}$ alkoxy, which latter two groups are optionally substituted by one or more halo atoms), or
  (iv) $R^d$ is H or methyl and $R^b$ and $R^c$, together with the C-atoms to which they are attached and optional substituents thereon, form a fused ring selected from pyrrolidinone and pyrazole;
(7) N$R^{9c}$$R^{9d}$ represents dimethylamino or morpholin-4-yl.

Particular embodiments of the compounds of formula I, Ia and Ib that may be mentioned include those in which the structural fragment

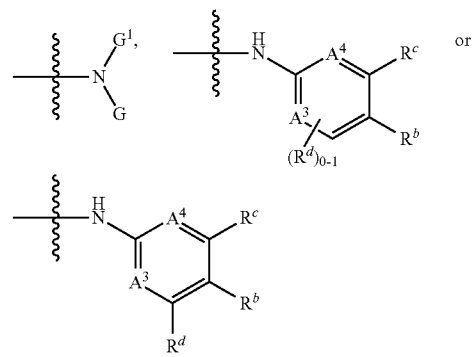

represents a group selected from:

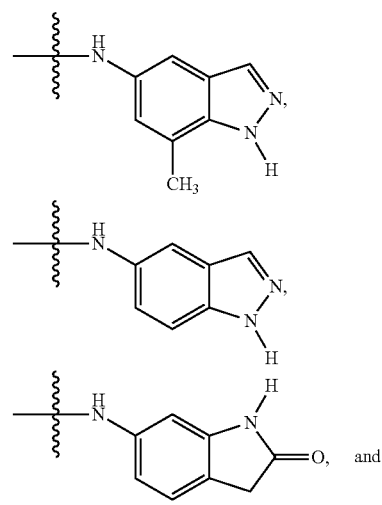

-continued

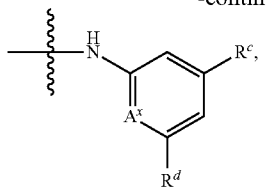

wherein $R^c$ and $R^d$ are as defined above in respect of compounds of formula Ia or Ib (such as wherein $R^c$ and $R^d$ are both H), and $A^x$ represents N or, particularly, CH.

In this regard, particular embodiments of the invention that may be mentioned include those in which the compound of formula I, Ia or Ib is a compound of formula Ic, Id or Ie, $R^{d1}$ is as defined above for $R^d$ in respect of compounds of formula Ia and Ib (e.g. $R^{d1}$ is methyl).

Embodiments of the invention that may be mentioned include those in which one or more of the following definitions apply to the compound of formula Ic, Id or Ie:
(1) $R^1$ is H;
(2) $R^2$ and $R^3$ represent H or, particularly, methyl;
(3) $R^4$ and $R^5$, together with the C-atoms to which they are attached, form a fused phenyl ring;
(3) $A^2$ represents CH;
(4) $R^a$ represents methyl;
(5) $A^x$ represents N or, particularly, CH;
(6) $R^{d1}$ represents H or, particularly, methyl;
(7) $R^{c2}$ represents H, methyl, trifluoromethyl, —C≡C—H, trifluoromethoxy or methoxy (e.g. H, methoxy or trifluoromethoxy)

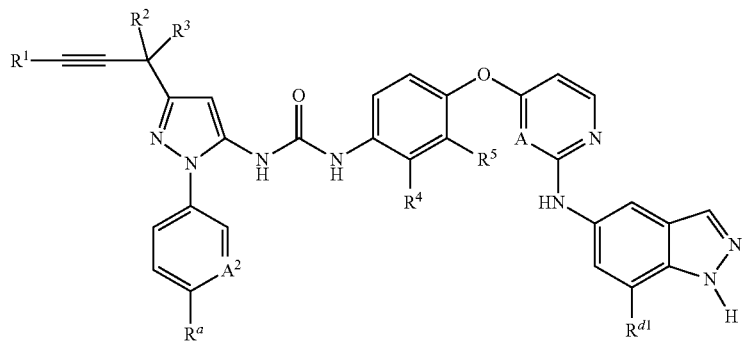

Ic

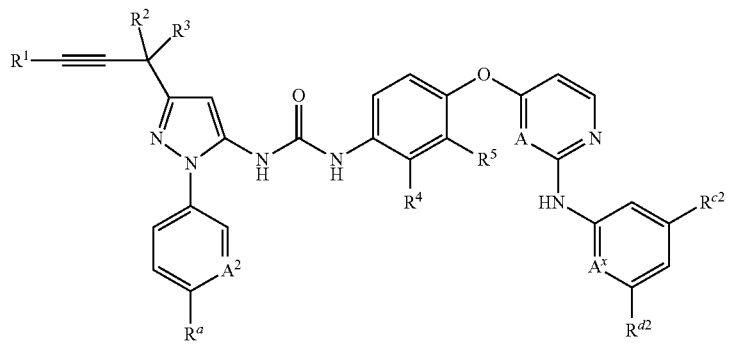

Id

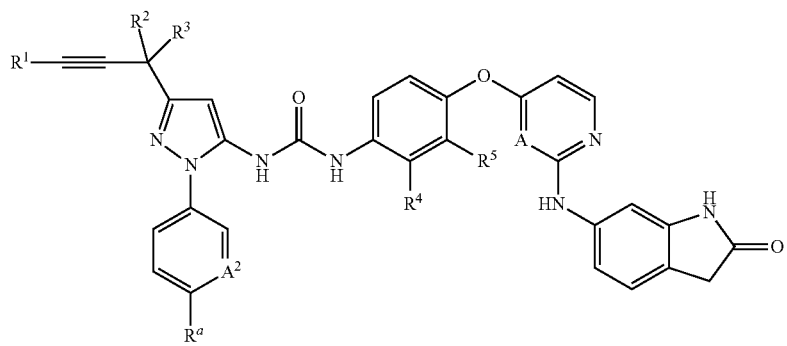

Ie or a pharmaceutically acceptable salt, solvate or isotopic derivative thereof,
wherein
$R^1$ to $R^5$, A, $A^2$, $A^x$ and $R^a$ are as defined above in respect of compounds of formula Ia and Ib;
$R^{c2}$ and $R^{d2}$ are defined above for $R^c$ and $R^d$ in respect of compounds of formula Ia and Ib; and (for example, $R^{c2}$ represents trifluoromethyl, trifluoromethoxy or, particularly, H, methyl, or methoxy (such as H or methoxy));
(8) $R^{d2}$ represents methoxy, ethoxy, or, particularly, H, —C(O)NH—CH$_2$CH$_2$—N(R$^{9c}$)R$^{9d}$, —O—[CH$_2$CH$_2$O]$_{2-7}$—CH$_3$ or —O—CH$_2$CH$_2$—N(R$^{9c}$)R$^{9d}$ (for example, $R^{d2}$ represents methoxy, ethoxy, —O—

[CH$_2$CH$_2$O]$_{2-7}$—CH$_3$ or, particularly, H, —C(O)NH—CH$_2$CH$_2$—N(R$^{9c}$)R$^{9d}$ or —O—CH$_2$CH$_2$—N(R$^{9c}$)R$^{9d}$ (such as H or —O—CH$_2$CH$_2$—N(R$^{9c}$)R$^{9d}$));

(9) NR$^{9c}$R$^{9d}$ represents dimethylamino or morpholin-4-yl.

Particular embodiments that may be mentioned therefore include compounds of formula Id as hereinbefore defined, but in which:

(i) R$^{c2}$ represents H and R$^{d2}$ represents —O—[CH$_2$CH$_2$O]$_{2-7}$—CH$_3$, —C(O)NH—CH$_2$CH$_2$—N(R$^{9c}$)R$^{9d}$ or, particularly, —O—CH$_2$CH$_2$—N(R$^{9c}$)R$^{9d}$, (ii) both of R$^{c2}$ and R$^{d2}$ represent H, or (iii) R$^{c2}$ represents CH$_3$, —C≡C—H, —CF$_3$, —OCF$_3$ or —OCH$_3$ (e.g. CH$_3$, —CF$_3$, —OCF$_3$ or, particularly, —OCH$_3$) and R$^{d2}$ represents —C(O)NH—CH$_2$CH$_2$—N(R$^{9c}$)R$^{9d}$, —O—[CH$_2$CH$_2$O]$_{2-7}$—CH$_3$ or —O—CH$_2$CH$_2$—N(R$^{9c}$)R$^{9d}$ (e.g. —O—[CH$_2$CH$_2$O]$_{2-7}$—CH$_3$ or, particularly, —C(O)NH—CH$_2$CH$_2$—N(R$^{9c}$)R$^{9d}$ or —O—CH$_2$CH$_2$—N(R$^{9c}$)R$^{9d}$).

Other compounds of formula I, Ia, Ib, Ic, Id or Ie that may be mentioned include the compounds of the examples described hereinafter. Thus, embodiments of the invention that may be mentioned include those in which the compound of formula I, Ia, Ib, Ic, Id or Ie is a compound selected from the list:

1-(3-(2-methylbut-3-yn-2-yl)-1-(p-tolyl)-1H-pyrazol-5-yl)-3-(4-((2-(phenylamino)pyrimidin-4-yl)oxy)naphthalen-1-yl)urea;

1-(4-((2-((7-methyl-1H-indazol-5-yl)amino)pyrimidin-4-yl)oxy)naphthalen-1-yl)-3-(3-(2-methylbut-3-yn-2-yl)-1-(p-tolyl)-1H-pyrazol-5-yl)urea;

1-(3-(2-methylbut-3-yn-2-yl)-1-(p-tolyl)-1H-pyrazol-5-yl)-3-(4-((2-((2-oxoindolin-6-yl)amino)pyrimidin-4-yl)oxy)naphthalen-1-yl)urea;

3-methoxy-5-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)benzamide;

1-(3-(2-methylbut-3-yn-2-yl)-1-(p-tolyl)-1H-pyrazol-5-yl)-3-(4-((2-((3-(2-morpholinoethoxy)phenyl)amino)pyrimidin-4-yl)oxy)naphthalen-1-yl)urea;

1-(4-((2-((3-(2-(dimethylamino)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea;

1-(3-(2-methylbut-3-yn-2-yl)-1-(p-tolyl)-1H-pyrazol-5-yl)-3-(4-((2-(phenylamino)pyridin-4-yl)oxy)naphthalen-1-yl)urea;

1-(4-((2-((3-methoxy-5-(2-morpholinoethoxy)phenyl)amino)pyrimidin-4-yl)oxy)naphthalen-1-yl)-3-(3-(2-methylbut-3-yn-2-yl)-1-(p-tolyl)-1H-pyrazol-5-yl) urea;

1-(2,3-dichloro-4-((2-((7-methyl-1H-indazol-5-yl)amino)pyrimidin-4-yl)oxy)phenyl)-3-(3-(2-methylbut-3-yn-2-yl)-1-(p-tolyl)-1H-pyrazol-5-yl)urea;

1-(4-((2-((6-(2-(dimethylamino)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea;

1-(4-((2-((4-(2-(dimethylamino)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea;

3-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethyl)benzamide;

1-(4-((2-((3-methoxy-5-(2-(2-(2-methoxyethoxy)ethoxy)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl) urea;

3-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethoxy)benzamide;

3-ethynyl-5-((4-((4-(3-(3-(2-methylbut-3-yn-2-yl)-1-(p-tolyl)-1H-pyrazol-5-yl)ureido) naphthalen-1-yl)oxy)pyrimidin-2-yl)amino)-N-(2-morpholinoethyl)benzamide;

1-(3-(2-methylbut-3-yn-2-yl)-1-(p-tolyl)-1H-pyrazol-5-yl)-3-(4-((2-((6-(2-morpholinoethoxy) pyridin-2-yl)amino) pyrimidin-4-yl)oxy)naphthalen-1-yl)urea; and 1-(4-((2-((6-(2-(2-(2-methoxyethoxy)ethoxy)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl) urea, or a pharmaceutically acceptable salt, solvate or isotopic derivative thereof.

Examples of salts of compounds of formula I, Ia, Ib, Ic, Id or Ie include all pharmaceutically acceptable salts, such as, without limitation, acid addition salts of strong mineral acids such as HCl and HBr salts and addition salts of strong organic acids such as methanesulfonic acid.

References herein to a compound of the invention (a compounds of formula I, Ia, Ib, Ic, Id or Ie) are intended to include references to the compound and to all pharmaceutically acceptable salts, solvates and/or tautomers of said compound, unless the context specifically indicates otherwise. In this respect, solvates that may be mentioned include hydrates.

The compounds of the invention (compounds of formula I, Ia, Ib, Ic, Id or Ie) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising compound of formula I, Ia, Ib, Ic, Id or Ie, as hereinbefore defined, or pharmaceutically acceptable salt, solvate or isotopic derivative thereof, in admixture with a pharmaceutically acceptable adjuvant, diluent or carrier.

(b) A combination product comprising
 (A) a compound of formula I, Ia, Ib, Ic, Id or Ie, as hereinbefore defined, or pharmaceutically acceptable salt, solvate or isotopic derivative thereof, and
 (B) another therapeutic agent,
wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia, Ib, Ic, Id or Ie, as hereinbefore defined, or pharmaceutically acceptable salt, solvate or isotopic derivative thereof, and another therapeutic agent, in admixture with a pharmaceutically acceptable adjuvant, diluent or carrier (which formulation is hereinafter referred to as a "combined preparation").

It also encompasses a kit of parts comprising components:
 (i) a pharmaceutical formulation including a compound of formula I, Ia, Ib, Ic, Id or Ie, as hereinbefore defined, or pharmaceutically acceptable salt, solvate or isotopic derivative thereof, in admixture with a pharmaceutically acceptable adjuvant, diluent or carrier; and
 (ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, sad process comprising the step of admixing the compound of formula I, Ia, Ib, Ic, Id or Ie, as hereinbefore defined, or pharmaceutically acceptable salt, solvate or isotopic derivative thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ia, Ib, Ic, Id or Ie, as hereinbefore defined, or pharmaceutically acceptable salt, solvate or isotopic derivative thereof, for use in medicine (or for use as a medicament or as a pharmaceutical).

(e) A compound of formula I, Ia, Ib, Ic, Id or Ie, as hereinbefore defined, or pharmaceutically acceptable salt, solvate or isotopic derivative thereof, or a pharmaceutical formulation or combination product as defined in connection with aspect (a) or (b) of the invention, for use in the treatment or prevention of an inflammatory disease.

(f) The use of
a compound of formula I, Ia, Ib, Ic, Id or Ie, as hereinbefore defined, or pharmaceutically acceptable salt, solvate or isotopic derivative thereof, or
a pharmaceutical formulation or combination product as defined in connection with aspect (a) or (b) of the invention, for the preparation of a medicament for the treatment or prevention of an inflammatory disease.

(g) A method of treating or preventing an inflammatory disease, said method comprising administering to a subject an effective amount of
a compound of formula I, Ia, Ib, Ic, Id or Ie, as hereinbefore defined, or pharmaceutically acceptable salt, solvate or isotopic derivative thereof, or
a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
a compound of formula I, Ia, Ib, Ic, Id or Ie, as hereinbefore defined, or pharmaceutically acceptable salt, solvate or isotopic derivative thereof, or
a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in *Remington's Pharmaceutical Sciences,* 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity.

Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
- steroids (e.g. budesonide, beclomethasone dipropionate, fluticasone propionate, mometasone furoate, fluticasone furoate);
- beta agonists (e.g. terbutaline, salbutamol, salmeterol, formoterol); and
- xanthines (e.g. theophylline).

Further, for the treatment of gastrointestinal disorders (such as Crohn's disease or ulcerative colitis), the other therapeutic agent may be, for example, one or more agents selected from the list comprising:
- 5-aminosalicylic acid, or a prodrug thereof (such as sulfasalazine, olsalazine or bisalazide);
- corticosteroids (e.g. prednisolone, methylprednisolone, or budesonide);
- immunosuppressants (e.g. cyclosporin, tacrolimus, methotrexate, azathioprine or 6-mercaptopurine);
- anti-TNFα antibodies (e.g., infliximab, adalimumab, certolizumab pegol or golimumab);
- anti-IL12/IL23 antibodies (e.g., ustekinumab) or small molecule IL12/IL23 inhibitors (e.g., apilimod);
- Anti-α4β7 antibodies (e.g., vedolizumab);
- MAdCAM-1 blockers (e.g., PF-00547659);
- antibodies against the cell adhesion molecule α4-integrin (e.g., natalizumab);
- antibodies against the IL2 receptor a subunit (e.g., daclizumab or basiliximab);
- JAK3 inhibitors (e.g., tofacitinib or R348);
- Syk inhibitors and prodrugs thereof (e.g., fostamatinib and R-406);
- Phosphodiesterase-4 inhibitors (e.g., tetomilast);
- HMPL-004;
- probiotics;
- Dersalazine;
- semapimod/CPSI-2364; and
- protein kinase C inhibitors (e.g. AEB-071).

For the treatment of eye disorders (such as uveitis), the other therapeutic agent may be, for example, one or more agents selected from the list comprising:
- corticosteroids (e.g. dexamethasone, prednisolone, triamcinolone acetonide, difluprednate or fluocinolone acetonide);
- immunosuppressants (e.g. cyclosporin, voclosporin, azathioprine, methotrexate, mycophenolate mofetil or tacrolimus);
- anti-TNFα antibodies (e.g., infliximab, adalimumab, certolizumab pegol, ESBA-105 or golimumab);
- anti-IL-17A antibodies (e.g., secukinumab);
- mTOR inhibitors (e.g., sirolimus);
- VGX-1027;
- JAK3 inhibitors (e.g., tofacitinib or R348); and
- protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia, Ib, Ic, Id or Ie (or pharmaceutically acceptable salt, solvate or isotopic derivative thereof) is the sole pharmacologically active ingredient utilised in the treatment.

However, in other embodiments of aspects (e) to (g) above, the compound of formula I, Ia, Ib, Ic, Id or Ie (or pharmaceutically acceptable salt, solvate or isotopic derivative thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:

(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;

(ii) skin diseases or disorders having an inflammatory component, such as atopic dermatitis, allergic dermatitis, contact dermatitis or psoriasis;

(iii) nasal diseases or disorders having an inflammatory component, such as allergic rhinitis, rhinitis or sinusitis;

(iv) eye diseases or disorders having an inflammatory component, such as conjunctivitis, allergic conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation, or, particularly, uveitis (including posterior, anterior and pan uveitis), corneal graft and limbal cell transplant rejection; and (v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:

(a) reaction of a compound of formula II,

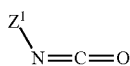

II with a compound of formula III,

III wherein one of $Z^1$ and $Z^2$ is a structural fragment of formula IV

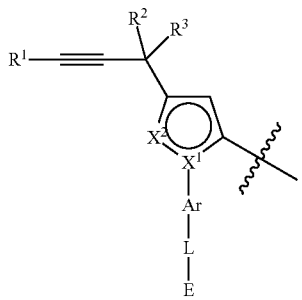

IV and the other of $Z^1$ and $Z^2$ is a structural fragment of formula V

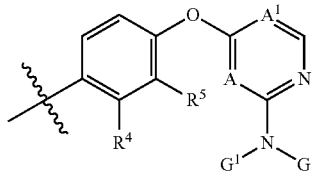

V where E, L, Ar, $X^1$, $X^2$, $R^1$ to $R^5$, A, $A^1$, G and $G^1$ are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);
(b) reaction of a compound of formula IIa,

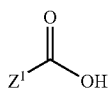

IIa wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula II, which compound is then reacted with a compound of formula III, as defined above, to provide the compound of formula I;
(c) reaction of a compound of formula IIb,

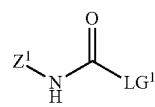

IIb wherein $LG^1$ represents a suitable leaving group (e.g. imidazolyl, chloro, or aryloxy) and $Z^1$ is as defined above, with a compound of formula III, as defined above, for example under conditions known to those skilled in the art, such as at ambient temperature (e.g. from 15 to 30° C.), optionally in the presence of an amine base (e.g. a sterically hindered base like N,N-diisopropylethylamine) and a suitable organic solvent (e.g. an aprotic solvent, such as dichloromethane);
(d) reaction of a compound of formula VI,

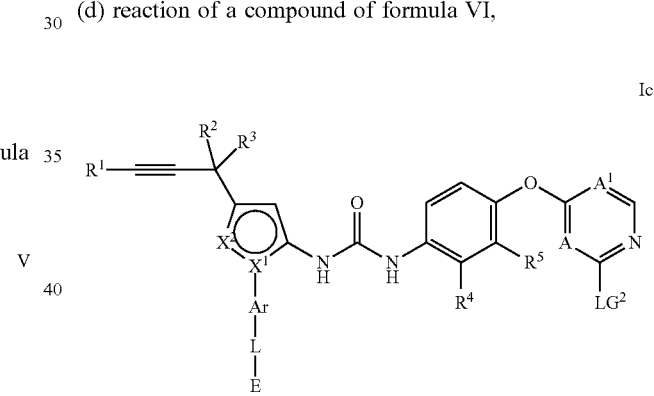

Ic wherein $LG^2$ represents a suitable leaving group (e.g. a halo group such as chloro or bromo) and E, L, Ar, $X^1$, $X^2$, $R^1$ to $R^5$, A and $A^1$ are as hereinbefore defined with a compound of formula VII,

VII wherein G and $G^1$ are as hereinbefore defined, for example under conditions known to those skilled in the art (e.g. as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid, for example in the presence of approximately 0.5 to 1 equivalents of such an acid relative to the compound of formula VI or formula VII);
or
(e) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII, Certain carboxylic acids of formula IIa, where $Z^1$ is a structural fragment of formula IV, in which both $X^1$ and $X^2$ are nitrogen, may be synthesised employing the route outlined in Scheme 1 below (see also: *Bioorg. Med. Chem. Lett.* 2007, 17, 354-357). This route commences with cycloaddition of trialkylsilylalkynes X with alkyl (Ak) diazoacetates XI to give pyrazoles XII. These pyrazoles are then coupled with aryl- or heteroaryl-boronic acids XIII, employing copper (II)-mediated Chan-Lam reactions (see, for example: *Tetrahedron Lett.* 1998, 39, 2941-2944), to furnish N-arylpyrazole esters XIV. Saponification of esters XIV, typically employing an alkali hydroxide, followed by acidification furnishes the desired carboxylic acids.

Scheme 1

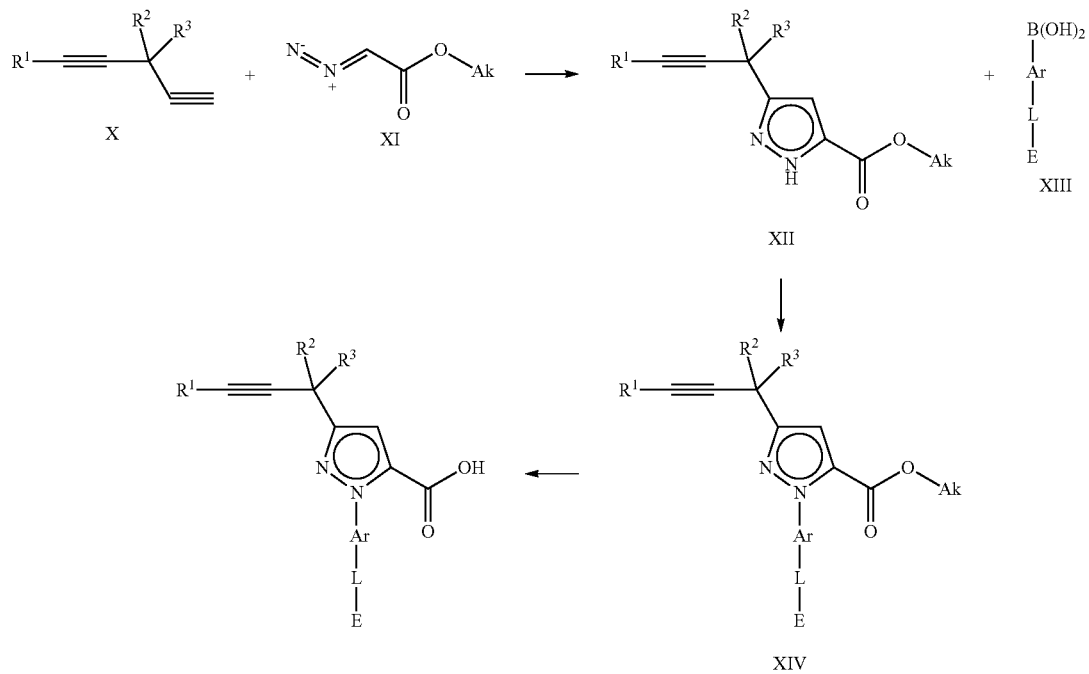

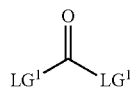

VIII wherein $LG^1$ is as hereinbefore defined, with a compound of formula IX,

IX wherein $Z^1$ is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Certain compounds of formula III in which $X^1$ and $X^2$ both represent N and $Z^2$ represents a structural fragment of formula IV, or compounds of formula IX in which $X^1$ and $X^2$ both represent N and $Z^1$ represents a structural fragment of formula IV, may be synthesised by a route such as that outlined in Scheme 2. In that route, alkyne ester XV (in which $R^x$ represents, for example, optionally substituted phenyl or, particularly, $C_{1-4}$ alkyl such as methyl) is reacted with acetonitrile in the presence of a strong base, such as sodium hydride. The resulting β-ketonitrile XVI is then condensed with arylhydrazine XVII to yield the desired 5-aminopyrazole.

Scheme 2

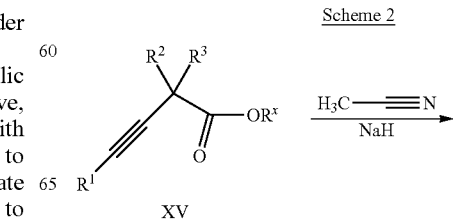

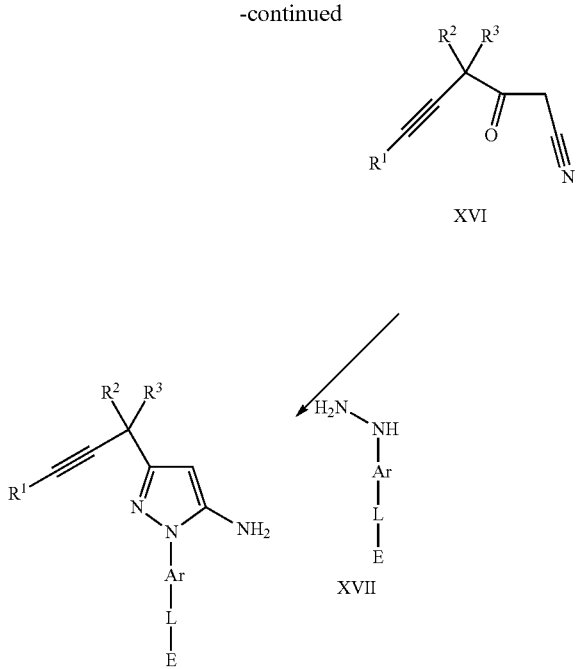

On the other hand, certain compounds of formula III in which $Z^2$ represents a structural fragment of formula V, or compounds of formula IX in which $Z^1$ represents a structural fragment of formula V, may be synthesised employing the route outlined in Scheme 3 (see, for example: WO 2003/072569; and WO 2008/046216), wherein $R^4$, $R^5$, A, $A^1$, G and $G^1$ are as hereinbefore defined, $LG^1$ and $LG^2$ represent leaving groups, e.g., halogen or methanesulfonyl, and FG represents a real or latent $NH_2$ group, i.e., a group that is readily transformed into an $NH_2$ group, such as nitro or a protected variant $NH-PG^2$, where $PG^2$ is a typical protecting group (see, for example: Greene, T. W.; Wuts, P. G. M. *Protective Groups in Organic Synthesis*; Wiley, 4th revised edition, 2006; ISBN-10: 0471697540), e.g., a carbamate ester or carboxamide. The sequence starts with the base-mediated $S_NAr$ displacement of $LG^1$ in XIX by the aroxides formed when XVIII is treated with base to generate ethers XX. The remaining halogen or methanesulfonyl substituents ($LG^2$) of the ether XX is then displaced i) by an amine of formula VII in a second $S_NAr$ reaction or (ii) via a Buchwald coupling (see, for example, WO 2009/017838) with an amine of formula VII to furnish the desired compound (when FG is $NH_2$), or XXI (when FG is nitro or $NH-PG^2$). When FG is nitro in XXI, the $NH_2$ group may be revealed by a reduction reaction, typically done through hydrogenation employing a suitable catalyst, e.g., palladium on carbon, or employing dissolving metal conditions, such as with iron in glacial acetic acid. Alternatively, when FG is a protecting group, the $NH_2$ group may be revealed by a deprotection reaction. Although only depicted as taking place in the final step of the sequence, it should be noted that the unmasking of the latent $NH_2$ group represented by FG can take place at any stage in the synthetic route shown in Scheme 3.

Scheme 3

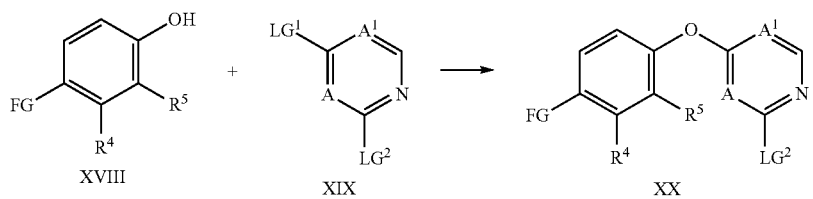

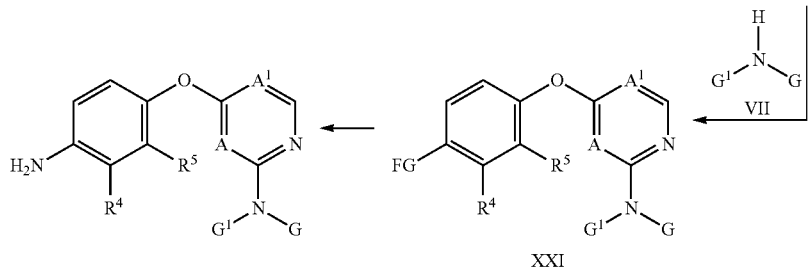

Certain compounds of formula XIV, where L is a direct bond and E is $C_{2-8}$ alkoxy substituted with $NR^{7a}R^{7b}$, may be synthesised employing the route highlighted in Scheme 4. In this route, phenols XXIII are alkylated with alkyl halides XXIV, where m is 1-7 and Hal is chloro, bromo or iodo, under basic conditions in Williamson ether syntheses (see, for example: *Eur. J. Med. Chem.* 2010, 45, 5965-5978). Phenols XXIII can be prepared from XXII—in which $PG^1$ is an appropriate protecting group that masks the reactive phenolic functionality (see, for example: Greene, T. W.; Wuts, P. G. M. *Protective Groups in Organic Synthesis*; Wiley, 4th revised edition, 2006; ISBN-10: 0471697540), e.g., tert-butyldimethylsilyl—by a typical deprotection reaction. The compounds of formula XXII may be synthesised using, for example, the above-mentioned Chan-Lam reactions (Scheme 1) of compounds of formula XIII where L is a direct bond and E is $O-PG^1$.

Scheme 4

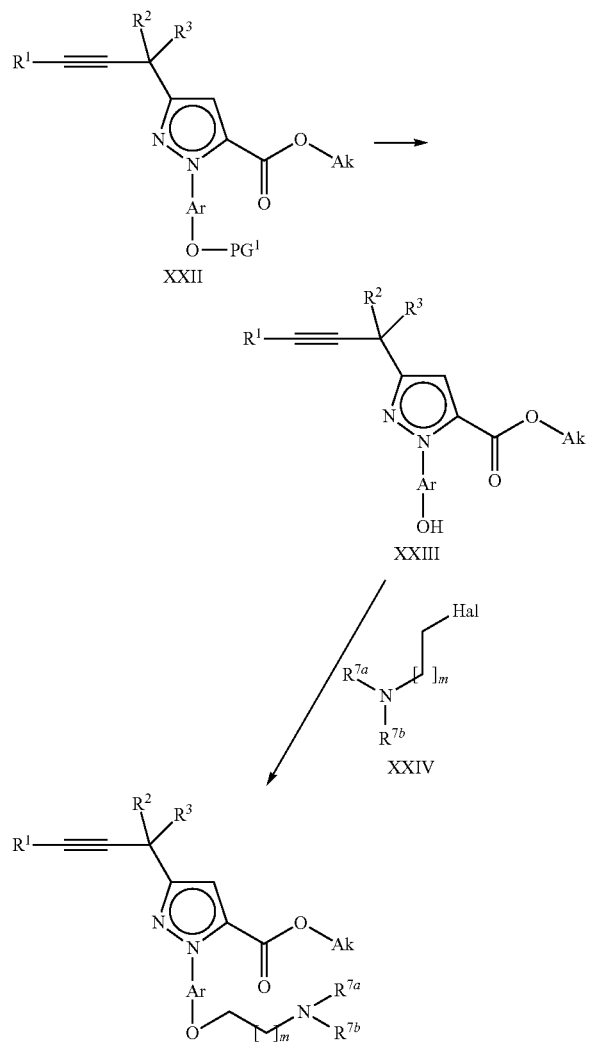

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va,

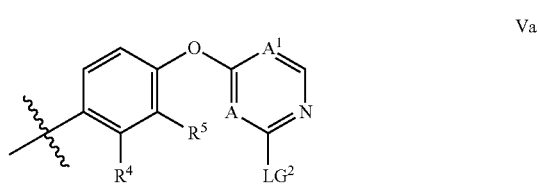

Va

It will be understood by persons skilled in the art that compounds represented by formulae II and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups $Z^1$ and $Z^2$ which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/087448 and WO 2007/089512.

Novel intermediates as described herein form an aspect of the invention. In this respect, further aspects of the invention relate to:
(i) a compound of formula II, IIa or IIb as hereinbefore defined, wherein $Z^1$ is a structural fragment of formula IV, as hereinbefore defined, or a salt or protected derivative thereof;
(ii) a compound of formula III, as hereinbefore defined, wherein $Z^2$ is a structural fragment of formula IV, as hereinbefore defined, or a salt or protected derivative thereof; and
(iii) a compound of formula VI, as hereinbefore defined, or a salt or protected derivative thereof.

In the compounds of formulae II, IIa, IIb, III and VI, the groups E, L, Ar, $X^1$, $X^2$, $R^1$ to $R^5$, A, $A^1$ and $LG^2$, when present, take any of the definitions for those groups as hereinbefore defined.

Protected derivatives of the compound of formula IIa include esters (e.g. $C_{1-4}$ alkyl esters) thereof.

Protected derivatives of the compound of formula III include those in which the essential $NH_2$ group is protected. In this respect, such protected derivatives include amides or, particularly, carbamates of those compounds. For example, those protected derivatives include compounds in which a H-atom of the $NH_2$ group is replaced by:

$R^1$—C(O)—, wherein $R^1$ is H, $C_{1-8}$ alkyl, phenyl or benzyl, which latter two groups are optionally substituted by one or more groups selected from halo, hydroxy, methyl and methoxy; or R"—O—C(O)—, wherein R" is tert-butyl, phenyl, benzyl or fluorenyl, which latter three groups are optionally substituted by one or more groups selected from halo, hydroxy, methyl and methoxy.

Although alkyne esters of formula XV may be commercially available or prepared by conventional methods, the present applicant has surprisingly discovered that the corresponding carboxylic acids of such esters may be advantageously prepared by a route involving carboxylation of a Grignard reagent containing a trialkylsilyl-protected alkyne.

Thus, according to a further aspect of the invention, there is provided a process for the preparation of a compound of formula XXV,

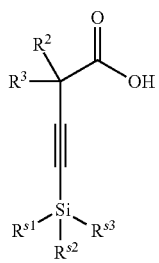

XXV wherein $R^{s1}$ to $R^{s3}$ independently represent $C_{1-4}$ alkyl and $R^2$ and $R^3$ are as hereinbefore defined, said process comprising the steps of:

(i) reaction of a compound of formula XXVI

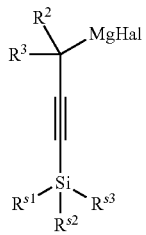

XXVI wherein $R^{s1}$ to $R^{s3}$, $R^2$ and $R^3$ are as hereinbefore defined and Hal represents a halogen selected from Cl, Br and I, with carbon dioxide, for example in the presence of a reaction-inert, aprotic organic solvent (e.g. a fully saturated ether that is either acyclic, such as diethylether, or is cyclic, such as THF); and (ii) acidification of the resulting carboxylic acid salt, for example using an aqueous acid (e.g. an aqueous hydrohalic acid such as aqueous hydrochloric acid).

In certain embodiments of this aspect of the invention, the compound of formula XXVI is prepared by reaction of the corresponding halo compound with magnesium metal. In this embodiment, step (i) of the above-described process may be replaced by the steps:

(ia) reaction of a compound of formula XXVII,

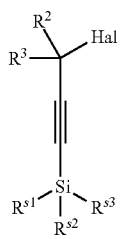

XXVII wherein $R^{s1}$ to $R^{s3}$, Hal, $R^2$ and $R^3$ are as hereinbefore defined, with magnesium metal (e.g. magnesium metal turnings that have been ground, e.g. by grinding in a pestle and mortar), for example under an inert atmosphere (e.g. nitrogen or a noble gas, such as argon) in the presence of a reaction-inert, aprotic organic solvent (e.g. a fully saturated ether that is either acyclic, such as diethylether, or is cyclic, such as THF); and (ib) reaction of the resulting compound of formula XXVI with carbon dioxide, for example in the presence of a reaction-inert, aprotic organic solvent (e.g. a fully saturated ether that is either acyclic, such as diethylether, or is cyclic, such as THF).

In particular embodiments, the compound of formula XXVI is formed in the same solvent system as used for the reaction with carbon dioxide (i.e. the compound of formula XXVII is reacted with carbon dioxide without isolation from the reaction mixture in which it is formed).

In any of the above embodiments of this aspect of the invention, any one or more (e.g. all) of the following may apply.

(a) The carbon dioxide is provided in solid form (i.e. as dry ice).

(b) The compound of formula XXVI is reacted with carbon dioxide by addition of a solvent mixture containing the compound of formula XXVI to solid carbon dioxide.

(c) The solvent mixture containing the compound of formula XXVI mentioned in (b) above is the solvent mixture in which the compound of formula XXVI is formed (from the compound of formula XXVII and magnesium metal).

(d) The compound of formula XXVII is prepared by a process comprising the steps of:

(i) reaction of a compound of formula XXVIII,

XXVIII wherein $R^{s1}$ to $R^{s3}$ are as hereinbefore defined, with an aryl (e.g. phenyl) or $C_{1-6}$ alkyl lithium reagent (e.g. t-BuLi or, particularly, n-BuLi), for example under an inert atmosphere (e.g. nitrogen or a noble gas, such as argon) at sub-ambient temperature (e.g. from −30 to −80° C.) in the presence of a reaction-inert, aprotic organic solvent (e.g. a fully saturated ether that is either acyclic, such as diethylether, or is cyclic, such as THF), followed by reaction of the resulting alkynyl lithium intermediate with a compound of formula XXIX,

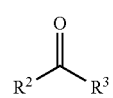

XXIX wherein $R^2$ and $R^3$ are as hereinbefore defined, at sub-ambient temperature (e.g. from −30 to −80° C., such as at from about −50° C. to about −70° C.), for example by addition of the compound of formula XXIX to the reaction mixture; and (ii) reaction of the resulting compound of formula XXX,

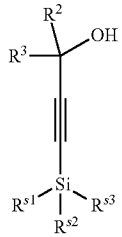

XXX wherein $R^{s1}$ to $R^{s3}$, $R^2$ and $R^3$ are as hereinbefore defined, with a chlorinating, brominating or iodinating agent (e.g. a concentrated hydrohalic acid, such as concentrated hydrochloric acid).

In a further aspect of the invention, there is also provided a process for the preparation of a compound of formula XXXI,

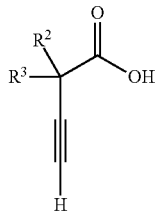

XXXI wherein $R^2$ and $R^3$ are as hereinbefore defined, said process comprising removal of the —Si($R^{s1}$)($R^{s2}$)($R^{s3}$) protecting group from a compound of formula XXV, as hereinbefore defined, for example under conditions known to those skilled in the art (e.g. by contacting the compound of formula XXV at ambient temperature with a mixture of an alkali metal hydroxide (such as KOH) and a $C_{1-4}$ alkyl alcohol, such as methanol).

In particular embodiments of this aspect of the invention, the compound of formula XXV is prepared according to a method as described above. In this respect, a particular embodiment of the invention relates to a process for the preparation of a compound of formula XXXI, as hereinbefore defined, said process comprising:

(i) a process as hereinbefore defined for the preparation of a compound of formula XXV; followed by (ii) removal of the —Si($R^{s1}$)($R^{s2}$)($R^{s3}$) protecting group, for example under conditions known to those skilled in the art (e.g. by contacting the compound of formula XXV at ambient temperature with a mixture of an alkali metal hydroxide (such as KOH) and a $C_{1-4}$ alkyl alcohol, such as methanol).

In another further aspect of the invention, there is also provided a process for the preparation of a compound of formula XV, said process comprising:

(i) a process as hereinbefore defined for the preparation of a compound of formula XXXI; followed by (ii) esterification of the carboxylic acid with a source of the group $R^x$ (e.g. with $R^x$—OH or $R^x$—$N_2$ or, when $R^x$ represents $C_{1-4}$ alkyl, with $R^x$—I), for example under conditions known to those skilled in the art.

Moreover, in a still further aspect of the invention, there is provided a process for the preparation of a compound of formula I, as hereinbefore defined, said process comprising a process as hereinbefore defined for the preparation of a compound of formula XXV, XXXI or XV.

In the above aspects of the invention relating to the preparation of compounds of formulae XXV, XXXI and I, the following may apply:

$R^{s1}$ to $R^{s3}$ all represent the same $C_{1-4}$ alkyl group (e.g. $R^{s1}$ to $R^{s3}$ all represent a $C_{1-2}$ alkyl group, such as methyl); and/or $R^2$ and $R^3$ both represent $C_{1-3}$ alkyl (e.g. methyl).

The processes described herein involving the preparation of compounds of formula XXV provide the compound of formula XXXI (a useful intermediate in the synthesis of compounds of formula I) by a route that, compared to known processes, may possess (for example) one or more of the following advantages:

the use of fewer steps from readily available starting materials;

the use of readily available, cost-effective and/or environmentally friendly materials;

the provision of the product in a high percentage yield;

the provision of the product in a form that is easy to isolate (e.g. from any impurities); and/or the achievement of efficiency with regard to energy and/or solvents.

A further aspect of the invention relates to a compound of formula XXV, as hereinbefore defined, or a salt or protected derivative thereof. Protected derivatives of the compound of formula XXV include esters (e.g. $C_{1-4}$ alkyl esters) thereof. Particular compounds of formula XXV that may be mentioned include those in which $R^{s1}$ to $R^{s3}$, $R^2$ and $R^3$ take any of the definitions mentioned above for those groups (e.g. $R^{s1}$ to $R^{s3}$, $R^2$ and $R^3$ all represent methyl).

The other aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better stability (e.g. long term stability) than, or may have other useful pharmacological properties over, similar compounds, combinations, methods (treatments) or uses known in the prior art for use in the treatment of those conditions or otherwise.

The compounds of the invention may additionally (or alternatively):

exhibit a long duration of action and/or persistence of action (e.g. in comparison to other previously disclosed p38 MAP kinase inhibitors such as, for example, BIRB796);

not strongly inhibit GSK 3α (e.g. they may have an $IC_{50}$ against GSK 3α of 1500 nM or greater; such as 2,000, 3,000, 4,000, 5,000, 6,000, 7,000, 8,000, 9,000 or 10,000 nM or greater);

maintain a relatively high drug concentration between doses (e.g. a high concentration relative to other previously disclosed p38 MAP kinase inhibitors such as, for example, BIRB796);

establish and maintain a relatively high drug concentration in a target tissue following (e.g. topical) administration (e.g. a high concentration relative to other previously disclosed p38 MAP kinase inhibitors such as, for example, BIRB796);

exhibit properties that are particularly suited to topical/local administration (e.g. following topical/local administration, the generation of high target tissue concentrations but low plasma concentrations of the compounds of formula I and/or rapid clearance of the compounds of formula I from plasma);

have a reduced risk of extravascular exposure following intravenous administration (e.g. due to a low volume of distribution for the compounds of formula I);

exhibit superior potency with respect to selected kinases (e.g. Syk and/or a panel of kinases, such as Syk, Src and p38 MAPKα);

exhibit reduced β -catenin induction and/or inhibition of mitosis in cells;

exhibit no or less time-dependent inhibition of members of the cytochrome P450 superfamily; and/or produce less problematic (e.g. less toxic) metabolites, e.g. following administration to a patient.

EXPERIMENTAL METHODS

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Analytical Methods

Analytical HPLC was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV spectra of the eluted peaks were measured using either a diode array or variable wavelength detector on an Agilent 1100 system.

Analytical LCMS was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV and mass spectra of the eluted peaks were measured using a variable wavelength detector on either an Agilent 1100 with or an Agilent Infinity 1260 LC with 6120 quadrupole mass spectrometer with positive and negative ion electrospray.

Preparative HPLC was carried out using an Agilent Prep-C18 5 μm Preparative Cartridge using either a gradient of either 0.1% formic acid in MeCN in 0.1% aqueous formic acid or a gradient of MeCN in 10 mM Ammonium Bicarbonate; or a Waters Xselect CSH C18 μm column using a gradient 0.1% MeCN in 0.1% aqueous formic acid. Fractions were collected following detection by UV at 254 nm.

$^1$H NMR Spectroscopy: $^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

Preparation of 2,2-Dimethylbut-3-ynoic acid (i) 2-Methyl-4-(trimethylsilyl)but-3-yn-2-ol A solution of TMS-acetylene (40 g, 0.407 mol) in THF (200 mL) at −70° C. under $N_2$ was treated with 2.5 M nBuLi (163 mL, 0.407 mol) such that the temperature remained below −30° C. On complete addition the mixture was re-cooled to −70° C. and acetone (23.65 g, 0.407 mol) added dropwise keeping the temp <−50° C. The reaction mixture was allowed to warm to 10° C. and then added to aq. HCl and extracted into $Et_2O$. The organic layer was separated and washed with water, dried ($MgSO_4$) and concentrated under reduced pressure (water bath <40° C.) to give 2-methyl-4-(trimethylsilyl)but-3-yn-2-ol (70 g, quant.) as a pale yellow oil containing residual solvent (no effort was made to remove residual solvent due to volatility of the product).

(ii) (3-Chloro-3-methylbut-1-yn-1-yl)trimethylsilane

A mixture of 2-methyl-4-(trimethylsilyl)but-3-yn-2-ol (see step (i) above; 63 g, 0.403 mol) in 37% HCl (240 mL) was heated at reflux overnight. After cooling to room temperature the reaction mixture was added to ice and the product extracted into pentane. The organic extracts were dried ($MgSO_4$), filtered through a silica plug, and cautiously concentrated under reduced pressure to give (3-chloro-3-methylbut-1-yn-1-yl)trimethylsilane (58.9 g, 83% over two steps) as a colourless oil.

(iii) 2,2-Dimethyl-4-(trimethylsilyl)but-3-ynoic acid

Pre-ground (mortar and pestle) magnesium turnings (4.1 g, 0.172 mol) were charged to a 3-neck flask containing THF (75 mL). The mixture was stirred under $N_2$ at room temperature whilst ~3 g of (3-chloro-3-methylbut-1-yn-1-yl)trimethylsilane (see step (ii) above) was added. Once initiation of reaction was observed (exotherm!) the remaining (3-chloro-3-methylbut-1-yn-1-yl)trimethylsilane (12 g; reaction total 15 g, 0.086 mol) was added with cooling so as to keep the temperature in the range 15-22° C. The reaction mixture was stirred at room temperature for a further 1 hour before being added to solid $CO_2$ (150 g). After 1 hour, when there was no longer any solid $CO_2$ present, water was added and the mixture made acidic with HCl. The mixture was extracted with $Et_2O$, the organic extracts dried ($MgSO_4$) and concentrated under reduced pressure to give 2,2-dimethyl-4-(trimethylsilyl)but-3-ynoic acid (15.86 g, 100%) as a yellow oil that solidified on cooling.

(iv) 2,2-Dimethylbut-3-ynoic acid

A mixture of 2,2-dimethyl-4-(trimethylsilyl)but-3-ynoic acid (15.86 g, 0.086 mol) and KOH (12.51 g, 0.223 mol) in methanol (150 mL) was stirred for 1 hour and then concentrated under reduced pressure. The residue was diluted with water and acidified with HCl. The mixture was extracted with Et$_2$O, the organic extracts dried (MgSO$_4$) and concentrated under reduced pressure to give 2,2-dimethylbut-3-ynoic acid (9.1 g, 94%) as a yellow oil.

Preparation of Compounds of the Invention

Example 1

1-(3-(2-Methylbut-3-yn-2-yl)-1-(p-tolyl)-1H-pyrazol-5-yl)-3-(4-((2-(phenylamino)pyrimidin-4-yl)oxy)naphthalen-1-yl)urea

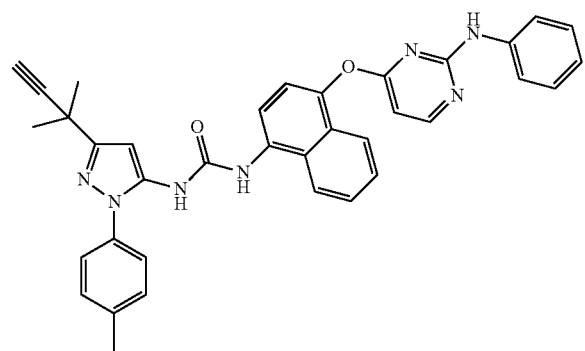

(i) 4-((4-Aminonaphthalen-1-yl)oxy)-N-phenylpyrimidin-2-amine p-TSA monohydrate (2.80 g, 14.72 mmol) was added to a stirred mixture of 4-((2-chloropyrimidin-4-yl)oxy)naphthalen-1-amine (see, for example, Cirillo, P. F. et al., WO 2002/92576, 21 Nov. 2000; 8 g, 29.4 mmol) and aniline (6.71 mL, 73.6 mmol) in THF (50 mL) at rt under N$_2$. The mixture was heated under reflux for 2 h (reaction mixture solidified), a further 50 ml of THF was added and the mixture heated for a further 2 h. The mixture was cooled, diluted with THF (200 mL), the solid filtered and washed with THF (150 mL). The solid was suspended in DCM (100 mL) and 2M NaOH (35 mL) and the mixture stirred vigorously for 1 h, during which time the solid dissolved. The organic layer was separated, the aq. layer extracted with DCM (100 mL) and the organics combined, dried (MgSO$_4$) and evaporated under reduced pressure. The residue was triturated with ether and filtered to give the sub-title compound (4.18 g).

1H NMR (400 MHz; DMSO-d6) δ 9.46 (s, 1H), 8.32 (d, 1H), 8.18-8.15 (m, 1H), 7.64-7.62 (m, 1H), 7.45-7.40 (m, 2H), 7.35 (d, 2H), 7.11 (d, 1H), 7.03-6.99 (m, 2H), 6.80 (t, 1H), 6.72 (d, 1H), 6.42 (d, 1H), 5.79 (s, 2H).

LCMS m/z 329 (M+H)$^+$ (ES$^+$)

(ii) 4,4-Dimethyl-3-oxohex-5-ynenitrile

A mixture of methyl 2,2-dimethylbut-3-ynoate (1.10 g, 7.85 mmol) and acetonitrile (0.716 mL, 13.73 mmol) was added dropwise to a stirred, refluxing mixture of NaH, 60% dispersion in mineral oil (0.706 g, 17.66 mmol) in THF (65 mL). The mixture was stirred at reflux for 2 hours. The mixture was carefully concentrated under reduced pressure and resuspended in diethyl ether (25 mL). The ether layer was steadily treated with water (25 mL) and stirred. Once the quench and effervescence had subsided the organic phase was separated. The aqueous layer was acidified with 1 M hydrogen chloride (20 mL) and extracted with diethyl ether (3×25 mL). The combined organic phases were washed with saturated brine (25 mL) and dried (MgSO$_4$). The solvent was removed under reduced pressure to yield the sub-title compound (950 mg).

1H NMR (400 MHz; CDCl$_3$) δ 3.96 (s, 2H), 2.45 (s, 1H), 1.44 (s, 6H).

(iii) 3-(2-Methylbut-3-yn-2-yl)-1-(p-tolyl)-1H-pyrazol-5-amine p-Tolylhydrazine, HCl (725 mg, 4.52 mmol) and the product from step (ii) above (979 mg, 5.43 mmol) were heated to reflux in ethanol (15 mL) for 4 h. The mixture was concentrated under reduced pressure to yield a brown solid. Saturated NaHCO3 (15 mL) and water (5 mL) were added and the mixture was extracted with diethyl ether (3×15 mL). The combined organic phases were concentrated to dryness on silica gel. The pre-adsorbed silica was purified by chromatography on the Companion (40 g column, 0-20% ethyl acetate:hexanes) to afford the sub-title compound (533 mg) as a dark brown oil which crystallised on standing.

LCMS m/z 240 (M+H)$^+$ (ES$^+$)

(iv) 1-(3-(2-Methylbut-3-yn-2-yl)-1-(p-tolyl)-1H-pyrazol-5-yl)-3-(4-((2-(phenylamino)-pyrimidin-4-yl)oxy)naphthalen-1-yl)urea The product from step (iii) above (134 mg, 0.560 mmol) and CDI (100 mg, 0.616 mmol) were stirred in DCM (1 mL) overnight. The mixture was concentrated under reduced pressure before adding a solution of the product from step (i) above (184 mg, 0.560 mmol) in THF (2 mL) and stirring at rt for 4 h. The mixture was concentrated under reduced pressure and the residue was triturated in MeCN to yield 180 mg of cream solid. The solid was purified by chromatography on silica gel (12 g column, 10-50% ethyl acetate/isohexane to afford the product as a cream solid. The solid was co-evaporated with DCM, triturated in methanol then recrystallised in acetonitrile to yield the title compound (96 mg) as a white solid.

1HNMR (400 MHz; DMSO-d6) δ 9.50 (s, 1H), 9.18 (s, 1H), 8.83 (s, 1H), 8.40 (d, 1H), 8.09 (d, 1H), 7.95 (d, 1H), 7.82 (d, 1H), 7.63 (t, 1H), 7.56 (t, 1H), 7.49 (d, 2H), 7.41 (d, 3H), 7.34-7.17 (m, 1H), 6.97 (t, 2H), 6.78 (t, 1H), 6.58 (d, 1H), 6.55 (s, 1H), 3.11 (s, 1H), 2.42 (s, 3H), 1.57 (s, 6H).

LCMS m/z 594 (M+H)$^+$ (ES$^+$); 592 (M−H)$^-$ (ES$^-$)

Example 2

1-(4-((2-((7-Methyl-1H-indazol-5-yl)amino)pyrimidin-4-yl)oxy)naphthalen-1-yl)-3-(3-(2-methylbut-3-yn-2-yl)-1-(p-tolyl)-1H-pyrazol-5-yl)urea

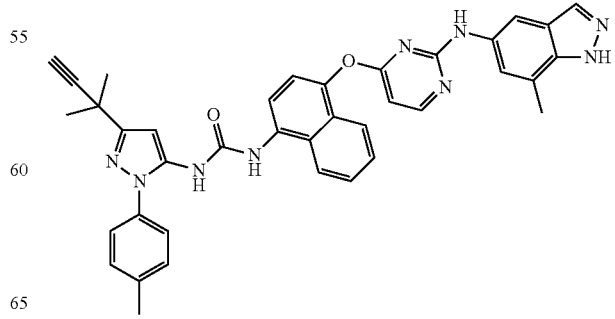

(i) Phenyl (4-((2-chloropyrimidin-4-yl)oxy)naphthalen-1-yl)carbamate

Phenyl chloroformate (2.65 ml, 21.06 mmol) was added to a stirred mixture of 4-((2-chloropyrimidin-4-yl)oxy)naphthalen-1-amine (see, for example, Cirillo, P. F. et al., WO 2002/92576, 21 Nov. 2000; 5.45 g, 20.06 mmol) and sodium bicarbonate (3.37 g, 40.1 mmol) in DCM (50 ml) and THF (20 ml) at rt. The mixture was stirred for 18 h then a further portion of phenyl chloroformate added (0.5 mL) and left for 2 h. The mixture was partitioned between DCM (300 mL) and brine (200 mL), the organic phase separated, dried (MgSO$_4$) and evaporated under reduced pressure. The residue was triturated with ether/isohexane to give the sub-title compound (7.38 g) as a light pink solid.

1H NMR (DMSO-d6) 400 MHz, δ: 10.28 (s, 1H), 8.68 (d, 1H), 8.29 (d, 1H), 7.84 (d, 1H), 7.76 (d, 1H), 7.72-7.68 (m, 1H), 7.64-7.60 (m, 1H), 7.51-7.44 (m, 3H), 7.33-7.26 (m, 4H).

LCMS m/z 392/4 (M+H)$^+$ (ES$^+$)

(ii) 1-(4-((2-Chloropyrimidin-4-yl)oxy)naphthalen-1-yl)-3-(3-(2-methylbut-3-yn-2-yl)-1-(p-tolyl)-1H-pyrazol-5-yl)urea DMAP (34.4 mg, 0.282 mmol) was added to a solution of 3-(2-methylbut-3-yn-2-yl)-1-(p-tolyl)-1H-pyrazol-5-amine (see Example 1(iii) above; 337 mg, 1.408 mmol) and the product from step (i) above (579 mg, 1.479 mmol) in anhydrous THF (600 μL) and the reaction heated at 50° C. for 16 h. After this time the reaction was cooled to ambient temperature and solvent was removed under reduced pressure to afford a brown oil. The crude product was purified by chromatography on the Companion (40 g column, 0-5% MeOH in DCM) to afford crude product as a dark brown solid. This was repurified by chromatography on silica gel (12 g column, 0-30% ethyl acetate in toluene) to afford the sub-title compound (475 mg) as a pale brown solid.

1H NMR (400 MHz; DMSO-d6) δ 9.17 (s, 1H), 8.86 (s, 1H), 8.66 (d, 1H), 8.09 (d, 1H), 7.97 (d, 1H), 7.80 (dd, 1H), 7.66 (ddd, 1H), 7.58 (ddd, 1H), 7.50-7.45 (m, 2H), 7.45-7.37 (m, 3H), 7.27 (d, 1H), 6.54 (s, 1H), 3.09 (s, 1H), 2.41 (s, 3H), 1.56 (s, 6H).

LCMS m/z 537/9 (M+H)$^+$ (ES$^+$); 535/7 (M−H)$^−$ (ES$^−$)

(iii) 1-(4-((2-((7-Methyl-1H-indazol-5-yl)amino)pyrimidin-4-yl)oxy)naphthalen-1-yl)-3-(3-(2-methylbut-3-yn-2-yl)-1-(p-tolyl)-1H-pyrazol-5-yl)urea To a solution of the product from step (ii) above (125 mg, 0.233 mmol) in DMF (2 mL) and THF (1 mL) was added p-TSA (44.3 mg, 0.233 mmol) followed by 7-methyl-1H-indazol-5-amine, HCl (85 mg, 0.466 mmol) and the reaction heated at 60° C. for 22 h. After this time the reaction was cooled to ambient temperature, and partitioned between ethyl acetate (40 mL) and sat. aqueous NaHCO$_3$ (20 mL). The organic phase was washed with water (20 mL) and saturated brine (20 mL). The organic layer was dried over MgSO$_4$, filtered and concentrated in vacuo to afford a pale brown solid. The crude product was dry loaded onto silica and purified by chromatography on silica gel (12 g column, 0-60% EtOAc in toluene) to afford a pale tan powder. The material was further purified by chromatography on silica gel (4 g column (dry loaded), 0-25% (MeOH/1N NH$_3$) in DCM) to afford the title compound (23 mg) as a pale orange solid.

1H NMR (400 MHz; DMSO-d6) δ 12.84 (s, 1H), 9.43 (s, 1H), 9.23 (s, 1H), 8.91 (s, 1H), 8.38 (d, 1H), 8.15-8.04 (m, 2H), 7.83 (dd, 1H), 7.66-7.48 (m, 5H), 7.45-7.29 (m, 4H), 7.02 (br. s, 1H), 6.59-6.54 (m, 2H), 3.09 (s, 1H), 2.41 (s, 3H), 2.29 (s, 3H), 1.57 (s, 6H).

LCMS m/z 648 (M+H)$^+$ (ES$^+$)

Example 3

1-(3-(2-Methylbut-3-yn-2-yl)-1-(p-tolyl)-1H-pyrazol-5-yl)-3-(4-((2-((2-oxoindolin-6-yl)amino)pyrimidin-4-yl)oxy)naphthalen-1-yl)urea

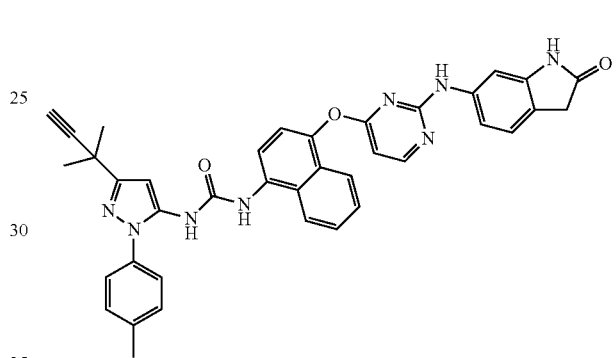

To a solution of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 254 mg, 0.473 mmol) in DMF (4 mL) and THF (2 mL) was added p-TSA monohydrate (90 mg, 0.473 mmol) followed by 6-aminoindolin-2-one (140 mg, 0.946 mmol) and the reaction heated at 60° C. for 22 h. The reaction mixture was partitioned between ethyl acetate (20 mL) and sat. aqueous sodium bicarbonate (10 mL). The organic layer was taken, dried over MgSO4, filtered and concentrated under reduced pressure to afford 150 mg of a brown solid. The MgSO4 was washed with 10% MeOH/DCM (50 mL) and the washings concentrated under reduced pressure to afford a pale yellow powder which was purified by chromatography on the Companion (12 g column, 0-10% MeOH in DCM) to afford the title compound (50 mg) as a pale yellow powder.

1H NMR (400 MHz; DMSO-d6) δ: 10.19 (s, 1H), 9.49 (s, 1H), 9.16 (s, 1H), 8.82 (s, 1H), 8.37 (d, 1H), 8.07 (d, 1H), 7.93 (d, 1H), 7.82 (dd, 1H), 7.63 (ddd, 1H), 7.56 (ddd, 1H), 7.50-7.46 (m, 2H), 7.43-7.38 (m, 3H), 7.14 (br. s, 1H), 6.95 (br. dd, 1H), 6.79 (br. dd, 1H), 6.56 (s, 1H), 6.49 (d, 1H), 3.30 (s, 2H), 3.10 (s, 1H), 2.41 (s, 3H), 6.17 (s, 6H).

LCMS m/z 649 (M+H)$^+$ (ES$^+$); 647 (M−H)$^−$ (ES$^−$)

Example 4

3-Methoxy-5-((4-((4-(3-(3-(2-methylbut-3-yn-2-yl)-1-(p-tolyl)-1H-pyrazol-5-yl)ureido)-naphthalen-1-yl)oxy)pyrimidin-2-yl)amino)-N-(2-morpholinoethyl)benzamide

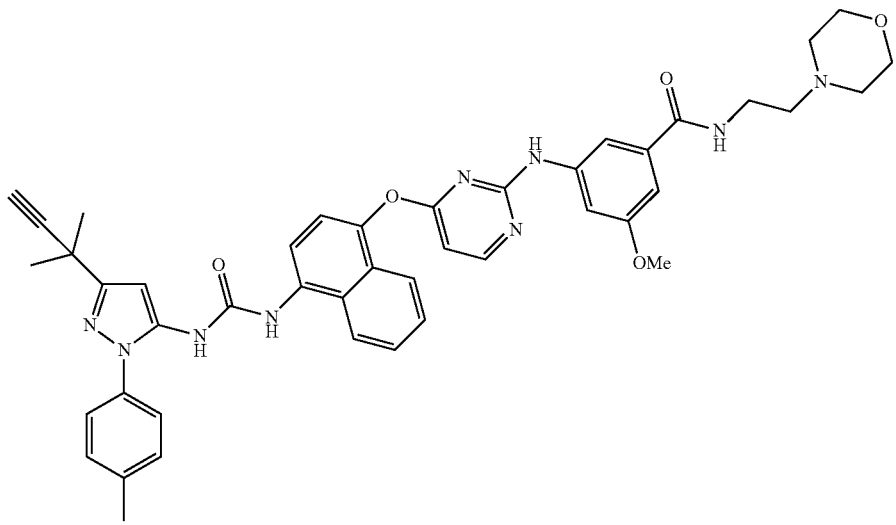 [SMILES: C#CC(C)(C)c1cc(NC(=O)Nc2ccc(Oc3ccnc(Nc4cc(OC)cc(C(=O)NCCN5CCOCC5)c4)n3)c3ccccc23)n(-c2ccc(C)cc2)n1]

(i) 3-Amino-5-methoxy-N-(2-morpholinoethyl)benzamide

To a stirred mixture of 3-amino-5-methoxybenzoic acid (5.20 g, 31.1 mmol), Et$_3$N (4.50 mL, 32.3 mmol) and 2-morpholinoethanamine (4.23 ml, 32.3 mmol) in THF (150 mL) and DMF (4 mL) was added HATU (14.72 g, 38.7 mmol) and the reaction stirred at ambient temperature overnight. After this time the mixture was taken up in ethyl acetate (300 mL) and washed with sat. NaHCO$_3$ (aq.) (2×100 mL). The aqueous was back extracted with further ethyl acetate (4×50 mL) and organics combined, dried over MgSO$_4$, filtered and concentrated under reduced pressure. Trituration with isohexanes (100 mL) afforded a pale orange gum (15 g). The crude product was purified by chromatography on the Companion (220 g column, 0-60% IPA in DCM). Fractions were combined as two separate batches to afford the sub-title compound (5.35 g) as an orange solid.

1H NMR (400 MHz; CDCl$_3$) δ: 6.69-6.64 (m, 3H), 6.35 (t, 1H), 3.81 (br. s, 2H), 3.81 (s, 3H), 3.73 (m, 4H), 3.53 (dd, 2H), 2.62-2.57 (m, 2H), 2.53-2.49 (m, 4H).

LCMS m/z 280 (M+H)$^+$ (ES$^+$)

(ii) 3-Methoxy-5-((4-((4-(3-(3-(2-methylbut-3-yn-2-yl)-1-(p-tolyl)-1H-pyrazol-5-yl)ureido)-naphthalen-1-yl)oxy)pyrimidin-2-yl)amino)-N-(2-morpholinoethyl)benzamide To a solution of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 150 mg, 0.251 mmol) and p-TSA monohydrate (47.8 mg, 0.251 mmol) in DMF (2 mL) and THF (1 mL) was added the product from step (i) above (146 mg, 0.497 mmol) and the reaction heated at 60° C. for 16 h. After this time further p-TSA monohydrate (100 mg, 0.526 mmol) was added and the reaction heated for a further 24 h. The reaction was then cooled to ambient temperature and partitioned between ethyl acetate (50 mL) and sat. aqueous NaHCO$_3$ (20 mL) and then the organic layer washed with water (20 mL), brine (20 mL) and then dried over MgSO$_4$, filtered and evaporated to give a brown oil (257 mg). The crude product was purified by chromatography on the Companion (40 g column, 0-5% MeOH/1M NH$_3$ in DCM) to afford an orange solid which was repurified by chromatography on silica gel (25 g column, 0-50% acetone in toluene) then by prep HPLC (Waters, Acidic (0.1% Formic acid), Waters X-Select Prep-C18, 5 µm, 19×50 mm column, 40-70% MeCN in Water) to afford the product as partial formate salts. The product was loaded onto a column of SCX (2 g) in MeOH (2 mL). The column was washed with MeOH (2 mL) and then the product was eluted with 0.7 M ammonia in MeOH (10 mL). The resultant mixture was concentrated in vacuo to afford the title compound (57 mg) as a pale yellow powder.

1H NMR (400 MHz; DMSO-d6) δ 9.59 (s, 1H), 9.13 (s, 1H), 8.84 (s, 1H), 8.41 (d, 1H), 8.17 (t, 1H), 8.07 (d, 1H), 7.95 (d, 1H), 7.82 (dd, 1H), 7.63 (ddd, 1H), 7.59-7.53 (m 2H), 7.50-7.45 (m, 2H), 7.42-7.37 (m, 3H), 7.32 (br. t, 1H), 6.85 (m, 1H), 6.55-6.52 (t, 2H), 3.58-3.53 (7H, m), 3.37-3.30 (2H, m), 3.10 (s, 1H), 2.46-2.36 (9H, m), 1.56 (s, 6H).

LCMS m/z 780 (M+H)$^+$ (ES$^+$); 778 (M−H)$^−$ (ES$^−$)

Example 5

1-(3-(2-Methylbut-3-yn-2-yl)-1-(p-tolyl)-1H-pyrazol-5-yl)-3-(4-((2-((3-(2-morpholinoethoxy)phenyl)amino)pyrimidin-4-yl)oxy)naphthalen-1-yl)urea

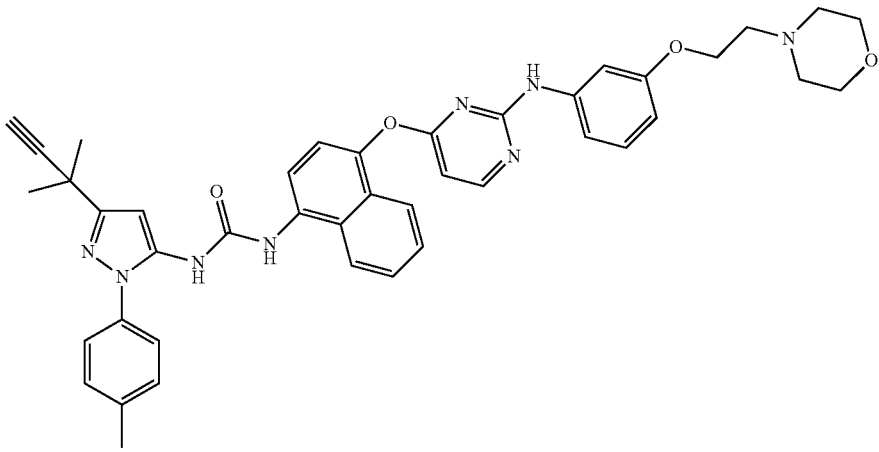 [SMILES: C#CC(C)(C)c1cc(NC(=O)Nc2ccc(Oc3ccnc(Nc4cccc(OCCN5CCOCC5)c4)n3)c3ccccc23)n(-c2ccc(C)cc2)n1]

To a solution of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 100 mg, 0.168 mmol) and p-TSA monohydrate (31.9 mg, 0.168 mmol) in DMF (2 mL) and THF (1 mL) was added 3-(2-morpholinoethoxy)aniline (74.5 mg, 0.335 mmol) and the reaction heated at 60° C. for 16 h. After this time further p-TSA monohydrate (63.8 mg, 0.335 mmol) was added and the reaction heated for a further 24 h.

The reaction was then cooled to ambient temperature and partitioned between ethyl acetate (50 mL) and sat. aqueous NaHCO₃ (20 mL) and then the organic layer washed with water (20 mL), brine (20 mL), dried over MgSO₄, filtered and evaporated to give a brown oil. The crude product was purified by chromatography on the Companion (40 g column, 0-4% MeOH/1M NH₃ in DCM) to an orange solid which was purified by chromatography on silica (25 g column, 0-40% acetone in toluene) to afford a pale yellow solid (102 mg). Trituration with ether (10 mL) afforded an off white solid, 47 mg, the ether washes were shown to contain product, 50 mg. as a clear oil. Both samples were purified by prep HPLC: (Waters, Acidic (0.1% Formic acid), Waters X-Select Prep-C18, 5 µm, 19×50 mm column, 40-70% MeCN in Water) to afford the title compound (22 mg) as a pale yellow powder.

1H NMR (400 MHz; DMSO-d6) δ: 9.45 (s, 1H), 9.16 (s, 1H), 8.83 (s, 1H), 8.39 (d, 1H), 8.07 (br. d, 1H), 7.96 (d, 1H), 7.82 (dd, 1H), 7.63 (ddd, 1H), 7.56 (ddd, 1H), 7.50-7.46 (m, 2H), 7.42-7.38 (m, 3H), 7.12 (br. s, 1H), 6.94 (br. d, 1H), 6.87 (br. t, 1H), 6.55 (t, 2H), 6.41 (dd, 1H), 3.90 (t, 2H), 3.54 (br. dd, 4H), 3.10 (s, 1H), 2.60 (t, 2H), 2.44-2.39 (m, 7H), 1.56 (s, 6H).

LCMS m/z 723 (M+H)⁺ (ES⁺); 721 (M−H)⁻ (ES⁻)

Example 6

1-(4-((2-((3-(2-(Dimethylamino)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea

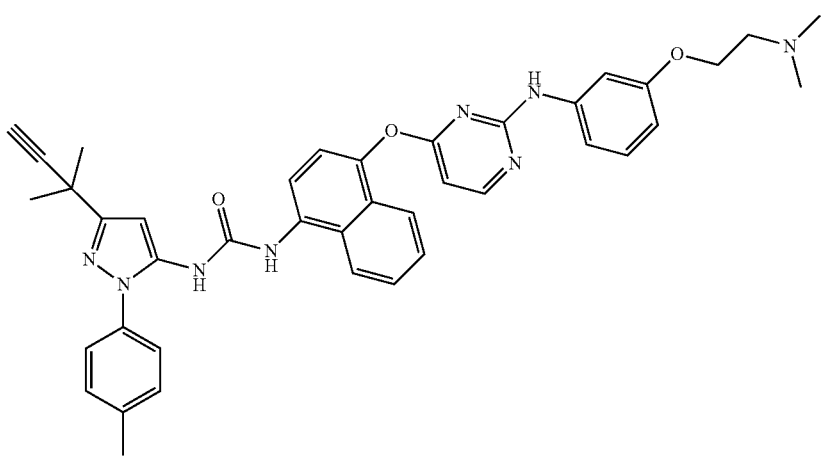 [SMILES: C#CC(C)(C)c1cc(NC(=O)Nc2ccc(Oc3ccnc(Nc4cccc(OCCN(C)C)c4)n3)c3ccccc23)n(-c2ccc(C)cc2)n1]

To a solution of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 200 mg, 0.335 mmol) and p-TSA monohydrate (191 mg, 1.006 mmol) in DMF (2 mL) and THF (3.5 mL) was added 3-(2-(dimethylamino)ethoxy)aniline (121 mg, 0.670 mmol) and the reaction heated at 60° C. for 16 h. After this time the reaction was diluted with ethyl acetate (20 mL) and washed with sat. aqueous NaHCO$_3$ (2×10 mL), brine (10 mL), dried over MgSO$_4$, filtered and concentrated under reduced pressure. The crude product was purified by chromatography on the Companion (40 g column, 0-10% 1N NH$_3$/MeOH in DCM) to afford crude product as a pale yellow solid which was purified by preparative HPLC (Waters, Acidic (0.1% Formic acid), Waters X-Select Prep-C18, 5 μm, 19×50 mm column, 25-60% MeCN in Water) to afford the desired product as a partial formate salt. The material was loaded in methanol (5 mL) onto SCX resin (1 g), washed with methanol (5 mL) and then eluted with 0.7 M NH$_3$ in methanol (10 mL). Solvent was removed under reduced pressure and the product dried under vacuum at 40° C. to afford the title compound (32 mg) as a pale yellow solid.

1H NMR (400 MHz; DMSO-d6) δ: 9.46 (s, 1H), 9.17 (s, 1H), 8.84 (s, 1H), 8.40 (d, 1H), 8.08 (br. dd, 1H), 7.96 (d, 1H), 7.82 (dd, 1H), 7.63 (ddd, 1H), 7.57 (ddd, 1H), 7.51-7.46 (m, 2H), 7.43-7.38 (m, 3H), 7.13 (br. s, 1H), 6.96 (br. d, 1H), 6.87 (t, 1H), 6.55 (t, 2H), 6.42 (dd, 1H), 3.87 (t, 2H), 3.11 (s, 1H), 2.55 (t, 2H), 2.42 (s, 3H), 2.17 (s, 6H), 1.57 (s, 6H)

LCMS m/z 681 (M+H)$^+$ (ES$^+$)

Example 7

1-(3-(2-Methylbut-3-yn-2-yl)-1-(p-tolyl)-1H-pyrazol-5-yl)-3-(4-((2-(phenylamino)pyridin-4-yl)oxy)naphthalen-1-yl)urea

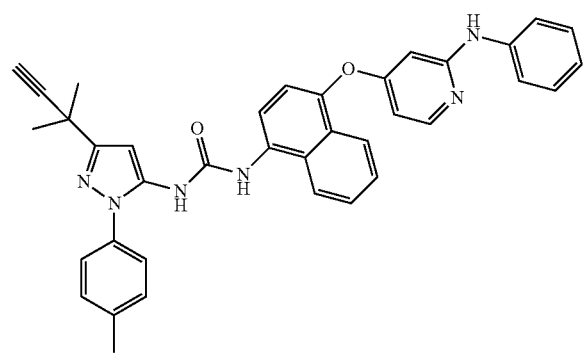 [SMILES: C#CC(C)(C)c1cc(NC(=O)Nc2ccc(Oc3ccnc(Nc4ccccc4)c3)c3ccccc23)n(-c2ccc(C)cc2)n1]

(i) 4-((4-Aminonaphthalen-1-yl)oxy)-N-phenylpyridin-2-amine

A mixture of 4-((2-chloropyridin-4-yl)oxy)naphthalen-1-amine (see, for example, Ito, K. et al., WO 2010/112936, 7 Oct. 2010; 600 mg, 2.216 mmol), aniline (619 mg, 6.65 mmol) and 4M HCl in dioxane (831 μL, 3.32 mmol) in NMP (6 mL) was heated at 140° C. for 18 h. The mixture was partitioned between EtOAc (150 ml) and aq. NaHCO$_3$ soln (50 mL), the organic layer separated, washed with 20% brine (100 mL), dried (MgSO$_4$) and evaporated under reduced pressure. The crude product was purified by chromatography on silica gel (80 g column, 0-30% EtOAc/isohexane) to afford a solid which was triturated with ether/isohexane, filtered and dried to afford the sub-title compound (328 mg).

1H NMR (400 MHz; CDCl$_3$) δ 7.97 (d, 1H), 7.87-7.83 (m, 2H), 7.54-7.46 (m, 2H), 7.28-7.21 (m, 4H), 7.05-6.99 (m, 2H), 6.90 (s, 1H), 6.74 (d, 1H), 6.38 (d, 1H), 6.31-6.29 (m, 1H), 4.11 (brs, 2H).

LCMS m/z 328 (M+H)$^+$ (ES$^+$)

(ii) Phenyl (4-((2-(phenylamino)pyridin-4-yl)oxy)naphthalen-1-yl)carbamate

Phenyl chloroformate (38 μL, 0.302 mmol) was added to a stirred mixture of sodium bicarbonate (46.2 mg, 0.550 mmol) and the product from step (i) above (90 mg, 0.275 mmol) in THF (0.6 mL) and DCM (1.5 mL) and the reaction stirred for 2 days at ambient temperature. After this time the reaction was partitioned between DCM (30 mL) and brine (20 mL), the organic phase separated, dried (MgSO$_4$) and evaporated under reduced pressure.

LCMS m/z 448 (M+H)$^+$ (ES$^+$)

(iii) 1-(3-(2-Methylbut-3-yn-2-yl)-1-(p-tolyl)-1H-pyrazol-5-yl)-3-(4-((2-(phenylamino)-pyridin-4-yl)oxy) naphthalen-1-yl) urea A solution of 3-(2-methylbut-3-yn-2-yl)-1-(p-tolyl)-1H-pyrazol-5-amine (see Example 1 (iii) above; 70 mg, 0.293 mmol), DMAP (5 mg, 0.041 mmol) and the product from step (ii) above (125 mg, 0.251 mmol) was heated in anhydrous THF (5 mL) at 50° C. for 22 h. The reaction was cooled, solvent removed under reduced pressure and the crude product dissolved in DCM (20 mL) and washed with water (10 mL). The DCM layer was isolated by passing the mixture through a phase separation cartridge and the solvent evaporated and the crude material purified by preparative HPLC (Waters, Acidic (0.1% Formic acid), Waters X-Select Prep-C18, 5 μm, 19×50 mm column, 30-70% MeCN in Water) to afford the title compound (0.3Formic Acid present) (23 mg) as a white powder.

1H NMR (400 MHz; DMSO-d6) δ: 9.22 (s, 1H), 8.89 (d, 2H), 8.25 (s, 0.3H), 8.12-8.05 (m, 2H), 7.95 (d, 1H), 7.85 (dd, 1H), 7.65 (ddd, 1H), 7.61-7.56 (m, 3H), 7.50-7.45 (m, 2H), 7.42-7.34 (m, 2H), 7.35 (d, 1H), 7.22-7.15 (m, 2H), 6.86-6.80 (m, 1H), 6.55-6.51 (m, 2H), 6.08 (d, 1H), 3.09 (s, 1H), 2.41 (s, 3H), 1.56 (s, 6H).

LCMS 593 (M+H)$^+$ (ES+); 591 (M−H)$^−$ (ES$^−$)

Example 8

1-(4-((2-((3-Methoxy-5-(2-morpholinoethoxy)phenyl)amino)pyrimidin-4-yl)oxy)-naphthalen-1-yl)-3-(3-(2-methylbut-3-yn-2-yl)-1-(p-tolyl)-1H-pyrazol-5-yl)urea

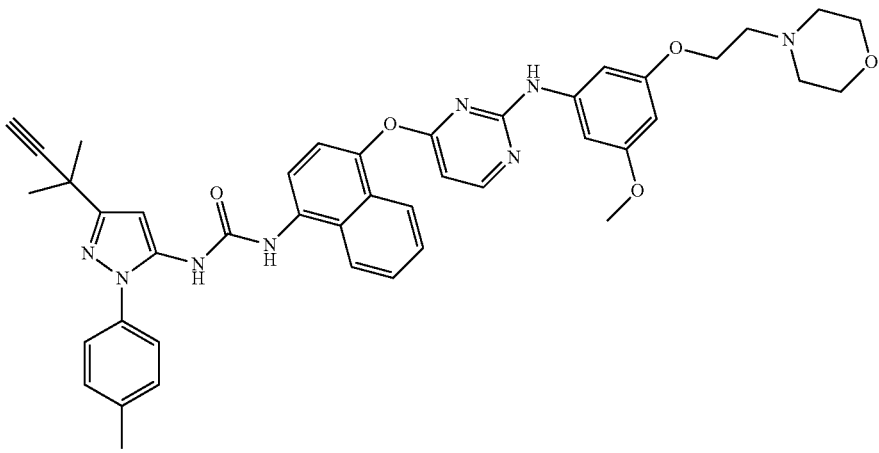 [SMILES: C#CC(C)(C)c1cc(NC(=O)Nc2ccc(Oc3ccnc(Nc4cc(OC)cc(OCCN5CCOCC5)c4)n3)c3ccccc23)n(-c2ccc(C)cc2)n1]

(i) 3-Methoxy-5-(2-morpholinoethoxy)aniline

The sub-title compound can be prepared according to or by analogy with procedures known to those skilled in the art and/or described herein. For example, the following procedure can be used.

To a stirred suspension of 3-amino-5-methoxyphenol (1.400 g, 10.06 mmol) and K$_2$CO$_3$ (6.95 g, 50.3 mmol) in pyridine/DMF (18 mL, 1:3) was added 4-(2-chloroethyl)morpholine hydrochloride (1.872 g, 10.06 mmol). The resulting mixture was heated at 60° C. overnight. The reaction was cooled to rt, filtered and concentrated in vacuo to afford a brown oil. The crude product was purified by chromatography on silica gel (40 g column, 0-10% MeOH in DCM) to afford the sub-title compound (1700 mg) as a sticky, orange oil.

1H NMR (DMSO-d6) 400 MHz, δ: 5.75-5.73 (m, 2H) 5.67 (t, 1H) 5.05 (s, 2H) 3.94 (t, 2H) 3.61 (s, 3H) 3.58-3.55 (m, 4H) 2.62 (t, 2H) 2.45-2.43 (m, 4H).

LCMS m/z 253 (M+H)$^+$ (ES+)

(ii) 1-(4-((2-((3-Methoxy-5-(2-morpholinoethoxy)phenyl)amino)pyrimidin-4-yl)oxy)-naphthalen-1-yl)-3-(3-(2-methylbut-3-yn-2-yl)-1-(p-tolyl)-1H-pyrazol-5-yl)urea To a solution of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 250 mg, 0.419 mmol) and 3-methoxy-5-(2-morpholinoethoxy)aniline (see step (i) above; 147 mg, 0.583 mmol) in DMF (2 mL) and THF (3.5 mL) was added p-TSA monohydrate (159 mg, 0.838 mmol) and the reaction heated at 60° C. for 24 h.

After this the reaction was diluted with ethyl acetate (20 mL) and washed with sat. aqueous NaHCO$_3$ (2×20 mL), brine (10 mL) and the organic layer dried over MgSO$_4$, filtered and concentrated under reduced pressure to afford 110 mg crude material as a brown oil. The crude product was purified by chromatography on silica gel (40 g column, 0-10% ethanol in toluene containing 1% triethylamine) to afford crude product. This was loaded onto a column of SCX (1 g) in MeOH-DCM 2:1, (1 mL). The column was washed with MeOH (10 mL) and DCM (10 mL) and then the product was eluted with 0.7 M ammonia in MeOH. The resultant mixture was concentrated in vacuo, triturated with 3:1 ether-isohexanes (10 mL), filtered and then passed through SCX column as before to afford the title compound (80 mg) as a pale yellow solid.

1H NMR (400 MHz; DMSO-d6) δ: 9.39 (s, 1H), 9.12 (s, 1H), 8.83 (s, 1H), 8.39 (d, 1H), 8.07 (br. d, 1H), 7.97 (d, 1H), 7.82 (dd, 1H), 7.63 (ddd, 1H), 7.57 (ddd, 1H), 7.49-7.45 (m, 2H), 7.42-7.37 (m, 3H), 6.78 (br. d, 2H), 6.55-6.51 (m, 2H)), 6.03 (t, 1H), 3.88 (t, 2H), 3.57-3.47 (m, 7H), 3.09 (s, 1H), 2.59 (t, 2H), 2.43-2.38 (m, 7H), 1.56 (s, 6H).

LCMS 753 (M+H)$^+$ (ES$^+$); 751 (M–H)$^-$ (ES$^-$)

Example 9

1-(2,3-Dichloro-4-((2-((7-methyl-1H-indazol-5-yl)amino)pyrimidin-4-yl)oxy)phenyl)-3-(3-(2-methylbut-3-yn-2-yl)-1-(p-tolyl)-1H-pyrazol-5-yl)urea

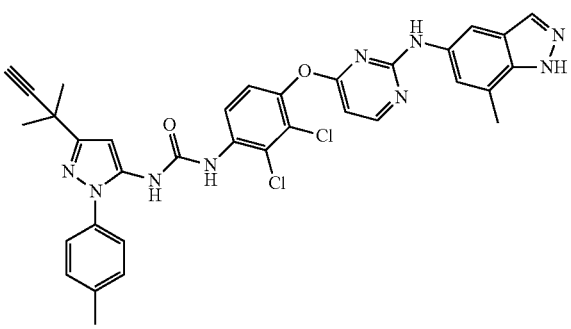 [SMILES: C#CC(C)(C)c1cc(NC(=O)Nc2ccc(Oc3ccnc(Nc4cc(C)c5[nH]ncc5c4)n3)c(Cl)c2Cl)n(-c2ccc(C)cc2)n1]

(i) 2,3-Dichloro-4-((2-chloropyrimidin-4-yl)oxy) aniline

DBU (11.85 mL, 79 mmol) was added over 5 min to a stirred mixture of 4-amino-2,3-dichlorophenol (10 g, 56.2 mmol) in MeCN (150 mL) at 0-5° C. After stirring for 5 min, 2,4-dichloropyrimidine (8.95 g, 60.1 mmol) was added portionwise over 5 min then the mixture warmed to rt and stirred for 2 h. The solvent was evaporated under reduced pressure and the residue partitioned between ether (200 mL) and water (200 mL). The aqueous layer was extracted with ether (200 mL) then the combined organic layers washed with brine (200 mL), dried (MgSO$_4$), filtered through a pad of silica and evaporated under reduced pressure. The residue was triturated with ether-isohexane, filtered and dried to afford the sub-title compound (14.403 g) as a light brown solid.

1H NMR (CDCl$_3$) 400 MHz, δ: 8.45 (d, 1H), 6.96 (d, 1H), 6.84 (d, 1H), 6.73 (d, 1H), 4.22 (s, 2H).

LCMS 290/2/4 (M+H)$^+$ (ES$^+$)

(ii) Phenyl (3-(2-methylbut-3-yn-2-yl)-1-(p-tolyl)-1H-pyrazol-5-yl)carbamate To a stirred mixture of 3-(2-methylbut-3-yn-2-yl)-1-(p-tolyl)-1H-pyrazol-5-amine (see Example 1(iii) above; 526 mg, 2.198 mmol) and sodium bicarbonate (380 mg, 4.52 mmol) in anhydrous DCM (6 mL) and anhydrous THF (2 mL) was added phenyl chloroformate (305 μL, 2.418 mmol). After 2.5 h a further 0.1 eq of phenyl chloroformate (30 μL) was added and the reaction stirred a further hour. After this time the reaction was diluted with DCM (20 mL) and water (20 mL) and passed through a phase separation cartridge. Solvent was removed under reduced pressure to afford the sub-title compound (878 mg) as an orange oil.

LCMS 360 (M+H)$^+$ (ES$^+$); 358 (M−H)$^-$ (ES$^-$)

(iii) 1-(2,3-Dichloro-4-((2-chloropyrimidin-4-yl) oxy)phenyl)-3-(3-(2-methylbut-3-yn-2-yl)-1-(p-tolyl)-1H-pyrazol-5-yl)urea To the product from step (ii) above (787 mg, 2.19 mmol) and the product of step (i) above (636 mg, 2.190 mmol) in isopropyl acetate (15 mL) was added Et$_3$N (45.8 μL, 0.329 mmol) and the reaction heated at 60° C. over 16 h. The reaction was allowed to cool to ambient temperature and a white precipitate was removed by filtration. Filtrate was concentrated under reduced pressure and purified by chromatography on silica gel (40 g column, 2% Ethanol in toluene) to afford the sub-title compound (200 mg) as a pale brown powder (approx 65% purity).

LCMS 555/7 (M+H)$^+$ (ES$^+$); 553/5 (M−H)$^-$ (ES$^-$)

(iv) 1-(2,3-Dichloro-4-((2-((7-methyl-1H-indazol-5-yl)amino)pyrimidin-4-yl)oxy)phenyl)-3-(3-(2-methylbut-3-yn-2-yl)-1-(p-tolyl)-1H-pyrazol-5-yl)urea To a solution of the product from step (iii) above (200 mg, 0.234 mmol) and 7-methyl-1H-indazol-5-amine, HCl (86 mg, 0.468 mmol) and DMF (2 mL) was added p-TSA monohydrate (44.5 mg, 0.234 mmol) and the resulting solution heated at 60° C. for 20 h. After this time the reaction was diluted with ethyl acetate (50 mL) and washed with sat. aqueous NaHCO$_3$ (2×20 mL), brine (20 mL), dried over MgSO$_4$, filtered and concentrated under reduced pressure to afford a brown solid (210 mg). The crude product was purified by chromatography on the Companion (40 g column, 20-50% ethyl acetate in toluene) to afford a yellow powder (44 mg). The crude product was purified by preparative HPLC (Waters, Acidic (0.1% Formic acid), Waters X-Select Prep-C18, 5 μm, 19×50 mm column, 35-75% MeCN in Water) to afford the title compound (20 mg) as a white powder.

1H NMR (400 MHz; DMSO-d6) δ: 12.95 (s, 1H), 9.61 (br. s, 1H), 9.41 (s, 1H), 9.03 (s, 1H), 8.39 (dd, 1H), 8.25 (br. d, 1H), 7.68 (br. s, 1H), 7.60-7.35 (m, 6H), 7.11 (s, 1H), 6.58-6.50 (m, 2H), 3.11 (s, 1H), 2.40 (s, 3H), 2.36 (s, 3H), 1.55 (s, 6H).

LCMS 666 (M+H)$^+$ (ES$^+$); 664 (M−H)$^-$ (ES$^-$)

Example 10

1-(4-((2-((6-(2-(Dimethylamino)ethoxy)pyridin-2-yl) amino)pyrimidin-4-yl)oxy)naphthalen-1-yl)-3-(3-(2-methylbut-3-yn-2-yl)-1-(p-tolyl)-1H-pyrazol-5-yl) urea

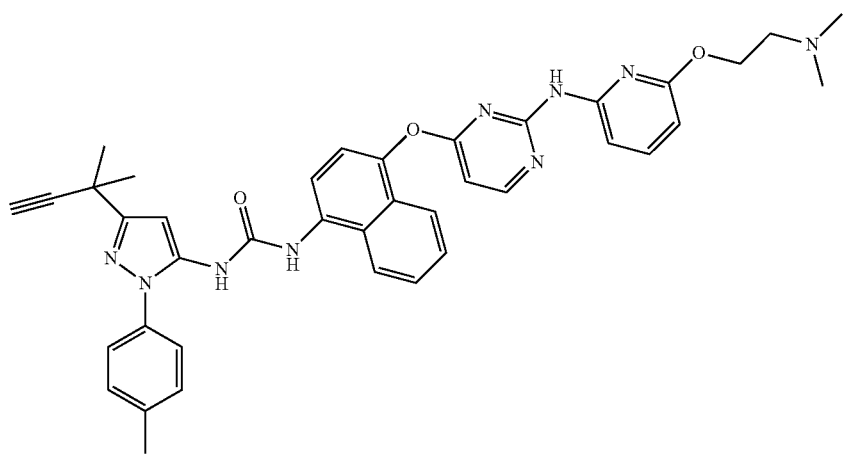 [SMILES: C#CC(C)(C)c1cc(NC(=O)Nc2ccc(Oc3ccnc(Nc4cccc(OCCN(C)C)n4)n3)c3ccccc23)n(-c2ccc(C)cc2)n1]

(i) 6-(2-(Dimethylamino)ethoxy)pyridin-2-amine 2-(Dimethylamino)ethanol (3.0 ml, 29.8 mmol) was treated with sodium (0.114 g, 4.98 mmol) in a sealed tube and stirred at ambient temperature until homogenous. 6-Chloropyridin-2-amine (1.1 g, 8.30 mmol) was added and the reaction mixture was heated to 145° C. and stirred in a microwave tube for 4 h. The reaction was cooled to rt then partitioned between EtOAc (50 mL) and water (30 mL). The aqueous phase was extracted with EtOAc (2×50 mL). The combined organic extracts were washed with brine (100 mL), dried (MgSO$_4$), filtered and concentrated in vacuo to afford an oil (1.28 g). The crude product was purified by chromatography on silica gel (40 g column, 0-10% MeOH/NH$_3$ in DCM) to afford the sub-title compound (791 mg) as a green oil.

1H NMR (DMSO-d6) 400 MHz, δ: 7.25 (t, 1H) 5.97 (d, 1H) 5.84 (d, 1H) 5.79 (br s, 2H) 4.19 (t, 2H) 2.54 (t, 2H) 2.18 (s, 6H).

LCMS 182 (M+H)$^+$ (ES$^+$)

(ii) 4-((4-Aminonaphthalen-1-yl)oxy)-N-(6-(2-(dimethylamino)ethoxy)pyridin-2-yl)pyrimidin-2-amine A 50 mL flask was charged tert-butyl (4-((2-chloropyrimidin-4-yl)oxy)naphthalen-1-yl)carbamate (see, for example, Ito, K. et al., WO 2010/067130, 17 Jun. 2010; 965 mg, 2.60 mmol), the product from step (i) above (588 mg, 3.24 mmol), Cs$_2$CO$_3$ (1269 mg, 3.89 mmol), BINAP (404 mg, 0.649 mmol) and Pd$_2$(dba)$_3$ (475 mg, 0.519 mmol). DMA (22 mL) was added and the mixture purged with nitrogen for 20 mins. The reaction was heated at 80° C. overnight. The reaction was cooled to rt. The crude product was loaded directly onto a column of SCX. The column was washed with MeOH and then the product was eluted with 1% NH$_3$ in MeOH. The product-containing fraction was concentrated in vacuo to afford crude product as a dark brown semi-solid (1.85 g). The crude product was dissolved in DCM (30 mL), TFA (10 mL, 130 mmol) was added and the reaction mixture stirred at rt for 3 h. The solvent was removed in vacuo and the resulting dark, brown residue dissolved in the minimum quantity of MeOH and loaded onto SCX. The column was eluted with MeOH followed by 1% NH$_3$ in MeOH. The filtrate was concentrated in vacuo to afford a dark brown oil (1.08 g). The crude product was purified by chromatography on silica gel (80 g column, 0-10% MeOH/NH$_3$ in DCM) to afford a dark brown oil (507 mg). 53% purity as assessed by 1H NMR. The product was used without further purification.

1H NMR (DMSO-d6) 400 MHz, δ: 9.40 (s, 1H) 8.38 (d, 1H) 8.18-8.13 (m, 1H) 7.63-7.59 (m, 1H) 7.44-7.40 (m, 2H) 7.15 (t, 1H) 7.11 (d, 1H) 7.00 (d, 1H) 6.71 (d, 1H) 6.50 (d, 1H) 6.24-6.22 (m, 1H) 5.81 (br s, 2H) 4.24 (t, 2H) 2.53 (t, 2H) 2.16 (s, 6H).

LCMS 417 (M+H)$^+$ (ES$^+$)

(iii) 1-(4-((2-((6-(2-(Dimethylamino)ethoxy)pyridin-2-yl)amino)pyrimidin-4-yl)oxy)-naphthalen-1-yl)-3-(3-(2-methylbut-3-yn-2-yl)-1-(p-tolyl)-1H-pyrazol-5-yl)urea To a stirred mixture of phenyl (3-(2-methylbut-3-yn-2-yl)-1-(p-tolyl)-1H-pyrazol-5-yl)carbamate (see Example 9(ii) above; 271 mg, 0.566 mmol) and the product from step (ii) above (445 mg, 0.566 mmol) in i-PrOAc (6 mL) was added triethylamine (12.23 µl, 0.088 mmol). The resulting mixture was heated at 70° C. for 30 mins. The reaction was cooled to rt then partitioned between EtOAc (40 mL) and brine (20 mL). The organic layer was washed with water (20 mL), dried (MgSO$_4$), filtered and concentrated in vacuo to afford a brown solid (630 mg). The crude product was purified by chromatography on silica gel (80 g column, 0-10% MeOH/NH$_3$ in DCM) to afford a foam (468 mg). The compound was dissolved in the minimum of MeOH and loaded onto SCX. The column was eluted with MeOH, the product eluted with 1% NH$_3$ in MeOH. The filtrate was concentrated in vacuo to afford an orange glass, which was triturated with isohexane/ether. The resulting solid was collected by filtration and washed with diethyl ether to afford the title compound (123 mg) as a beige solid.

1H NMR (DMSO-d6) 400 MHz, δ: 9.44 (s, 1H), 9.18 (s, 1H), 8.82 (s, 1H), 8.45 (d, 1H), 8.09 (d, 1H), 7.95 (d, 1H), 7.81 (d, 1H), 7.64-7.60 (m, 1H), 7.57-7.53 (m, 1H), 7.50-7.47 (m, 2H), 7.43-7.39 (m, 3H), 7.12 (t, 1H), 6.88 (d, 1H), 6.68 (d, 1H), 6.55 (s, 1H), 6.20 (d, 1H), 4.23 (t, 2H), 3.10 (s, 1H), 2.53 (t, 2H), 2.41 (s, 3H), 2.16 (s, 6H), 1.56 (s, 6H).

LCMS m/z 682 (M+H)$^+$ (ES$^+$); 680 (M−H)$^-$ (ES$^-$)

Example 11

1-(4-((2-((4-(2-(Dimethylamino)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea

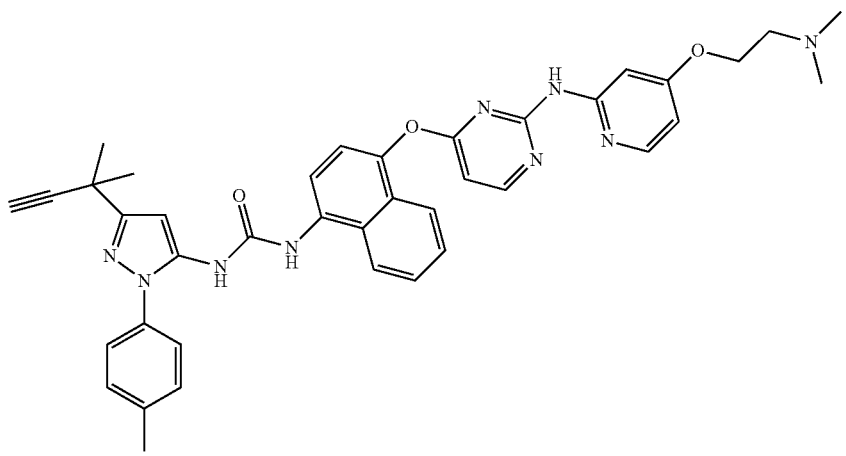 [SMILES: C#CC(C)(C)c1cc(NC(=O)Nc2ccc(Oc3ccnc(Nc4cc(OCCN(C)C)ccn4)n3)c3ccccc23)n(-c2ccc(C)cc2)n1]

(i) 4-(2-(Dimethylamino)ethoxy)pyridin-2-amine 2-(Dimethylamino)ethanol (3 mL, 29.8 mmol) was treated with sodium (343 mg, 14.91 mmol) in a sealed tube and heated at 80° C. until homogenous. 4-Chloropyridin-2-amine (1917 mg, 14.91 mmol) was added as a single portion and the reaction heated in a sealed tube at 145° C. for 1 h. The reaction was cooled to rt and partitioned between EtOAc (50 mL) and water (30 mL). The aqueous phase was extracted with EtOAc (2×50 mL). The combined organic extracts were washed with brine (100 mL), dried (MgSO$_4$), filtered and concentrated in vacuo to afford an oil. The crude product was purified by chromatography on silica gel (80 g column, 0-10% MeOH/NH$_3$ in DCM) to afford the sub-title compound (542 mg) as a white solid.

1H NMR (DMSO-d6) 400 MHz, δ: 7.70 (d, 1H) 6.11-6.09 (m, 1H) 5.94 (d, 1H) 5.74 (br s, 2H) 3.98 (t, 2H) 2.58 (t, 2H) 2.19 (s, 6H).

LCMS m/z 182 (M+H)$^+$ (ES$^+$)

(ii) 4-((4-Aminonaphthalen-1-yl)oxy)-N-(4-(2-(dimethylamino)ethoxy)pyridin-2-yl)pyrimidin-2-amine A 50 mL flask was charged tert-butyl (4-((2-chloropyrimidin-4-yl)oxy)naphthalen-1-yl)carbamate (see, for example, Ito, K. et al., WO 2010/067130, 17 Jun. 2010; 772 mg, 2.077 mmol), the product from step (i) above (470 mg, 2.60 mmol), caesium carbonate (1015 mg, 3.12 mmol), BINAP (323 mg, 0.519 mmol) and Pd$_2$(dba)$_3$ (380 mg, 0.415 mmol). DMA (15 mL) was added and the mixture purged with nitrogen for 20 mins. The reaction was heated at 80° C. overnight. The reaction was cooled to rt. The crude product was loaded directly onto a column of SCX in MeOH-DCM. The column was washed with MeOH and then the product was eluted with 1% NH$_3$ in MeOH. The product-containing fraction was concentrated in vacuo to afford crude product as a dark brown oil (1.66 g). The crude product was dissolved in DCM (25 mL). TFA (8 mL, 104 mmol) was added and the reaction mixture stirred at rt for 3 h. The solvent was removed in vacuo and the resulting dark, brown residue dissolved in the minimum quantity of MeOH and loaded onto SCX. The column was eluted with MeOH followed by 1% NH$_3$ in MeOH. The filtrate was concentrated in vacuo to afford a dark brown oil (890 mg). The crude product was purified by chromatography on silica gel (80 g column, 0-10% MeOH/NH$_3$ in DCM) to afford a dark brown oil (188 mg).

1H NMR (DMSO-d6) 400 MHz, δ: 9.59 (s, 1H) 8.36 (d, 1H) 8.16-8.12 (m, 1H) 8.00 (d, 1H) 7.65-7.62 (m, 1H) 7.56 (d, 1H) 7.46-7.40 (m, 2H) 7.14 (d, 1H) 6.68 (d, 1H) 6.53 (dd, 1H) 6.33 (d, 1H) 5.81 (s, 2H) 3.84 (t, 2H) 2.56 (t, 2H) 2.17 (s, 6H).

LCMS m/z 417 (M+H)$^+$ (ES$^+$)

(iii) 1-(4-((2-((4-(2-(Dimethylamino)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea Triethylamine (7.19 μl, 0.052 mmol) was added to a stirred mixture phenyl (3-(2-methylbut-3-yn-2-yl)-1-(p-tolyl)-1H-pyrazol-5-yl)carbamate (see Example 9(ii) above; 159 mg, 0.333 mmol) and the product from step (ii) above (169 mg, 0.333 mmol). The resulting mixture was heated at 70° C. for 30 min. The reaction was cooled to rt then partitioned between EtOAc (40 mL) and brine (20 mL). The organic layer was washed with water (20 mL), dried (MgSO$_4$), filtered and concentrated in vacuo to afford an orange/brown oil (440 mg). The crude product was purified by chromatography on silica gel (40 g column, 0-10% MeOH/NH$_3$ in DCM)) to afford a solid (287 mg) at ~86% purity. The solid was triturated with diethyl ether then MeCN to afford a white solid. The compound was dissolved in the minimum of MeOH and loaded onto SCX. The column was eluted with MeOH and the product eluted with 1% NH$_3$ in MeOH. The filtrate was concentrated in vacuo to afford an off-white solid, which was triturated with diethyl ether. The resulting solid was collected by filtration and washed with diethyl ether to afford the title compound (52 mg, 0.074 mmol, 22.2% yield) as a white solid.

1H NMR (DMSO-d6) 400 MHz, δ: 10.18 (br s, 1H), 9.42 (s, 1H), 9.14 (s, 1H), 8.52-8.51 (m, 1H), 8.21-8.16 (m, 2H), 7.97 (d, 1H), 7.83-7.81 (m, 1H), 7.66-7.62 (m, 1H), 7.60-7.56 (m, 1H), 7.51-7.44 (m, 3H), 7.42-7.27 (m, 3H), 6.87-6.63 (br m, 2H), 6.51 (s, 1H), 4.33 (br s, 2H), 3.53-3.45 (br m, 2H), 3.11 (s, 1H), 2.81 (s, 6H), 2.39 (s, 3H), 1.56 (s, 6H).

LCMS m/z 682 (M+H)$^+$ (ES$^+$); 680 (M−H)$^-$ (ES$^-$).

Example 12

3-((4-((4-(3-(3-(2-Methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethyl)benzamide

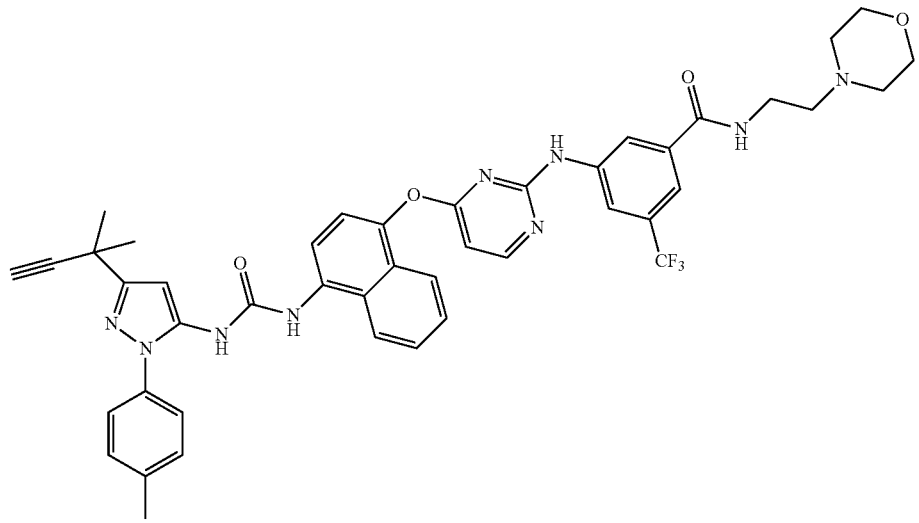 [SMILES: C#CC(C)(C)c1cc(NC(=O)Nc2ccc(Oc3ccnc(Nc4cc(C(=O)NCCN5CCOCC5)cc(C(F)(F)F)c4)n3)c3ccccc23)n(-c2ccc(C)cc2)n1]

(i) 3-Amino-N-(2-morpholinoethyl)-5-(trifluoromethyl)benzamide

To a stirred solution of 3-amino-5-(trifluoromethyl)benzoic acid (1.0 g, 4.87 mmol), 2-morpholinoethanamine (1.280 mL 9.75 mmol) and triethylamine (2.038 mL, 14.62 mmol) in DCM (20 mL) was added T3P (50 Wt % in EtOAc, 4.35 mL, 7.31 mmol) carefully, maintaining a temperature below 35° C. The reaction was stirred at rt for 1 h. The mixture was partitioned with sat. NaHCO$_3$ soln. (20 mL). The aqueous was separated and re-partitioned with fresh DCM (20 mL). The combined organics were washed with 20% w/w NaCl soln. (20 mL), dried (MgSO$_4$) filtered and concentrated in vacuo. The crude product was purified by chromatography on the Companion 40 g column, 2% MeOH:DCM to 5%) to afford the sub-title compound (1.43 g) as a yellow oil.

1H NMR (400 MHz; CDCl$_3$) δ 8.44 (t, 1H), 7.25 (m, 1H), 7.22 (m, 1H), 6.96 (s, 1H), 5.78 (s, 2H), 3.57 (t, 4H), 3.36 (q, 2H), 2.40-2.45 (m, 6H).

LCMS m/z 318.0 (M+H)$^+$ (ES$^+$)

(ii) 3-((4-((4-(3-(3-(2-Methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethyl)benzamide A suspension of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 115 mg, 0.193 mmol), the product from step (i) above (122 mg, 0.384 mmol) and p-TSA monohydrate (73 mg, 0.384 mmol) in THF/DMF (6 mL, 1:2) was heated at 60° C. for 72 h. The reaction was cooled to rt and partitioned between EtOAc (40 mL) and sat. aq. NaHCO$_3$ (30 mL). The aqueous layer was extracted with EtOAc (2×40 mL). The combined organic extracts were washed with water (2×50 mL), brine (2×50 mL), dried (MgSO$_4$), filtered and concentrated in vacuo to afford a foam. The crude product was purified by chromatography on silica gel (40 g column, 0-10% MeOH) to afford a pink solid, which was triturated with diethyl ether. The material was further purified by prep-HPLC affording the title compound (17 mg) as a white solid.

1H NMR (400 MHz; DMSO-d6) δ 9.99 (s, 1H), 9.26 (s, 1H), 8.99 (s, 1H), 8.54 (t, 1H), 8.48 (d, 1H), 8.28 (s, 1H), 8.12 (s, 1H), 8.08 (d, 1H), 7.94 (d, 1H), 7.82 (d, 1H), 7.55-7.65 (m, 3H), 7.49 (d, 2H), 7.39-7.43 (m, 3H), 6.65 (d, 1H), 6.53 (s, 1H), 3.56 (t, 4H), 3.36-3.40 (m, 4H), 3.12 (s, 1H), 2.41-2.47 (m, 7H), 1.56 (s, 6H).

LCMS m/z 409 (M+2H)$^{2+}$ (ES$^+$)

Example 13

1-(4-((2-((3-Methoxy-5-(2-(2-(2-methoxyethoxy)ethoxy)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea

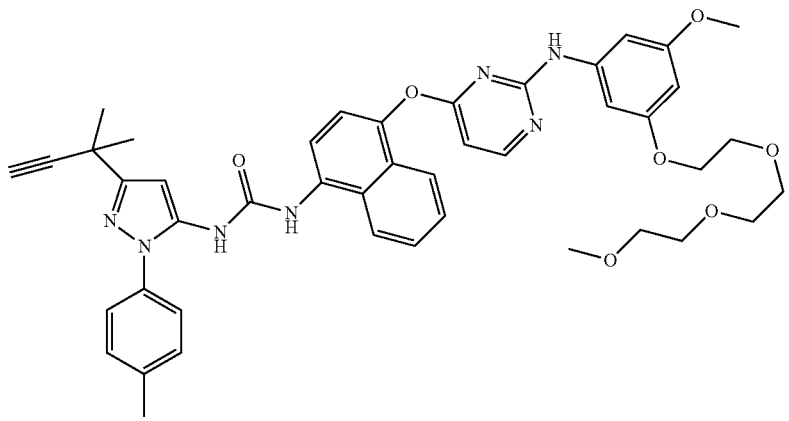 [SMILES: C#CC(C)(C)c1cc(NC(=O)Nc2ccc(Oc3ccnc(Nc4cc(OC)cc(OCCOCCOCCOC)c4)n3)c3ccccc23)n(-c2ccc(C)cc2)n1]

(i) 3-Methoxy-5-(2-(2-(2-methoxyethoxy)ethoxy)ethoxy)aniline

1-Bromo-2-(2-(2-methoxyethoxy)ethoxy)ethane (2.75 mL, 15.86 mmol) was added to a suspension of 3-amino-5-methoxyphenol (2 g, 14.37 mmol), potassium carbonate (6 g, 43.4 mmol) and sodium iodide (0.215 g, 1.437 mmol) in acetone (50 mL) and heated at reflux for 16 h. The mixture was partitioned between EtOAc (10 mL) and water (10 mL). The organic layer was separated washed with 20% w/w NaCl soln. (10 mL), dried (MgSO$_4$), filtered and evaporated. The crude product was purified by chromatography on silica gel (80 g column, 50% EtOAc:isohexane to 100%) to afford the sub-title compound (3.2 g) as a thick brown oil.

1H NMR (400 MHz, DMSO-d6) δ5.76-5.73 (m, 2H), 5.68 (t, 1H), 5.07 (s, 2H), 3.98-3.89 (m, 2H), 3.72-3.65 (m, 2H), 3.63 (s, 3H), 3.60-3.48 (m, 6H), 3.47-3.40 (m, 2H), 3.24 (s, 3H)

LCMS m/z 286 (M+H)$^+$ (ES$^+$)

(ii) tert-Butyl (4-((2-((3-methoxy-5-(2-(2-(2-methoxyethoxy)ethoxy)ethoxy)phenyl)amino)pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 1 g, 2.69 mmol), the product of step (i) above (1.15 g, 4.03 mmol) and p-TSA monohydrate (0.100 g, 0.526 mmol) in DMF (10 mL) was heated at 60° C. (block temperature, 55° C. internal temperature) for 14 h. The mixture was cooled and added dropwise to sat. aq. NaHCO$_3$ (100 mL) then partitioned with EtOAc (2×50 mL). Organics were bulked, washed with 20% w/w NaCl soln. (50 mL), dried (MgSO$_4$), filtered and solvent evaporated. The crude product was purified by chromatography on silica gel (40 g column) to afford the sub-title compound (1.14 g) as a clear brown oil.

1H NMR (400 MHz, DMSO-d6) δ 9.44 (s, 1H), 9.34 (s, 1H), 8.42 (d, 1H), 8.11 (d, 1H), 7.86-7.76 (m, 1H), 7.66-7.49 (m, 3H), 7.39 (d, 1H), 6.85 (s, 2H), 6.56 (d, 1H), 6.05 (t, 1H), 3.88 (dd, 2H), 3.71-3.63 (m, 2H), 3.59-3.48 (m, 9H), 3.46-3.38 (m, 2H), 3.22 (s, 3H), 1.52 (s, 9H)

LCMS m/z 621 (M+H)+ (ES+)

(iii) 4-((4-Aminonaphthalen-1-yl)oxy)-N-(3-methoxy-5-(2-(2-(2-methoxyethoxy)ethoxy)-ethoxy)phenyl)pyrimidin-2-amine TFA (2.8 mL, 36.3 mmol) was added dropwise to a stirred solution of the product of step (ii) above (1.1 g, 1.772 mmol) in DCM (5 mL). The reaction was stirred at rt for 2 h. The mixture was added dropwise to stirred water (10 mL) and 1M potassium carbonate solution (35 mL, 35.0 mmol) and stirring continued until effervescence ceased. The mixture was extracted with DCM (2×25 mL) then the combined organic phases were dried (MgSO4) and concentrated under reduced pressure. The crude product was purified by chromatography on silica gel (40 g column, 2% MeOH:DCM to 5%) to afford a brown gum that was recrystallised from isopropyl acetate (3 mL) afforded the sub-title compound (0.80 g) as a colourless solid.

1H NMR (400 MHz, DMSO-d6) δ 9.42 (s, 1H), 8.33 (d, 1H), 8.22-8.03 (m, 1H), 7.69-7.56 (m, 1H), 7.51-7.35 (m, 2H), 7.11 (d, 1H), 6.87 (d, 2H), 6.68 (d, 1H), 6.35 (d, 1H), 6.04 (t, 1H), 5.79 (s, 2H), 3.94-3.78 (m, 2H), 3.74-3.64 (m, 2H), 3.60-3.47 (m, 9H), 3.46-3.38 (m, 2H), 3.22 (s, 3H)

LCMS m/z 521 (M+H)+ (ES+)

(iv) 1-(4-((2-((3-Methoxy-5-(2-(2-(2-methoxyethoxy)ethoxy)ethoxy)phenyl)amino)-pyrimidin-4-yl)oxy)naphthalen-1-yl)-3-(3-(2-methylbut-3-yn-2-yl)-1-(p-tolyl)-1H-pyrazol-5-yl)urea Triethylamine (4 μL, 0.029 mmol) was added to a mixture of phenyl (3-(2-methylbut-3-yn-2-yl)-1-(p-tolyl)-1H-pyrazol-5-yl)carbamate (see Example 9(ii) above; 50 mg, 0.139 mmol) and the product of step (iii) above (73 mg, 0.140 mmol) in isopropyl acetate (2 mL) and the mixture heated at 50° C. for 4 h. The crude product was purified by chromatography on silica gel (12 g column, 1% MeOH:DCM to 4%) and the resultant solid triturated with Et2O (3×2 mL) to afford the title compound (48 mg) as a colourless solid.

1H NMR (400 MHz, DMSO-d6) δ 9.43 (s, 1H), 9.13 (s, 1H), 8.85 (s, 1H), 8.40 (d, 1H), 8.06 (d, 1H), 7.96 (d, 1H), 7.84-7.79 (m, 1H), 7.69-7.52 (m, 2H), 7.51-7.44 (m, 2H), 7.44-7.34 (m, 3H), 6.90-6.69 (m, 2H), 6.60-6.47 (m, 2H), 6.03 (t, 1H), 3.91-3.80 (m, 2H), 3.68-3.60 (m, 2H), 3.58-3.45 (m, 9H), 3.44-3.37 (m, 2H), 3.21 (s, 3H), 3.11 (s, 1H), 2.41 (s, 3H), 1.56 (s, 6H)

LCMS m/z 786 (M+H)+ (ES+)

Example 14

3-((4-((4-(3-(3-(2-Methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethoxy)benzamide

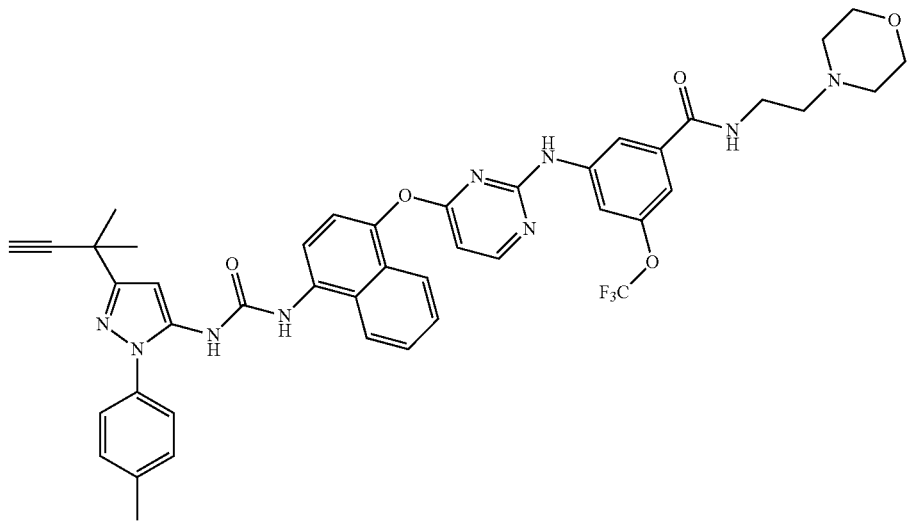 [SMILES: C#CC(C)(C)c1cc(NC(=O)Nc2ccc(Oc3ccnc(Nc4cc(OC(F)(F)F)cc(C(=O)NCCN5CCOCC5)c4)n3)c3ccccc23)n(-c2ccc(C)cc2)n1]

(i) 3-Amino-5-(trifluoromethoxy)benzoic acid

A mixture of 3-bromo-5-(trifluoromethoxy)benzoic acid (0.5 g, 1.754 mmol), sodium azide (0.303 g, 4.66 mmol), N1,N2-dimethylethane-1,2-diamine (0.062 g, 0.702 mmol), copper(I) iodide (0.067 g, 0.351 mmol) and K3PO4 (0.819 g, 3.86 mmol) in DMF (5 mL) was heated at 135° C. for 18 h. The mixture was cooled, EtOAc (20 mL) and Celite (2 g) was added then filtered. The filtrate was evaporated under reduced pressure to give a black oil. Repeat in duplicate. The crude product was loaded onto a column of SAX (Discovery® DSC-SAX, a polymer-bound quaternary amine) in MeOH. The column was washed with MeOH and then the product was eluted with 5% AcOH in MeOH. The resultant mixture was concentrated in vacuo then loaded onto a column of SCX in MeOH. The column was washed with MeOH and then the product was eluted with 0.7 M ammonia in MeOH. The resultant mixture was concentrated in vacuo to afford the sub-title compound (450 mg) as a yellow powder.

1H NMR (400 MHz; DMSO-d6) δ 7.15 (s, 1H), 6.87 (s, 1H), 6.57 (s, 1H), 5.63 (br s, 2H)

LCMS m/z 222 (M+H)+ (ES+); 220 (M−H)− (ES−)

(ii) 3-Amino-N-(2-morpholinoethyl)-5-(trifluoromethoxy)benzamide

T3P (50% Wt in EtOAc) (1.8 mL, 3.02 mmol) was added over 1 min to a solution of the product of step (i) above (440 mg, 1.990 mmol), 2-morpholinoethanamine (520 µL, 3.96 mmol) and TEA (0.83 ml, 5.95 mmol) in DCM (10 mL). The mixture was stirred at rt for 1 h then partitioned with sat. aq. NaHCO₃ soln. (20 mL) and DCM (30 mL). The organic layer was separated, washed with brine (20 mL), dried (MgSO₄) and evaporated under reduced pressure. The crude product was purified by chromatography on silica gel (40 g column, 0-5% MeOH/DCM) to afford the sub-title compound (520 mg) as a white solid.

1H NMR (400 MHz; CDCl₃) 7.03 (s, 1H), 6.88 (s, 1H), 6.71 (s, 1H), 6.63 (s, 1H), 3.98 (s, 2H), 3.74-3.72 (m, 4H), 3.55-3.50 (m, 2H), 2.60 (t, 2H), 2.52-2.50 (m, 4H)

LCMS m/z 334 (M+H)⁺ (ES⁺)

(iii) 3-((4-((4-(3-(3-(2-Methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethoxy)benzamide A mixture of 1-(4-((2-chloropyrimidin-4-yl)oxy)naphthalen-1-yl)-3-(3-(2-methylbut-3-yn-2-yl)-1-(p-tolyl)-1H-pyrazol-5-yl)urea (see Example 2(ii) above; 115 mg, 0.214 mmol), the product of step (ii) above (143 mg, 0.428 mmol) and p-TSA monohydrate (62 mg, 0.326 mmol) in DMF (3 mL) were heated at 60° C. for 18 h. A further portion of p-TSA monohydrate (62 mg, 0.326 mmol) was added and the mixture heated for a further 18 h. The mixture was partitioned between EtOAc (50 mL) and aq. sat. NaHCO₃ (50 mL), the organic layer separated, washed with water (40 mL), dried (MgSO₄), filtered and evaporated under reduced pressure. The crude product was purified by chromatography on silica gel (40 g column, 0-5% MeOH/DCM) to afford the title compound (21 mg) as a solid.

1H NMR (400 MHz; DMSO-d6) δ 9.96 (s, 1H), 9.14 (s, 1H), 8.87 (s, 1H), 8.48 (d, 1H), 8.41 (t, 1H), 8.08 (d, 1H), 7.99 (d, 1H), 7.96 (s, 1H), 7.82 (d, 1H), 7.75 (s, 1H), 7.65-7.40 (m, 7H), 7.23 (s, 1H), 6.66 (d, 1H), 6.54 (s, 1H), 3.57-3.54 (m, 4H), 3.12 (s, 1H), 2.45-2.37 (m, 9H), 1.57 (s, 6H). (2H under H₂O peak)

LCMS m/z 834 (M+H)⁺ (ES⁺)

Example 15

3-Ethynyl-5-((4-((4-(3-(3-(2-methylbut-3-yn-2-yl)-1-(p-tolyl)-1H-pyrazol-5-yl)ureido) naphthalen-1-yl)oxy)pyrimidin-2-yl)amino)-N-(2-morpholinoethyl)benzamide

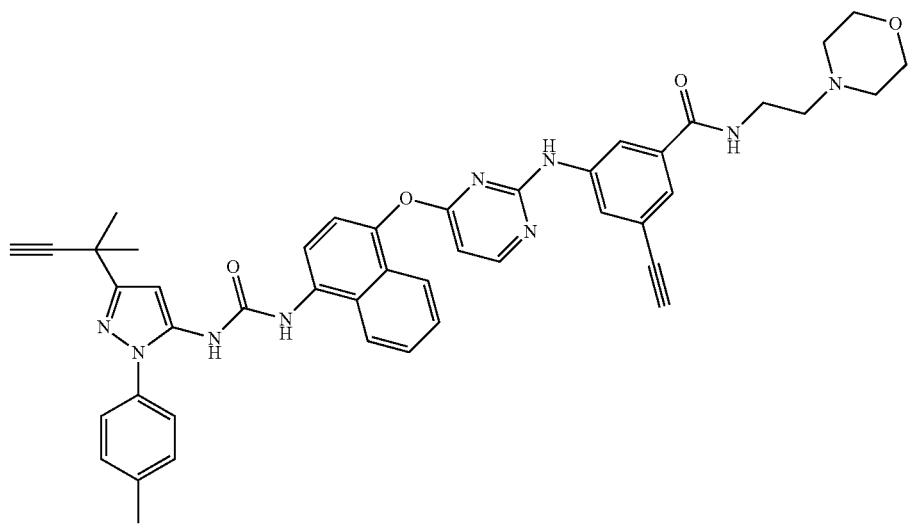 [SMILES: C#Cc1cc(Nc2nccc(Oc3ccc(NC(=O)Nc4cc(C(C)(C)C#C)nn4-c4ccc(C)cc4)c4ccccc34)n2)cc(C(=O)NCCN2CCOCC2)c1]

(i) 3-Amino-5-bromo-N-(2-morpholinoethyl)benzamide

T3P (50 Wt % in EtOAc, 56.2 mL, 94 mmol), was added carefully to a solution of 3-amino-5-bromobenzoic acid (13.6 g, 63.0 mmol), 2-morpholinoethanamine (16.52 mL, 126 mmol) and TEA (26.3 mL, 189 mmol) in DCM (200 mL). Ice bath used sporadically to prevent temperature rising above 35° C. Stirred at rt for 1 h then partitioned with sat. aq. NaHCO₃ soln. (250 mL). Aqueous separated and partitioned with fresh DCM (250 mL), organics separated, bulked and partitioned with 20% w/w NaCl soln. (250 mL). Organic layer was separated, dried (MgSO₄), filtered and solvent evaporated. The crude product was dissolved in DCM (100 mL) and the sub-title product (13 g) crystallised out on standing as a light tan crystalline solid.

1H NMR (400 MHz, DMSO-d6) δ 8.29 (t, 1H), 7.06 (t, 1H), 6.98 (t, 1H), 6.85 (t, 1H), 5.59 (s, 2H), 3.57 (t, 4H), 3.41-3.26 (m, 2H), 2.48-2.33 (m, 6H)

LCMS m/z 328/330 (M+H)⁺ (ES⁺)

(ii) 3-Amino-N-(2-morpholinoethyl)-5-((triisopropylsilyl)ethynyl)benzamide

Pd(PPh₃)₄ (2.90 g, 2.51 mmol) was added to a degassed suspension of the product of step (i) above (16.5 g, 50.3 mmol), CuI (0.479 g, 2.51 mmol), and ethynyltriisopropylsilane (16.92 mL, 75 mmol) in TEA (30 mL) and DMF (150 mL). Heated at 85° C. (block temp.) for 5 h, cooled and filtered (Whatman glass fibre pad GF/C). Solvents evaporated and the residue partitioned between EtOAc (500 mL) and 20% w/w NaCl soln. (500 mL). Aqueous layer was separated and washed with fresh EtOAc (500 mL). Organic layers bulked and washed with fresh 20% w/w NaCl soln. (500 mL), separated, dried (MgSO$_4$), filtered and solvent evaporated to a thick brown oil. The crude product was purified by chromatography on silica gel (220 g column, 2% MeOH:DCM to 10%) to afford the sub-title compound (18.5 g) as a pale yellow glass.

1H NMR (400 MHz, DMSO-d6) δ 8.29 (t, 1H), 7.04 (dd, 1H), 7.02 (t, 1H), 6.79 (dd, 1H), 5.44 (s, 2H), 3.57 (t, 4H), 3.37-3.28 (m, 2H), 2.47-2.36 (m, 6H), 1.11 (s, 21H)

LCMS m/z 430 (M+H)$^+$ (ES$^+$)

(iii) 3-Amino-5-ethynyl-N-(2-morpholinoethyl)benzamide

The product of step (ii) above (18.5 g, 43.1 mmol) was dissolved in EtOAc (250 mL) and TBAF, 1M in THF (43.1 mL, 43.1 mmol) added. Stirred for 1 h. Partitioned between water (500 mL) and ethyl acetate (200 mL) organic layer separated and washed with 20% w/w NaCl soln. (400 mL). Organic layer was separated, dried (MgSO$_4$) filtered and solvents evaporated. The crude product was slurried in Et$_2$O (100 mL) for 30 minutes filtered and washed with fresh Et$_2$O (20 mL). Oven dried at 45° C. to afford the sub-title compound (9.2 g)

1H NMR (400 MHz, DMSO-d6) δ 8.28 (t, 1H), 7.12-6.97 (m, 2H), 6.76 (t, 1H), 5.45 (s, 2H), 4.08 (s, 1H), 3.57 (t, 4H), 3.41-3.25 (m, 2H), 2.48-2.32 (m, 6H)

LCMS m/z 274 (M+H)$^+$ (ES$^+$)

(iv) tert-Butyl (4-((2-((3-ethynyl-5-((2-morpholino-ethyl)carbamoyl)phenyl)amino)-pyrimidin-4-yl)oxy) naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 6.46 g, 17.37 mmol), the product from step (iii) above (7.12 g, 26.0 mmol) and p-TSA monohydrate (5.62 g, 29.5 mmol) in DMF (60 mL) was heated at 60° C. (block temperature, 55° C. internal temperature) for 7 h. The mixture was cooled and added dropwise to sat. aq. NaHCO$_3$ (1 L). Solid was filtered and washed with water (50 mL) then isohexane (100 mL). The amorphous solid was stirred in MeOH (200 mL) and product crystallised. Slurried overnight, filtered and solid washed with MeOH (20 mL) and dried to give the sub-title compound (8 g).

1H NMR (400 MHz, DMSO-d6) δ 9.76 (s, 1H), 9.32 (s, 1H), 8.45 (d, 1H), 8.41-8.33 (m, 1H), 8.16-8.03 (m, 2H), 7.90 (t, 1H), 7.85-7.78 (m, 1H), 7.67-7.51 (m, 3H), 7.48-7.37 (m, 2H), 6.58 (d, 1H), 4.16 (s, 1H), 3.56 (t, 4H), 3.46-3.27 (m, 2H), 2.49-2.30 (m, 6H), 1.52 (s, 9H)

LCMS m/z 609 (M+H)$^+$ (ES$^+$)

(v) 3-((4-((4-Aminonaphthalen-1-yl)oxy)pyrimidin-2-yl)amino)-5-ethynyl-N-(2-morpholino-ethyl)benzamide TFA (22 mL, 286 mmol) was added dropwise to a stirred solution of the product of step (iv) above (9 g, 14.05 mmol) in DCM (50 mL). The reaction was stirred at rt for 2 h. The mixture was added dropwise to stirred water (100 mL) and 1M potassium carbonate solution (280 mL, 280 mmol) and stirring continued until effervescence ceased. The mixture was extracted with DCM (2×250 mL) then the combined organic phases were dried (MgSO$_4$) and concentrated under reduced pressure. The crude product was purified by chromatography on the Companion (120 g column, 2% MeOH:DCM to 6%) to afford the sub-title compound (6.7 g) as a pale brown foam.

1H NMR (400 MHz, DMSO-d6) δ 9.77 (s, 1H), 8.39 (t, 1H), 8.36 (d, 1H), 8.17-8.10 (m, 1H), 8.06 (s, 1H), 7.94 (dd, 1H), 7.67-7.59 (m, 1H), 7.49-7.38 (m, 3H), 7.15 (d, 1H), 6.70 (d, 1H), 6.37 (d, 1H), 5.79 (s, 2H), 4.20 (s, 1H), 3.56 (t, 4H), 3.41-3.30 (m, 2H), 2.48-2.34 (m, 6H)

LCMS m/z 509 (M+H)$^+$ (ES$^+$)

(vi) 3-Ethynyl-5-((4-((4-(3-(3-(2-methylbut-3-yn-2-yl)-1-(p-tolyl)-1H-pyrazol-5-yl)ureido)-naphthalen-1-yl)oxy)pyrimidin-2-yl)amino)-N-(2-morpholino-ethyl)benzamide To a stirred solution of phenyl (3-(2-methylbut-3-yn-2-yl)-1-(p-tolyl)-1H-pyrazol-5-yl)-carbamate (see Example 9(ii) above; 150 mg, 0.409 mmol) and the product of step (v) above (208 mg, 0.409 mmol) in isopropyl acetate (5 mL) was added triethylamine (8.84 μL, 0.063 mmol). The resulting solution was heated at 70° C. for 90 min. The reaction was cooled to rt and the solvent removed in vacuo. The crude product was purified by chromatography on silica gel (40 g column, 0-10% MeOH in DCM) to afford a semi-solid, which was triturated with a mixture of diethyl ether, acetonitrile and isohexane to afford the title compound (165 mg) as a white solid.

1H NMR (DMSO-d6) 400 MHz, δ: 9.77 (s, 1H), 9.15 (s, 1H), 8.87 (s, 1H), 8.84 (d, 1H), 8.41-8.34 (m, 1H), 8.08-8.06 (m, 2H), 7.95 (d, 1H), 7.86-7.81 (m, 2H), 7.66-7.62 (m, 1H), 7.59-7.56 (m, 1H), 7.50-7.48 (m, 2H), 7.44-7.39 (m, 4H), 6.57 (d, 1H), 6.54 (s, 1H), 4.13 (s, 1H), 3.59-3.53 (br m, 4H), 2H under H$_2$O peak at 3.35 ppm, 3.12 (s, 1H), 2.47-2.35 (m, 9H), 1.57 (s, 6H)

LCMS m/z 774 (M+H)$^+$ (ES$^+$)

Example 16

1-(3-(2-Methylbut-3-yn-2-yl)-1-(p-tolyl)-1H-pyrazol-5-yl)-3-(4-((2-((6-(2-morpholinoethoxy) pyridin-2-yl)amino)pyrimidin-4-yl)oxy)naphthalen-1-yl)urea

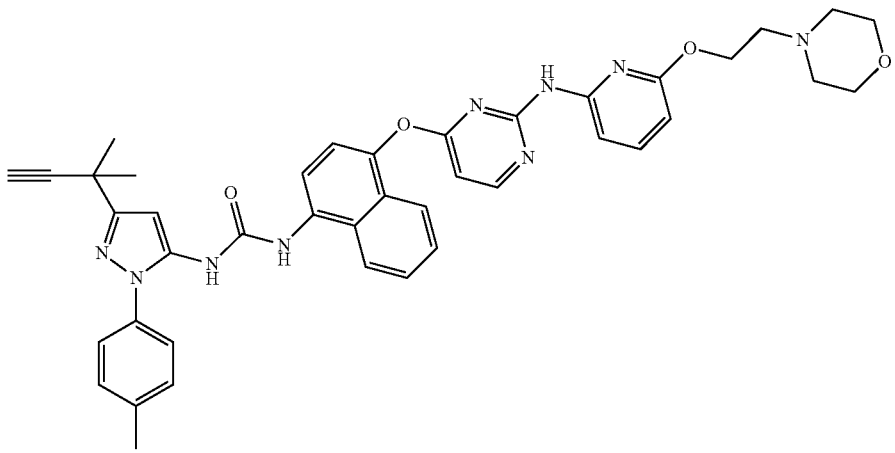 [SMILES: C#CC(C)(C)c1cc(NC(=O)Nc2ccc(Oc3ccnc(Nc4cccc(OCCN5CCOCC5)n4)n3)c3ccccc23)n(-c2ccc(C)cc2)n1]

(i) 6-(2-Morpholinoethoxy)pyridin-2-amine

Sodium hydride (60 Wt % in oil, 2.141 g, 53.5 mmol) was added portionwise to a stirred solution of 2-morpholinoethanol (6.48 ml, 53.5 mmol) stirring in dioxane (70 mL) at 0° C.-5° C. under $N_2$. This was left to stir for 30 min before 6-fluoropyridin-2-amine (2 g, 17.84 mmol) was added in dioxane (10 mL) over 10 min. After addition, reaction was heated to 90° C. overnight (18 h). The reaction was quenched by the slow addition of IPA (20 mL) followed by water (50 mL). Dioxane was then removed in vacuo and the residue partitioned between EtOAc and water (100 mL each). The organic phase was washed with saturated brine (2×30 mL) and then dried over $Na_2SO_4$, filtered and concentrated in vacuo to afford a light yellow solid. The crude product was purified by chromatography on the Companion (80 g column), using DCM:MeOH:$NH_3$; 0-5%, to afford the sub-title compound (3.16 g) as a pale yellow solid.

1H NMR (DMSO-d6) 400 MHz, δ: 7.34 (t, 1H), 6.09 (m, 2H), 4.32 (t, 2H), 4.32 (br s, 2H), 3.73 (t, 4H), 2.76 (t, 2H), 2.57 (t, 4H)

LCMS m/z 224 (M+H)$^+$ (ES$^+$)

(ii) 4-((4-Aminonaphthalen-1-yl)oxy)-N-(6-(2-morpholinoethoxy)pyridin-2-yl)pyrimidin-2-amine A mixture of tert-butyl (4-((2-chloropyrimidin-4-yl)oxy)naphthalen-1-yl)carbamate (see, for example, Ito, K. et al., WO 2010/067130, 17 Jun. 2010; 1.998 g, 5.37 mmol), the product of step (i) above (1.5 g, 6.72 mmol), caesium carbonate (2.63 g, 8.06 mmol), BINAP (0.837 g, 1.344 mmol) and Pd$_2$(dba)$_3$ (0.984 g, 1.075 mmol) in DMA (45 mL) was sparged with $N_2$ for 20 mins before heating to 80° C. for 16 h. Reaction was stopped and directly loaded onto a column of SCX in MeOH. The column was washed with MeOH and then the product was eluted with 0.7 M ammonia in MeOH. The resultant mixture was concentrated in vacuo to afford a dark brown solid. The residue was then taken up in DCM (70 mL) and trifluoroacetic acid (20.70 mL, 269 mmol) was added dropwise, reaction was left to stir under $N_2$ at rt for 2 h. Reaction was stopped and concentrated in vacuo. The dark brown crude product was loaded onto a column of SCX (15 g) in EtOAc. The column was washed with EtOAc followed by MeOH and then the product was eluted with 0.7 M ammonia in MeOH. The resultant mixture was concentrated in vacuo to afford the product as a dark brown oil. The crude product was purified by chromatography on silica gel (80 g column, DCM:MeOH:$NH_3$; 95:5: 0.05) to afford the sub-title compound (1.19 g) as a dark brown gum.

LCMS m/z 459 (M+H)$^+$ (ES$^+$)

(iii) 1-(3-(2-Methylbut-3-yn-2-yl)-1-(p-tolyl)-1H-pyrazol-5-yl)-3-(4-((2-((6-(2-morpholino-ethoxy)pyridin-2-yl)amino)pyrimidin-4-yl)oxy)naphthalen-1-yl)urea To phenyl (3-(2-methylbut-3-yn-2-yl)-1-(p-tolyl)-1H-pyrazol-5-yl)carbamate (see Example 9(ii) above; 200 mg, 0.556 mmol) stirring in iso-propyl acetate (3 mL) under $N_2$ at rt, was added the product of step (ii) above (319 mg, 0.556 mmol) in iso-propyl acetate (2 mL) followed by triethylamine (9.27 μL, 0.067 mmol) and the reaction mixture heated to 70° C. for 90 min. The reaction was stopped and concentrated in vacuo. The crude product was purified by chromatography on silica gel (12 g column, EtOAc:Isohexane 1:1 to 1:0) to afford a light brown solid. Impure by LCMS therefore re-purified by chromatography on silica gel (40 g column, DCM:MeOH:$NH_3$ to afford a light red solid which was purified by preparative HPLC to afford the title compound (20 mg) as a colourless solid.

1H NMR (DMSO-d6) 400 MHz; δ 9.44 (s, 1H), 9.20 (s, 1H), 8.84 (s, 1H), 8.45 (d, 1H), 8.09 (d, 1H), 8.04 (d, 1H), 7.94 (d, 1H), 7.80 (d, 1H), 7.62 (t, 1H), 7.55 (t, 1H), 7.48 (d, 2H), 7.40 (t, 3H), 7.13 (t, 1H), 6.89 (d, 1H), 6.54 (s, 1H), 6.21 (d, 1H), 4.27 (t, 2H), 3.52 (t, 4H), 3.10 (s, 1H), 2.59 (t, 2H), 2.41 (m, 7H), 1.54 (s, 6H).

LCMS m/z 724 (M+H)$^+$ (ES$^+$); 722 (M−H)$^-$ (ES$^-$)

Example 17

1-(4-((2-((6-(2-(2-(2-Methoxyethoxy)ethoxy)ethoxy)
pyridin-2-yl)amino)pyrimidin-4-yl)oxy)naphthalen-
1-yl)-3-(3-(2-methylbut-3-yn-2-yl)-1-(p-tolyl)-1H-
pyrazol-5-yl)urea

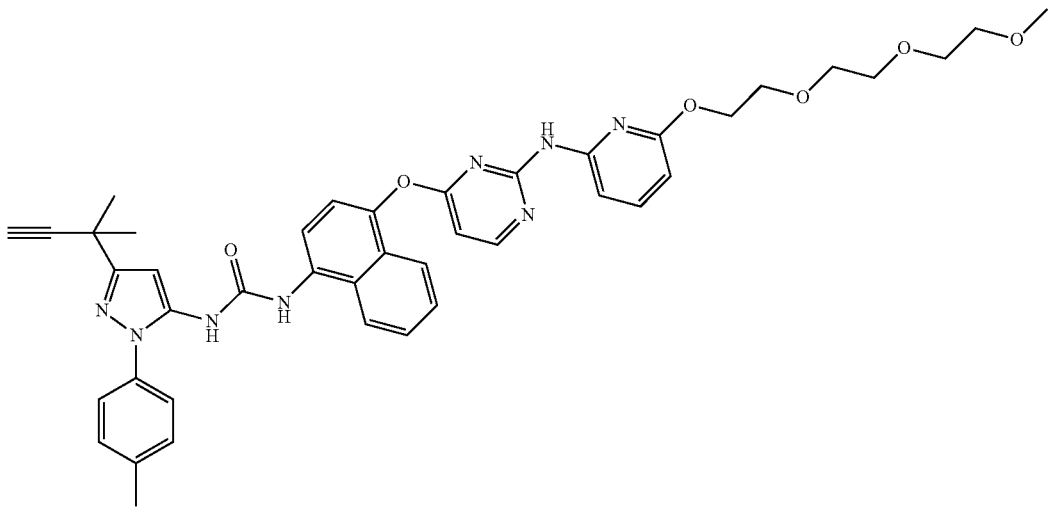 [SMILES: C#CC(C)(C)c1cc(NC(=O)Nc2ccc(Oc3ccnc(Nc4cccc(OCCOCCOCCOC)n4)n3)c3ccccc23)n(-c2ccc(C)cc2)n1]

(i) 6-(2-(2-(2-Methoxyethoxy)ethoxy)ethoxy)pyridin-2-amine

Sodium hydride (60 Wt % in oil, 2.141 g, 53.5 mmol) was added portionwise to a stirring solution of 2-(2-(2-methoxyethoxy)ethoxy)ethanol (8.57 ml, 53.5 mmol) stirring in dioxane (70 mL) at 0° C.-5° C. under $N_2$. This was left to stir for 30 min before 6-fluoropyridin-2-amine (2 g, 17.84 mmol) was added in dioxane (10 mL) over 10 min. After addition, reaction was heated to 90° C. overnight (18 h). The reaction was quenched by slow addition of IPA (20 mL) followed by water (50 mL). Dioxane was then removed in vacuo and the residue partitioned between EtOAc and water (100 mL each). The organic phase was washed with saturated brine (2×30 mL) and then dried over $Na_2SO_4$, filtered and concentrated in vacuo to afford the crude product which was purified by chromatography on silica gel (80 g column, DCM:MeOH:NH3, 0-10% MeOH to afford a light brown oil. The product was taken up in 1M HCl (200 mL) and washed with ether (2×100 mL). Aqueous was then treated with 2M NaOH to pH 15 and extracted with EtOAc (2×100 mL). The organic extracts were combined and washed with saturated brine (1×100 mL) and then dried over $Na_2SO_4$, filtered and concentrated in vacuo affording the sub-title compound (3.52 g).

1H NMR (DMSO-d6) 400 MHz; δ 7.26 (t, 1H), 5.97 (d, 1H), 5.85 (m, 3H), 4.72 (t, 2H), 3.67 (t, 2H), 3.51 (m, 6H), 3.42 (t, 2H), 3.23 (s, 3H).

LCMS m/z 258 (M+H)$^+$ (ES$^+$)

(ii) 4-((4-Aminonaphthalen-1-yl)oxy)-N-(6-(2-(2-(2-methoxyethoxy)ethoxy)ethoxy)pyridin-2-yl)pyrimidin-2-amine To a microwave vial was added the product of step (i) above (379 mg, 1.479 mmol), tert-butyl (4-((2-chloropyrimidin-4-yl)oxy)naphthalen-1-yl)carbamate (see, for example, Ito, K. et al., WO 2010/067130, 17 Jun. 2010; 500 mg, 1.345 mmol), caesium carbonate (657 mg, 2.017 mmol), palladium(II) acetate (7.55 mg, 0.034 mmol), BINAP (41.9 mg, 0.067 mmol) and dioxane (8 mL). The reaction mixture was purged with $N_2$ for 10 min and then irradiated at 100° C. for 15 mins. Reaction was filtered through Celite, the solids washed with MeOH and the filtrate concentrated in vacuo. The crude product was purified by chromatography on silica gel (40 g column, DCM:MeOH; 1-10% to afford a clear brown oil, 0.80 g. The residue was then taken up in DCM (20 mL) and TFA (5180 μL, 67.2 mmol) was added dropwise and left to stir under $N_2$ at rt for 1 h. Reaction was concentrated in vacuo leaving a brown oil. The crude product was loaded onto a column of SCX (20 g) in MeOH. The column was washed with MeOH and then the product was eluted with 0.7 M ammonia in MeOH. The resultant mixture was concentrated in vacuo to afford a light brown oil. The crude product required further purification by chromatography on silica gel (40 g column) using DCM:MeOH:NH3 (1%-5%) to afford the sub-title compound (360 mg) as a light brown oil which was used crude in the next step.

(iii) 1-(4-((2-((6-(2-(2-(2-Methoxyethoxy)ethoxy)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea To a stirred mixture of phenyl (3-(2-methylbut-3-yn-2-yl)-1-(p-tolyl)-1H-pyrazol-5-yl)-carbamate (see Example 9(ii) above; 200 mg, 0.557 mmol) and the product of step (ii) above (360 mg, 0.557 mmol) in i-PrOAc (6 mL) was added triethylamine (12.03 μL, 0.086 mmol). The resulting red solution was heated at 70° C. for 1 hour and 40 minutes. The reaction mixture was allowed to cool to room temperature and concentrated in vacuo to afford red viscous oil (0.52 g). The crude product was purified by chromatography on silica gel (80 g column, 0-10% MeOH in DMC) then purified further by chromatography on silica gel (80 g column, iso-hexane:ethyl acetate 1:1). Triturated with ether (2×2 mL) and the resultant solid was filtered, rinsing with ether, and dried in vacuo to afford the title compound (34 mg) as a clear white crystalline solid.

1H NMR (400 MHz, DMSO-d6) δ 9.45 (s, 1H), 9.19 (s, 1H), 8.83 (s, 1H), 8.45 (d, 1H), 8.08 (d, 1H), 7.95 (d, 1H), 7.80 (d, 1H), 7.66-7.59 (m, 1H), 7.58-7.52 (m, 1H), 7.49 (d, 2H), 7.41 (t, 3H), 7.14 (t, 1H), 6.89 (d, 1H), 6.68 (d, 1H), 6.55 (s, 1H), 6.23 (d, 1H), 4.30-4.21 (m, 2H), 3.69-3.62 (m, 2H), 3.54-3.45 (m, 6H), 3.38 (dd, 2H), 3.20 (s, 3H), 3.10 (s, 1H), 2.41 (s, 3H), 1.56 (s, 6H)

LCMS m/z 757 (M+H)$^+$ (ES$^+$); 755 (M−H)$^-$ (ES$^-$)

Biological Testing: Experimental Methods

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38a inactive target MAPKAP-K2 (Invitrogen, 600 ng/mL) and FRET peptide (8 μM; a phosphorylation target for MAPKAP-K2) is then added and the kinase reaction is initiated by adding ATP (400 μM, 2.5 μL). The mixture is incubated for 1 hr at RT. Development reagent (protease, μL) is added for 1 hr prior to detection in a fluorescence microplate reader (Varioskan® Flash, ThermoFisher Scientific).

Method 2

This method follows the same steps as Method 1 above, but utilises a higher concentration of the p38 MAPKα protein (2.5 μL of 200 ng/mL protein instead of 2.5 μL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) is then added to the enzymes/compound mixtures and incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 4 μg/mL, 0.4 μg/mL, 0.04 μg/mL, or 0.004 μg/mL, 2.5 μL each) for 2 hr at RT. The FRET peptides (8 μM. 2.5 μL), and appropriate ATP solutions (2.5 μL, 800 μM for c-Src, and 60 μM ATP for Syk) are then added to the enzymes/compound mixtures and incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration (IC$_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays

The compounds of the invention were studied using one or more of the following assays.

(a) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 μg/mL of LPS (from *E. Coli:* 0111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration (REC$_{50}$) is determined from the resultant concentration-response curve. The inhibition of IL-8 production is calculated at each concentration of test compound by comparison with vehicle control. The 50% inhibitory concentration (IC$_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (*Escherichia Coli* 0111:B4 from Sigma Aldrich) for 24 hours under normal tissue culture conditions (37° C., 5% CO$_2$). The supernatant is harvested for determination of IL-8 and TNFα concentrations by sandwich ELISA (Duo-set, R&D systems) and read on the fluorescence microplate reader (Varioskan® Flash, ThermoFisher Scientific). The concentration at 50% inhibition (IC$_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD38 monoclonal antibodies (0.3 μg/mL eBioscience and 3 μg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The IC$_{50}$ is determined from the dose response curve.

(d) IL-1-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly 1:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with of substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a hr exposure to varying concentrations of test compounds. At 2 hr before collection, PBMCs are treated with demecolcine (0.1 μg/mL; Invitrogen, Paisley, UK) to arrest cells in metaphase. To observe mitotic cells, PBMCs are permeabilised and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research,* 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting Hela cells with HRV until 80% of the cells are cytopathic.

BEAS2B cells are infected with HRV at an MOI of 5 and incubated for 2 hr at 33° C. with gentle shaking for to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution by 1% SDS solution. The measured $OD_{450\text{-}655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced CPE in MRC5

MRC-5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 μL), fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 μL) for 20 min, washed with WB (3×200 μL), (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No. ab43812, Abcam) in 5% BSA in PBS-tween. After washing, cells are incubated with an HRP-conjugated secondary antibody solution (50 µL) in 5% BSA in PBS-Tween (lot 00053170, Cat. No. P0447, Dako) and then TMB substrate added (50 µL; substrate reagent pack, lot 269472, Cat. No. DY999, R&D Systems, Inc.). This reaction is stopped by the addition of 2N $H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1P and TNFα levels by R&D ELISA.

Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of p-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-p-catenin antibody solution (50 µL) in 1% BSA/PBS (BD, Oxford, UK).

After washing with washing buffer (3×200 µL; PBS containing 0.05% Tween-20), cells are incubated with an HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, ThermoFisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of N-(4-(4-(3-(3-tert-butyl-1-p-tolyl-1H-pyrazol-5-yl)ureido)naphthalen-1-yloxy)pyridin-2-yl)-2-methoxyacetamide (1 µg/mL) which is defined as unity. A signal less than 0.15 of that observed for the standard control is designated as "-ve".

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at 2×10⁵ cells per well in 100 µL RPMI/10% FBS on 96 well flat bottomed plate (Corning Costar). 25 µL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$, and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs (2×10⁵ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 μg/mL streptomycin, 50 μg/mL gentamycin, and 1 μg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3 \times 10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Dearanulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 μg/mL) and 1 mM $CaCl_2$) to achieve $5 \times 10^6$ cells/mL.

$5 \times 10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 μM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5 \times 10^4$ TK6 cells (lymphoblastic T cell line) are added to the appropriate number of wells of a 96 well plate in 195 μL of media (RPMI supplemented with 10% foetal bovine serum). 5 μL of DMSO control (final concentration 0.5% v/v) or test compound (final concentration either 5 or 1 μg/mL) is added to the wells and incubated at 37° C., 5% $CO_2$. After 24 hours, the plate is centrifuged at 1300 rpm for 3 minutes and the supernatant discarded. Cells are then resuspended in 7.5 μg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 μL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day+6 the large intestine is removed and the length and weight are recorded. Sections of the colon are taken for either MPO analysis to determine neutrophil infiltration or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 μL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

(v) Adoptive Transfer in Mice

On Study day 0, female Balb/C mice are terminated and spleens obtained for CD45RB$^{high}$ cell isolation (Using SCID IBD cell Separation protocol). Approximately $4 \times 10^5$ cells/mL CD45RB$^{high}$ cells are then injected IP (100 µL/mouse) into female SCID animals. On study day 14, mice are weighed and randomized into treatment groups based on body weight. On Day 21 compounds are administered BID, via oral gavage, in a peanut oil vehicle at the dose levels outlined below and a dose volume of 5 mL/kg. Treatment continues until study day 42, at which point the animals are necropsied 4 hours after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

Summary of In Vitro and In Vivo Screening Results

TABLE 1

Results from in vitro p38 MAPKα (Method 2), c-Src, Syk and GSK3α (Method 2) inhibition assays

| Test Compound | IC50 Values for Enzyme Inhibition (nM) | | | |
|---|---|---|---|---|
| Example No. | p38 MAPKα | c-Src | Syk | GSK3α |
| 1 | 85 | 60 | >1,000 | >10,000 |
| 2 | 380 | 24 | 50 | >10,000 |
| 3 | 87 | 203 | 113 | >10,000 |
| 4 | — | — | — | 539 |
| 5 | — | — | — | 602 |
| 6 | — | — | — | 243 |
| 7 | 271 | 81 | 185 | >10,000 |
| 8 | — | 22 | 31 | 2573 |
| 9 | — | — | — | >10,000 |
| 10 | 46 | — | — | 1759 |
| 11 | — | — | — | >10,000 |
| 12 | 214 | 74 | 275 | 2,314 |
| 13 | 152 | 16 | 61 | 6,398 |
| 14 | 273 | 37 | 203 | 5,440 |
| 15 | 67 | 16 | 40 | 3,588 |
| 16 | 148 | 21 | 348 | >10,000 |
| 17 | — | — | — | >10,000 |

TABLE 2

Results from cellular assays in d-U937 cells, PBMCs and HT29 cells (the protocols for which are described by assays (a) to (d) above).

| Test Compound | IC$_{50}$ Values for Inhibition of Cytokine Release (nM) | | | | | |
|---|---|---|---|---|---|---|
| | dU937 cells | | PBMCs | | | HT29 cells |
| Example No. | IL-8 | TNFα | IL-8 | IL-2 | IFNγ | IL-8 |
| 1 | 3.2 | 1.4 | 1.6 | — | — | — |
| 2 | 0.9 | 0.4 | 2.0 | 18.0 | 3.6 | 3.2 |
| 3 | 4.4 | 2.8 | 2.1 | 0.7 | — | 6.0 |
| 4 | — | — | 0.5 | — | — | — |
| 5 | — | — | 1.0 | — | — | — |
| 6 | — | — | 0.6 | — | — | — |
| 7 | — | — | 4.0 | 138.8 | 21.8 | — |
| 8 | — | — | 1.4 | — | — | — |
| 9 | — | — | 7.6 | — | — | — |
| 10 | — | — | 1.7 | 7.1 | — | — |

TABLE 2-continued

Results from cellular assays in d-U937 cells, PBMCs and HT29 cells (the protocols for which are described by assays (a) to (d) above).

| Test Compound | IC$_{50}$ Values for Inhibition of Cytokine Release (nM) | | | | | |
|---|---|---|---|---|---|---|
| | dU937 cells | | PBMCs | | | HT29 cells |
| Example No. | IL-8 | TNFα | IL-8 | IL-2 | IFNγ | IL-8 |
| 11 | — | — | 10.8 | — | — | — |
| 12 | 1.2 | — | 2.1 | 171.4 | 2.6 | 3.7 |
| 13 | 0.5 | — | 1.7 | 58.8 | 1.3 | 1.7 |
| 14 | 1.8 | — | 1.4 | 169.6 | 2.0 | 3.6 |
| 15 | 1.3 | — | 0.8 | 69.3 | 2.4 | 2.5 |
| 16 | — | — | 17.7 | — | — | — |
| 17 | — | — | 30.4 | — | — | — |

The IC$_{50}$ for inhibition of TNFα release was also measured in PBMCs (using assay (b) above) for the compound of Example 1, and found to be 2.5 nM.

As illustrated in Table 3 below, the compound of Examples 2 and 13 were also screened in in vivo assay (iv) above, as conducted over 2 days. Histopathology analysis revealed that the compound of Examples 2 and 13 displayed significant activity in this in vivo model of colonic inflammation. In particular, those compounds, when dosed orally both at 5 mg/kg (or, for the compound of Example 2, at 1 and at 5 mg/kg), demonstrated marked improvements in ulcer grade and epithelial repair compared to the vehicle control. In addition, the compound of Examples 2 and 13 produced a marked reduction in inflammatory cell infiltrate in the reticular and lamina propria zones.

TABLE 3

Summary of results from studies on TNBS-induced colitis in mice.

| Experiment no. | Treatment group | n | TNBS Ulcer grade | LP inflammation |
|---|---|---|---|---|
| 1 | Non-diseased | 6 | 0.2 ± 0.2 | 0.3 ± 0.2 |
| 1 | TNBS + Vehicle | 12 | 4.0 ± 0.5 | 3.9 ± 0.3 |
| 1 | TNBS + Budesonide (2.5 mg/kg) | 11 | 2.9 ± 0.6 | 2.5 ± 0.4 |
| 1 | TNBS + Example 2 (1 mg/kg) | 12 | 3.4 ± 0.6 | 2.7 ± 0.4 |
| 1 | TNBS + Example 2 (5 mg/kg) | 12 | 2.4 ± 0.6 | 1.7 ± 0.4 |
| 2 | Non-diseased | 6 | 0.0 ± 0.0 | 0.2 ± 0.2 |
| 2 | TNBS + Vehicle | 24 | 4.4 ± 0.2 | 4.5 ± 0.2 |
| 2 | TNBS + Example 13 (1 mg/kg) | 12 | 3.0 ± 0.4 | 2.8 ± 0.3 |
| 2 | TNBS + Example 13 (5 mg/kg) | 12 | 2.9 ± 0.5 | 2.3 ± 0.3 |

As illustrated in Table 4 below, the compounds of Examples 2 and 13 were also screened in cellular assay (I), i.e., the ex-vivo human biopsy model described above, where it demonstrated significant anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Thus, the compound of Examples 2 and 13 significantly inhibited cytokine (IL-11, IL-6 and IL-8) release compared to the DMSO control when incubated, at 1 µg/mL, for 24 hours with biopsies from ulcerative colitis patients.

TABLE 4

Summary of results from assays using intestinal mucosa biopsies from the inflamed regions of the colon of various patients suffering from ulcerative colitis (a form of IBD).

| Treatment group | Cytokine release from biopsies of UC patients | | | | | |
|---|---|---|---|---|---|---|
| | n | IL-1β release | n | IL-6 release | n | IL-8 release |
| DMSO control | | 100% | | 100% | | 100% |
| Example 2 (1 µg/mL) | 3 | 20 ± 13 | 8 | 37 ± 41 | 8 | 22 ± 21 |
| Example 13 (1 µg/mL) | 5 | 3 ± 3 | 5 | 37 ± 52 | 5 | 7 ± 8 |

ABBREVIATIONS

AcOH glacial acetic acid
aq aqueous
ATP adenosine-5'-triphosphate
BALF bronchoalveolar lavage fluid
BINAP 2,2'-bis(diphenylphosphino)-1,1'-binaphthyl
br broad
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCM dichloromethane
DMAP 4-dimethylaminopyridine
DMF dimethylformamide
DMSO dimethyl sulfoxide
d-U937 cells PMA differentiated U-937 cells
(ES⁺) electrospray ionization, positive mode
Et ethyl
Et₃N triethylamine
EtOAc ethyl acetate
EtOH ethanol
FCS foetal calf serum
FRET fluorescence resonance energy transfer
GSK3α glycogen synthase kinase 3α
HBEC primary human bronchial epithelial cells
HPLC high performance liquid chromatography
hr hour(s)
HRP horseradish peroxidise
HRV human rhinovirus
ICAM-1 inter-cellular adhesion molecule 1
JNK c-Jun N-terminal kinase
LC liquid chromatography
LPS lipopolysaccharide
(M+H)⁺ protonated molecular ion
MAPK mitogen-activated protein kinase
MAPKAP-K2 mitogen-activated protein kinase-activated protein kinase-2
Me methyl
MeCN acetonitrile
MeOH methanol
MHz megahertz
min minute(s)
MMAD mass median aerodynamic diameter
MOI multiplicity of infection
MTT 3-(4,5-dimethylthiazol-2-yl)-2,5-diphenyltetrazolium bromide
MS mass spectrometry
m/z: mass-to-charge ratio
NMP N-methyl pyrrolodinone
NMR nuclear magnetic resonance (spectroscopy)
PBMC peripheral blood mononuclear cell
PBS phosphate buffered saline
Ph phenyl
PHA phytohaemagglutinin
PMA phorbol myristate acetate
p-TsOH 4-methylbenzenesulfonic acid (para-toluenesulfonic acid)
q quartet
rt room temperature
RP HPLC reverse phase high performance liquid chromatography
RSV respiratory syncytial virus
s singlet
sat saturated
SCX solid supported cation exchange (resin)
SDS sodium dodecyl sulphate
S$_N$Ar nucleophilic aromatic substitution
t triplet
T3P 1-propanephosphonic acid cyclic anhydride
TBAF tetrabutylammonium fluoride
TBDMS tert-butyldimethylsilyl
TCID₅₀ 50% tissue culture infectious dose
TEA triethylamine
THF tetrahydrofuran
TFA trifluoroacetic acid
TNFα tumor necrosis factor alpha Prefixes n-, s-, i-, t- and tert- have their usual meanings: normal, secondary, iso, and tertiary.

What is claimed is:

1. A compound of formula I,

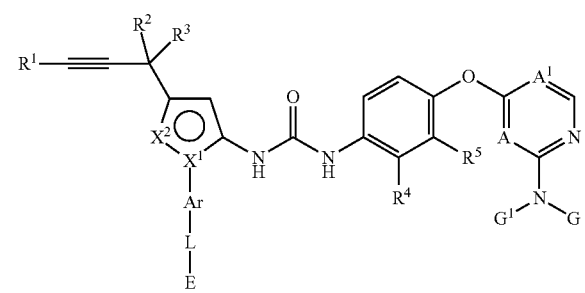

wherein
R¹ represents H or C$_{1-3}$ alkyl;
R² and R³ independently represent H or C$_{1-3}$ alkyl, or R² and R³ together combine to form C$_{2-3}$ alkylene;
X¹ and X² are both N, or X¹ is C and X² is either O or S;
Ar is phenyl or a 5- or 6-membered heteroaryl group containing one or more heteroatoms selected from the group consisting of N, O and S, which phenyl and heteroaryl groups are optionally substituted by one or more substituents selected from the group consisting of halo, C$_{1-4}$ alkyl, C$_{1-4}$ haloalkyl, C$_{1-4}$ alkoxy, hydroxy, amino and cyano;
L is a direct bond or C$_{1-2}$ alkylene;
E represents:
(a) H, halo, hydroxy, NR$^{6a}$R$^{6b}$, cyano, C(O)OR$^{6c}$, C(O)NR$^{6d}$R$^{6e}$, SH, S(O)$_n$R$^8$, S(O)$_2$NR$^{6f}$R$^{6g}$,
(b) C$_{1-8}$ alkyl, C$_{2-8}$ alkenyl, C$_{2-8}$ alkynyl, C$_{1-8}$ alkoxy, which latter four groups are optionally substituted by one or more substituents selected from the group consisting of halo and NR$^{7a}$R$^{7b}$, (c) $C_{3-8}$ cycloalkyl, $Het^1$ or $Ar^1$, which latter three groups are optionally substituted by one or more substituents selected from the group consisting of halo, hydroxy and $C_{1-3}$ alkyl;

$R^{6a}$ to $R^{6g}$ independently represent H or $C_{1-4}$ alkyl, or any one or more of the pairs $R^{6a}$ and $R^{6b}$, $R^{6d}$ and $R^{6e}$, and $R^{6f}$ and $R^{6g}$, when taken together with the N-atom to which each pair is attached, form a saturated 4- to 7-membered heterocyclic group, which heterocyclic group contains one N atom (the atom to which the pairs of substituents are attached) and, optionally, one or more further heteroatoms selected from the group consisting of O, S and N, and which heterocyclic group is optionally substituted by one or more $C_{1-2}$ alkyl groups;

$R^{7a}$ and $R^{7b}$, independently on each occurrence, represent H or $C_{1-4}$ alkyl, or, together with the N-atom to which they are attached, form a 5- to 7-membered heterocyclic group that is fully saturated, partially unsaturated or fully aromatic and which heterocyclic group contains one N atom (the atom to which $R^{7a}$ and $R^{7b}$ are attached) and, optionally, one or more further heteroatoms selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy;

$R^8$ represents $C_{1-4}$ haloalkyl, $C_{1-4}$ alkyl, $C_{3-8}$ cycloalkyl or $Ar^2$, which latter three groups are optionally substituted by one or more substituents selected from the group consisting of halo, hydroxy and $C_{1-3}$ alkyl;

$Ar^1$ and $Ar^2$ independently represent $C_{6-14}$ carbocyclic aryl groups, which groups may be monocyclic, bicyclic or tricyclic and which groups contain at least one ring which is fully aromatic, n is 0, 1 or 2;

$R^4$ and $R^5$ are each independently $C_{1-3}$ alkyl, $C_{1-3}$ haloalkyl, cyano or halo, or $R^4$ and $R^5$ together combine to form $C_{3-5}$ alkylene or $C_{3-5}$ alkenylene, which latter two groups are optionally substituted by one or more substituents selected from the group consisting of $C_{1-3}$ alkyl, $C_{1-3}$ haloalkyl, cyano and halo, or $R^4$ and $R^5$, together with the C-atoms to which they are attached, form a fused phenyl or $Het^2$ ring, which latter two rings are optionally substituted by one or more substituents selected from the group consisting of $C_{1-3}$ alkyl, $C_{1-3}$ haloalkyl, cyano and halo;

$Het^1$ and $Het^2$ independently represent 5- to 7-membered heterocyclic groups that are fully saturated, partially unsaturated or fully aromatic, which heterocyclic groups contain one or more heteroatoms selected from the group consisting of N, O and S;

one of A and $A^1$ represents N and the other represents CH, or both of A and $A^1$ represent CH;

G represents
phenyl optionally substituted by one or more $Y^1$ or $Het^3$ optionally substituted by one or more $Y^2$;

$G^1$ represents H;

or G and $G^1$ together combine to form $C_{3-6}$ alkylene optionally substituted by one or more substituents selected from the group consisting of halo, hydroxy and $C_{1-3}$ alkyl, which latter group is optionally substituted by one or more halo atoms or by hydroxy;

each $Y^1$ is independently selected from the group consisting of:
halo, hydroxy, cyano, $SF_5$, $-OC(O)NH_2$,
$P(O)R^{9a}R^{9b}$,
$J^1-N(R^{9c})R^{9d}$,
$J^2-S(O)_2R^{9e}$,
$J^3-[CH_2(CH_2)_{0-1}CH_2-O]_{2-8}-R^{9f}$,
$-C\equiv C-R^{9g}$,
$-N=S(O)R^{9h}R^{9i}$, $Het^a$, and
$C_{1-6}$ alkyl, $C_{3-6}$ cycloalkyl, $C_{1-6}$ alkoxy, $C_{3-6}$ cycloalkoxy, $-S(O)_{0-1}-C_{1-6}$ alkyl and $-S(O)_{0-1}-C_{3-6}$ cycloalkyl which latter six groups are optionally substituted by one or more substituents selected from the group consisting of halo, hydroxy, $C_{1-3}$ alkyl, $C_{1-3}$ alkoxy and $C_{3-6}$ cycloalkyl;

each $Y^2$ independently represents oxo or $Y^1$;

$J^1$ represents
a direct bond,
$-C(O)-$
$-[C(O)]_p-C_{1-8}$ alkylene,
$-C(O)NR^{10a}-CH_2-[C_{1-7}$ alkylene]-,
$-Q^1-CH_2-[C_{1-5}$ alkylene]-,
the alkylene parts of which latter four groups are optionally substituted by one or more substituents selected from the group consisting of halo, $C_{1-3}$ alkyl and hydroxy;

$J^2$ represents
a direct bond,
$-O-$,
$-NH-$
$C_{1-6}$ alkylene or
$-Q^2-CH_2-[C_{1-5}$ alkylene]-,
the alkylene parts of which latter two groups are optionally substituted by one or more substituents selected from the group consisting of halo, $C_{1-3}$ alkyl and hydroxy;

$J^3$ represents $-O-$ or $S(O)_{0-2}$;

$Q^1$ and $Q^2$ independently represent O or $S(O)_{0-2}$;

p represents 0 or 1;

$R^{9a}$ and $R^{9b}$ independently represent $C_{1-3}$ alkyl or $C_{1-3}$ alkoxy, or $R^{9a}$ and $R^{9b}$ together combine to form $C_{4-6}$ alkylene;

$R^{9c}$ and $R^{9d}$ independently represent H or $C_{1-8}$ alkyl, which latter group is optionally substituted by $R^{10b}$ and/or one or more substituents selected from the group consisting of halo and hydroxy; or $R^{9c}$ and $R^{9d}$, together with the N-atom to which they are attached, form a 4- to 7-membered heterocyclic group that is fully saturated, partially unsaturated or fully aromatic and which heterocyclic group contains one N atom (the atom to which $R^{9c}$ and $R^{9d}$ are attached) and, optionally, one or more further heteroatoms selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy;

$R^{9e}$ represents $C_{1-6}$ alkyl, $C_{3-6}$ cycloalkyl or phenyl, which latter three groups are optionally substituted by one or more substituents selected from the group consisting of halo, hydroxy, $C_{1-3}$ alkyl, $C_{1-3}$ alkoxy and $C_{3-6}$ cycloalkyl;

$R^{9f}$, $R^{9g}$, $R^{9h}$ and $R^{9i}$ independently represent $C_{1-4}$ alkyl optionally substituted by one or more halo atoms, or $R^{9f}$ and $R^{9g}$ independently represent H;

$R^{10a}$ represents H or $C_{1-3}$ alkyl optionally substituted by one or more halo atoms;

$R^{10b}$ represents $C_{1-4}$ alkoxy, $S-C_{1-4}$ alkyl, phenyl or $Het^4$, which latter two groups are optionally substituted by one or more substituents selected from the group consisting of halo, $C_{1-4}$ alkyl, $C_{1-4}$ haloalkyl, $C_{1-4}$ alkoxy, hydroxy, amino and cyano;

$Het^3$ represents a 5- to 10-membered heteroaromatic group, which group is monocyclic or bicyclic and contains at least one carbocyclic or heterocyclic ring that is fully aromatic, and which group contains one or more heteroatoms selected from the group consisting of N, O and S;

$Het^4$ represents a 4- to 10-membered heterocyclic group that is fully saturated, partially unsaturated or fully aromatic, which heterocyclic group contains one or more heteroatoms selected from the group consisting of N, O and S;

Het$^a$ represents a 5- or 6-membered heterocyclic group that is fully saturated, partially unsaturated or fully aromatic, which group contains one or more heteroatoms selected from the group consisting of N, O and S, and which group is optionally substituted by one or more substituents selected from the group consisting of halo, hydroxy, $C_{1-3}$ alkyl, $C_{1-3}$ alkoxy and $C_{3-6}$ cycloalkyl, or a pharmaceutically acceptable salt, solvate or isotopic derivative thereof.

2. A compound as claimed in claim 1 which is a compound of formula Ia,

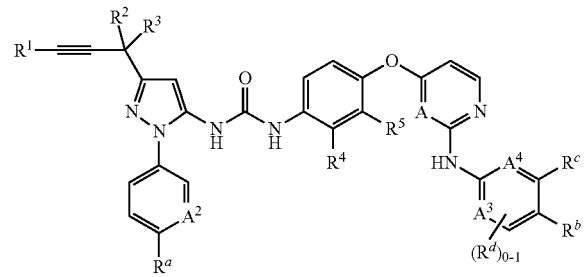

Ia wherein
$R^1$ represents H or $C_{1-2}$ alkyl;
$R^2$ and $R^3$ independently represent H or $C_{1-2}$ alkyl, or $R^2$ and $R^3$ together combine to form $C_2$ alkylene;
A represents CH or N;
$A^2$ represents CH or N;
$R^4$ and $R^5$ are both halo,
  or $R^4$ and $R^5$, together with the C-atoms to which they are attached, form a fused phenyl ring;
$R^a$ represents $C_{1-2}$ alkyl or $C_{1-2}$ alkoxy, which latter two groups are optionally substituted by one or more halo atoms, or $R^a$ represents $C_{1-2}$ alkyl or $C_2$ alkoxy, which latter two groups are substituted by $NR^{7a}R^{7b}$;
$R^{7a}$ and $R^{7b}$ both represent $C_{1-2}$ alkyl or, together with the N-atom to which they are attached, form a 5- or 6-membered heterocyclic group that is fully saturated and which heterocyclic group contains one N atom (the atom to which $R^{7a}$ and $R^{7b}$ are attached) and, optionally, one further heteroatom selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy;
$A^3$ and $A^4$ both represent CH, or one of $A^3$ and $A^4$ represents N and the other represents CH;
$R^b$, $R^c$ and $R^d$ independently represent H, halo, hydroxy, —C≡C—H, $C_{1-4}$ alkylene-$N(R^{9c})R^{9d}$, —C(O)NH—CH$_2$—[$C_{1-3}$ alkylene]-$N(R^{9c})R^{9d}$, -$Q^1$-CH$_2$—[$C_{1-3}$ alkylene]-$N(R^{9c})R^{9d}$, —O—[CH$_2$CH$_2$O]$_{2-7}$—$R^{9f}$, $C_{1-4}$ alkyl, $C_{1-4}$ alkoxy or C(O)NHC$_{1-4}$ alkyl, which latter three groups are optionally substituted by one or more halo atoms,
or $R^b$ and $R^c$, together with the C-atoms to which they are attached, form a fused, 5- or 6-membered heteroaromatic or heterocyclic ring, which ring:
  (i) contains one to three heteroatoms selected from the group consisting of N, O and S; and
  (ii) is optionally substituted by one or more substituents selected from the group consisting of H, halo, hydroxy, oxo, amino, $C_{1-2}$ alkyl and $C_{1-2}$ alkoxy, which latter two groups are optionally substituted by one or more halo atoms;

$R^{9c}$ and $R^{9d}$ both represent $C_{1-2}$ alkyl or, together with the N-atom to which they are attached, form a 5- or 6-membered heterocyclic group that is fully saturated and which heterocyclic group contains one N atom (the atom to which $R^{9c}$ and $R^{9d}$ are attached) and, optionally, one further heteroatom selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy; and $R^{9f}$ represents H or methyl, or a pharmaceutically acceptable salt, solvate or isotopic derivative thereof.

3. A compound as claimed in claim 2, which is a compound of formula Ib,

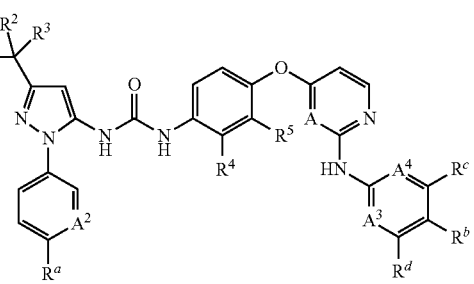

Ib or a pharmaceutically acceptable salt, solvate or isotopic derivative thereof, wherein $R^1$ to $R^5$, A, $A^2$, $A^3$, $A^4$ and $R^a$ to $R^d$ are as defined in claim 2.

4. A compound as claimed in claim 2 which is a compound of formula Ic, Id or Ie,

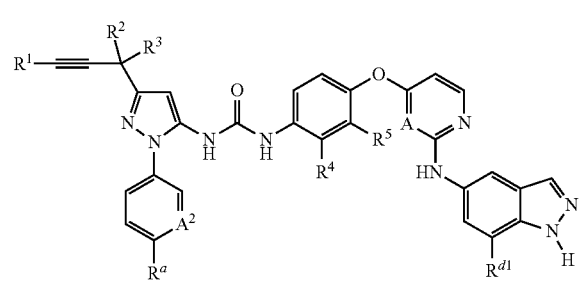

-continued

Ie

[Chemical structure Ie]

or a pharmaceutically acceptable salt, solvate or isotopic derivative thereof,
wherein:
$R^1$ to $R^5$, A, $A^2$ and $R^a$ are as defined in claim 2;
$R^{c2}$ and $R^{d2}$ are as defined above for $R^c$ and $R^d$ in claim 2;
$R^{d1}$ is as defined above for $R^d$ in claim 2; and
$A^x$ represents CH or N.

5. A compound as claimed in claim 2, wherein $R^1$ is H and $R^2$ and $R^3$ both represent methyl.

6. A compound as claimed in claim 2, wherein $A^2$ represents CH.

7. A compound as claimed in claim 2, wherein $R^a$ represents methyl.

8. A compound as claimed in claim 4, wherein $R^{d1}$ represents H or methyl.

9. A compound as claimed in claims 4, wherein:
(i) $R^{c2}$ represents H and $R^{d2}$ represents —O—[CH$_2$CH$_2$O]$_{2-7}$—CH$_3$, —C(O)NH—CH$_2$CH$_2$—N(R$^{9c}$)R$^{9d}$ or —O—CH$_2$CH$_2$—N(R$^{9c}$)R$^{9d}$,
(ii) both of $R^{c2}$ and $R^{d2}$ represent H, or
(iii) $R^{c2}$ represents CH$_3$, —C≡C—H, —CF$_3$, —OCF$_3$ or —OCH$_3$ and $R^{d2}$ represents —O—[CH$_2$CH$_2$O]$_{2-7}$—CH$_3$, —C(O)NH—CH$_2$CH$_2$—N(R$^{9c}$)R$^{9d}$ or —O—CH$_2$CH$_2$—N(R$^{9c}$)R$^{9d}$.

10. A compound as claimed in claim 1, wherein NR$^{9c}$R$^{9d}$ represents dimethylamino or morpholin-4-yl.

11. A compound as claimed in claim 1, wherein $R^4$ and $R^5$, together with the C-atoms to which they are attached, form a fused phenyl ring.

12. A compound as claimed in claim 1, which compound is selected from the group consisting of:
1-(3-(2-methylbut-3-yn-2-yl)-1-(p-tolyl)-1H-pyrazol-5-yl)-3-(4-((2-(phenylamino)pyrimidin-4-yl)oxy)naphthalen-1-yl)urea;
1-(4-((2-((7-methyl-1H-indazol-5-yl)amino)pyrimidin-4-yl)oxy)naphthalen-1-yl)-3-(3-(2-methylbut-3-yn-2-yl)-1-(p-tolyl)-1H-pyrazol-5-yl)urea;
1-(3-(2-methylbut-3-yn-2-yl)-1-(p-tolyl)-1H-pyrazol-5-yl)-3-(4-((2-((2-oxoindolin-6-yl)amino)pyrimidin-4-yl)oxy)naphthalen-1-yl)urea;
3-methoxy-5-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)benzamide;
1-(3-(2-methylbut-3-yn-2-yl)-1-(p-tolyl)-1H-pyrazol-5-yl)-3-(4-((2-((3-(2-morpholinoethoxy)phenyl)amino)pyrimidin-4-yl)oxy)naphthalen-1-yl)urea;
1-(4-((2-((3-(2-(dimethylamino)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea;
1-(3-(2-methylbut-3-yn-2-yl)-1-(p-tolyl)-1H-pyrazol-5-yl)-3-(4-((2-(phenylamino)pyridin-4-yl)oxy)naphthalen-1-yl)urea;
1-(4-((2-((3-methoxy-5-morpholinoethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea;
1-(2,3-dichloro-4-((2-((7-methyl-1H-indazol-5-yl)amino)pyrimidin-4-yl)oxy)phenyl)-3-(3-(2-methylbut-3-yn-2-yl)-1-(p-tolyl)-1H-pyrazol-5-yl)urea;
1-(4-((2-((6-(2-(dimethylamino)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea;
1-(4-((2-((4-(2-(dimethylamino)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea;
3-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethyl)benzamide;
1-(4-((2-((3-methoxy-5-(2-(2-(2-methoxyethoxy)ethoxy)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea;
3-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)-5-(trifluoromethoxy)benzamide;
3-ethynyl-5-((4-((4-(3-(3-(2-methylbut-3-yn-2-yl)-1-(p-tolyl)-1H-pyrazol-5-yl)ureido)naphthalen-1-yl)oxy)pyrimidin-2-yl)amino)-N-(2-morpholinoethyl)benzamide;
1-(3-(2-methylbut-3-yn-2-yl)-1-(p-tolyl)-1H-pyrazol-5-yl)-3-(4-((2-((6-(2-morpholinoethoxy)pyridin-2-yl)amino)pyrimidin-4-yl)oxy)naphthalen-1-yl)urea; and
1-(4-((2-((6-(2-(2-(2-methoxyethoxy)ethoxy)ethoxy)pyridin-2-yl)amino)pyrimidin-4-yl)oxy)naphthalen-1-yl)-3-(3-(2-methylbut-3-yn-2-yl)-1-(p-tolyl)-1H-pyrazol-5-yl)urea, or a pharmaceutically acceptable salt, solvate or isotopic derivative thereof.

13. A compound as claimed in claim 1, which compound is selected from the group consisting of:
1-(4-((2-((7-methyl-1H-indazol-5-yl)amino)pyrimidin-4-yl)oxy)naphthalen-1-yl)-3-(3-(2-methylbut-3-yn-2-yl)-1-(p-tolyl)-1H-pyrazol-5-yl)urea; and
1-(4-((2-((3-methoxy-5-(2-(2-(2-methoxyethoxy)ethoxy)ethoxy)phenyl)amino)pyrimidin-4-yl)oxy)naphthalen-1-yl)-3-(3-(2-methylbut-3-yn-2-yl)-1-(p-tolyl)-1H-pyrazol-5-yl)urea,
or a pharmaceutically acceptable salt, solvate or isotopic derivative thereof.

14. A pharmaceutical formulation comprising a compound as defined in claim 1, or pharmaceutically acceptable salt, solvate or isotopic derivative thereof, in admixture with a pharmaceutically acceptable adjuvant, diluent or carrier.

15. A combination product comprising
(A) a compound as defined in claim 1, or pharmaceutically acceptable salt, solvate or isotopic derivative thereof, and
(B) another therapeutic agent,
wherein each of components (A) and (B) is formulated in admixture with a pharmaceutically-acceptable adjuvant, diluent or carrier.

16. A method of treating inflammation, said method comprising administering to a subject an effective amount of:
a compound as defined in claim 1;
a pharmaceutical formulation comprising a compound as defined in claim 1;
a pharmaceutically acceptable salt of a compound as defined in claim 1, or a solvate or isotopic derivative thereof, in admixture with a pharmaceutically acceptable adjuvant, diluent or carrier, or a combination product comprising:
(A) a compound as defined in claim 1, or pharmaceutically acceptable salt, solvate or isotopic derivative thereof, and
(B) another therapeutic agent,
wherein each of components (A) and (B) is formulated in admixture with a pharmaceutically-acceptable adjuvant, diluent or carrier,
wherein the inflammation is a component in a disease selected from the group consisting of cystic fibrosis, pulmonary hypertension, lung sarcoidosis, idiopathic pulmonary fibrosis, Chronic Obstructive Pulmonary Disease (COPD), chronic bronchitis, emphysema), asthma, paediatric asthma, atopic dermatitis, allergic dermatitis, contact dermatitis or psoriasis, allergic rhinitis, rhinitis, sinusitis, conjunctivitis, allergic conjunctivitis, keratoconjunctivitis sicca (dry eye), glaucoma, diabetic retinopathy, macular oedema, diabetic macular oedema), central retinal vein occlusion (CRVO), dry and/or wet age related macular degeneration (AMD), post-operative cataract inflammation, uveitis, posterior uveitis, anterior uveitis, pan uveitis, corneal graft and limbal cell transplant rejection, gluten sensitive enteropathy (coeliac disease), eosinophilic esophagitis, intestinal graft versus host disease, Crohn's disease and ulcerative colitis.

17. The method according to claim 16, wherein the disease is asthma or COPD.

18. The method according to claim 16, wherein the disease is uveitis, Crohn's disease or ulcerative colitis.

19. A process for the preparation of a compound of formula I according to claim 1, which process comprises:
(a) reaction of a compound of formula II,

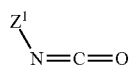

II with a compound of formula III,

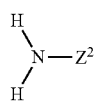

III wherein one of $Z^1$ and $Z^2$ is a structural fragment of formula IV

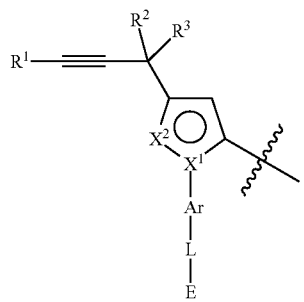

IV and the other of $Z^1$ and $Z^2$ is a structural fragment of formula V

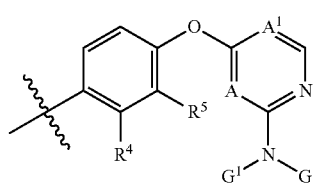

V where E, L, Ar, $X^1$, $X^2$, $R^1$ to $R^5$, A, $A^1$, G and $G^1$ are as defined in claim 1;

(b) reaction of a compound of formula IIa,

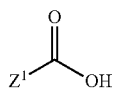

IIa wherein $Z^1$ is as defined above, with a suitable azide-forming agent,
which reaction is followed, without isolation, by thermal rearrangement of the intermediate acyl azide (of formula $Z^1$—C(O)—$N_3$) to provide, in situ, a compound of formula II, which compound is then reacted with a compound of formula III as defined above;

(c) reaction of a compound of formula IIb,

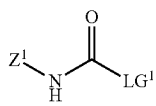

IIb wherein $LG^1$ represents a leaving group and $Z^1$ is as defined above, with a compound of formula III, as defined above;

(d) reaction of a compound of formula VI,

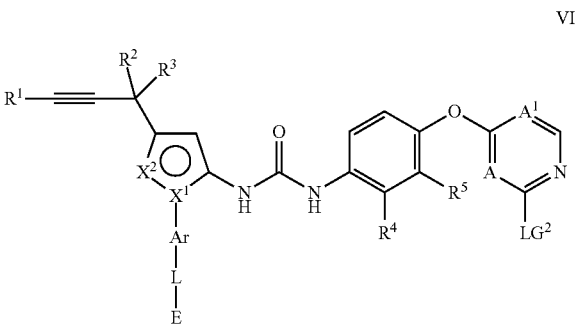

VI wherein $LG^2$ represents a leaving group and E, L, Ar, $X^1$, $X^2$, $R^1$ to $R^5$, A and $A^1$ are as defined in claim 1, with a compound of formula VII,

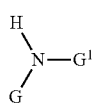

VII wherein G and $G^1$ are as defined in claim 1; or
(e) deprotection of an protected derivative of a compound of formula I, wherein the protected derivative bears a protecting group on an O— or N-atom of the compound of formula I.

* * * * *